US008637280B2

(12) United States Patent
Bauweleers et al.

(10) Patent No.: US 8,637,280 B2
(45) Date of Patent: Jan. 28, 2014

(54) GENES USEFUL FOR THE INDUSTRIAL PRODUCTION OF CITRIC ACID

(75) Inventors: Hugo Marc Karel Bauweleers, Boutersem (BE); Dominique Robert Groeseneken, Hoegaarden (BE); Noël Nicolaas Maria Elisabeth Van Peij, Delft (NL)

(73) Assignee: Adcuram Nutrition Holding GmbH, Munich (DE)

( * ) Notice: Subject to any disclaimer, the term of this patent is extended or adjusted under 35 U.S.C. 154(b) by 1008 days.

(21) Appl. No.: 12/094,804

(22) PCT Filed: Dec. 1, 2006

(86) PCT No.: PCT/EP2006/069218
§ 371 (c)(1),
(2), (4) Date: May 23, 2008

(87) PCT Pub. No.: WO2007/063133
PCT Pub. Date: Jun. 7, 2007

(65) Prior Publication Data
US 2009/0022873 A1  Jan. 22, 2009

(30) Foreign Application Priority Data

Dec. 1, 2005  (EP) .................................... 05026213
Dec. 1, 2005  (EP) .................................... 05026219
Dec. 1, 2005  (EP) .................................... 05026229
Dec. 1, 2005  (EP) .................................... 05026230

(51) Int. Cl.
*C12P 7/48*  (2006.01)
*C12N 1/00*  (2006.01)
*C12N 15/00*  (2006.01)
*C12N 15/74*  (2006.01)
*C07H 21/02*  (2006.01)

(52) U.S. Cl.
USPC ................... 435/144; 435/254.11; 435/320.1; 435/47.1; 536/23.1

(58) Field of Classification Search
None
See application file for complete search history.

(56) References Cited

U.S. PATENT DOCUMENTS 3,809,611 A  5/1974  Takayama et al.

FOREIGN PATENT DOCUMENTS

WO  2004/009828  1/2004
WO  WO2004-009828  *  1/2004

OTHER PUBLICATIONS

UniProt Accession No. Q2UJQ4, created Jan. 26, 2006.*
UniProt Accession No. Q2UTF0, created on Jan. 24, 2006.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Karaffa et al. Appl Microbiol Biotechnol 61:189-196, 2003.*
Narasipua et al. Mol Microbiol, 55(6):1782-1800, 2005, Epub, Jan. 21, 2005.*
International Search Report for PCT/EP2006/069218 dated Jul. 12, 2007.
Database UniProt "Transporter protein smf2" Jul. 5, 2005.
Database EMBL "Asn_05688 *Aspergillus niger* pBluescript (EcoRl-Xhol) *Aspergillus niger* cDNA clone Asn_05688, mRNA sequence" Jul. 16, 2005.
Nierman et al. "Genomic sequence of the pathogenic and allergenic filamentous fungus *Aspergillus fumigatus*" Nature 438:1151-1156, Dec. 29, 2005.
Semova et al. "Generation, annotation, and analysis of an extensive *Aspergillus niger* EST collection" BMC Microbiol. 6:7, ten pages, Feb. 2, 2006.
EBI Dbfetch; Q5B1E7; "Nucleotide Sequence (Large Scale Genomic DNA)", Apr. 26, 2005.

* cited by examiner

*Primary Examiner* — Iqbal H Chowdhury
(74) *Attorney, Agent, or Firm* — Nixon & Vanderhye

(57) ABSTRACT

The present invention relates to newly identified genes that encode proteins that are involved in the (bio)synthesis of citric acid. The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of said polynucleotides and polypeptides as biotechnological tools in the production of citric acid from microorganisms, whereby a modification of said polynucleotides and/or encoded polypeptides has a direct or indirect impact on yield, production, and/or efficiency of production of the fermentation product in said microorganism. Also included are methods/processes of using the polynucleotides and modified polynucleotide sequences to transform host microorganisms. The invention also relates to genetically engineered microorganisms and their use for production of citric acid.

11 Claims, 9 Drawing Sheets

GENES USEFUL FOR THE INDUSTRIAL PRODUCTION OF CITRIC ACID

This application is the U.S. national phase of International Application No. PCT/EP2006/069218, filed 1 Dec. 2006, which designated the U.S. and claims priority to European Application No. 05026229.4 filed 1 Dec. 2005, European Application No. 05026230.2 filed 1 Dec. 2005, European Application No. 05026213.8 filed 1 Dec. 2005, and European Application No. 05026219.5 filed 1 Dec. 2005; the entire contents of each of which are hereby incorporated by reference.

FIELD OF THE INVENTION

The present invention relates to newly identified genes that encode proteins that are involved in the (bio)synthesis of citric acid. The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of said polynucleotides and polypeptides as biotechnological tools in the production of citric acid from microorganisms, whereby a modification of said polynucleotides and/or encoded polypeptides has a direct or indirect impact on yield, production, and/or efficiency of production of the fermentation product in said microorganism. Also included are methods/processes of using the polynucleotides and modified polynucleotide sequences to transform host microorganisms. The invention also relates to genetically engineered microorganisms and their use for production of citric acid.

BACKGROUND OF THE INVENTION

Citric acid (2-hydroxy-propane-1,2,3-tricarboxylic acid) is known as an industrially important organic acid which is used e.g. as food additive, preservative or as stabilizer of oils and fats due to its ability to complex heavy metal ions like copper and iron. Originally, it has been isolated from citrus plants. Chemical synthesis of citric acid is also possible, however, not at all suitable for industrial production due to the expensive raw materials and a complicated process with low yield.

Therefore, over the past decades, other approaches to manufacture citric acid using microbial conversions, which would be more economical as well as ecological, have been investigated.

Citric acid production from a number of substrates including glucose or sucrose has been reported in several microorganisms, such as fungi including yeasts, using different cultivation methods. Examples of known fungi able to directly produce citric acid include, for instance, strains from the genera of *Aspergillus*, in particular *A. niger*, or yeasts such as *Yarrowia*, in particular *Yarrowia lipolytica*.

The conversion of a substrate e.g. carbohydrates, into citric acid may involve many different metabolic routes, and involve several enzymatic steps to generate citric acid. Furthermore, transporters may also play an important role in the efficient conversion of a substrate into citric acid.

Proteins, in particular transporters, that are active in the transport of substances such as carbohydrates like e.g. glucose or sugar alcohols, carboxylates, minerals, toxic compounds like reactive oxygen, and related compounds over a membrane are herein referred to as being involved in the Transport System. This transport can be into the cytosol, into/out of a mitochondrion, vacuole, endoplasmatic reticulum, peroxisome or across another membrane barrier. Such proteins are abbreviated herein as TS proteins and function in the synthesis of citric acid or have a function in the cellular process of citric acid synthesis.

TS proteins are in general membrane-bound or are associated to membrane-bound structures and are functional as single proteins or as subunits in protein complexes such as permeases or active transporters. TS proteins are known to be responsible for selectively facilitating, assisting or enabling the transport of compounds such as sugars, sugar alcohols, carboxylates, minerals, toxic compounds across the cellular, periplasmatic or mitochondrial vacuolar, endoplasmatic reticulum or peroxisomal membrane.

TS proteins can be divided into several types on the basis of their mechanisms. The first class of transporters, also called ion channels, uses energy from the proton-motive force to transport molecules against a concentration gradient. These symport and antiport systems couple the movement of two different molecules across the membrane (via permeases having two separate binding sites for the two different molecules); in symport, both molecules are transported in the same direction, while in antiport, one molecule is imported while the other is exported.

A further class of transporters, also called "secondary transporters", the phosphotransferase system (PTS), is energized by the transfer of a high-energy phosphate group from phosphoenolpyruvate, through various protein components, to the substrate which is phosphorylated upon import as its phosphoester form. Ion transporters of this group facilitate diffusion over a membrane, such as for example the cation diffusion facilitator (CDF) family or exchange anions such as for example the anion exchanger (AE) family. The group of major facilitator superfamily (MFS) contains many important sugar transporters.

A further class of transporters couples the hydrolysis of ATP to substrate translocation. These systems are termed the ATP-binding cassette (ABC) type transporters. The ABC-transport system consists of a substrate specific binding protein which is located in the periplasm in gram-negative bacteria or which is membrane associated in gram-positive bacteria, an integral membrane domain and a cytoplasmic-facing ATP hydrolyzing domain.

A more detailed description of membrane transport systems can be found in: Bamberg, E. et al (1993) "Charge transport of ion pumps on lipid bilayer membranes", Q. Rev. Biophys. 26:1-25; Findlay, J. B. C. (1991) "Structure and function of membrane transport systems", Curr. Opin. Struct. Biol. 1:804-810; Higgins, C. F. (1992) "ABC transporters from microorganism to man" Ann. Rev. Cell Biol. 8:67-113; Gennis, R. B. (1989) "Pores, channels and transporters" in: Biomembranes, Molecular Structure and Function, Springer, Heidelberg, p. 270-322; Nikaido, H. & Saier H. (1992) "Transport proteins in bacteria: common themes in their design" Science 258:936-942.

Preferably, the TS proteins or subunits of such proteins having activity towards or which are involved in the synthesis of citric acid from a carbohydrate are selected from the group consisting of hexose transporters, ion transporters, kinases, permeases, symporters, antiporters, mitochondrial carriers such as citrate transport proteins or tricarboxylate carriers, suppressors for mitochondrial histones, and metal transporters such as Manganese transporters or manganese resistance protein or iron transporters.

Proteins, in particular enzymes, that are involved in the citrate synthesis such as enzymes which take part in the TCA, like e.g. enzymes catalyzing the condensation of acetyl-CoA with oxaloacetate to form citric acid, are herein referred to as being involved in the Citrate-synthesis System and abbreviated as CS proteins which function in the synthesis of citric acid.

Preferably, the CS proteins or subunits of such proteins having activity towards or which are involved in citrate synthesis are selected from the group consisting of citrate synthases, glyoxysomal citrate synthases, aconitases, aconitate hydratases or hydrolylases, and 6-phosphofructokinases.

Proteins, in particular enzymes which are involved in side-reactions such as e.g. Mn-dependent mitochondrial superoxide dismutase (MnSOD), genes that are involved in so-called "by-pass routes" of the synthesis pathway of citric such as e.g. oxaloacetate hydrolases, glucose oxidase and/or glycolate (oxido-)reductases acid may have an influence in the cellular process of citric acid synthesis. Such enzymes are abbreviated herein as BS proteins or BS enzymes.

Production of citric acid using strains of *Aspergillus* has been reported previously (see, e.g. Karaffa and Kubicek, Appl Microbiol Biotechnol, 61:169-196, 2003). However, the yields and or productivity of citric acid production as known in the prior art may still be improved, which is an object of the present invention.

This plasmid is used for disruption of the BS08 gene. Indicated are the 5' BS08 flanking region (depicted as 5' sodA) and the 3' BS08 flanking regions (depicted as 3' sodA) relative to the amdS marker. The sequences of the BS08 3' fragments overlap at least a few hundred bp in sequence. The *E. coli* DNA was removed by digestion with restriction enzyme BstBI and XmaI, prior to transformation of the *A. niger* strains.

Figure 2:
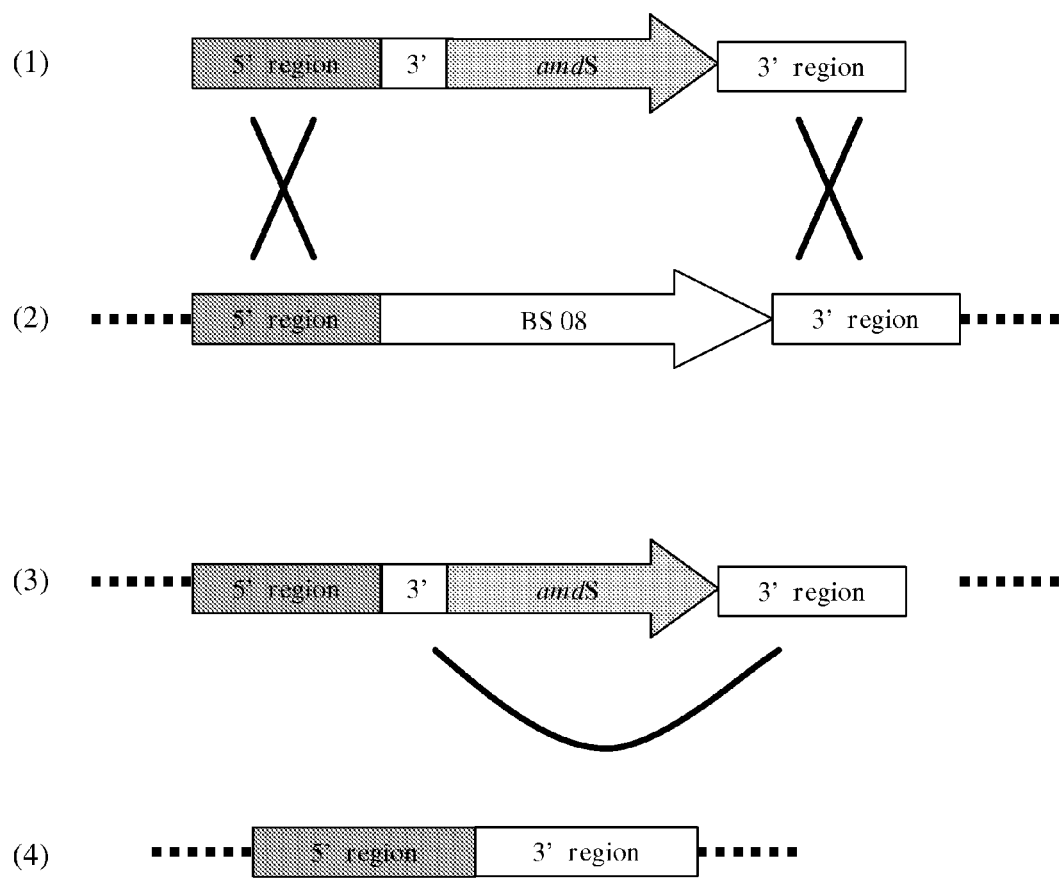

FIG. 2: Schematic representation of BS08 gene deletion.

A linear DNA construct of pGBDEL-SODA, comprising the amdS selection marker flanked by homologous regions (5' and 3') of the BS08 gene (1), integrates through double homologous recombination (X) at the genomic BS08 locus (2) and replaces the genomic BS08 gene copy (3). Subsequently, recombination over the direct repeats (U) removes the amdS marker, resulting in precise excision of the BS08 gene (4).

Figure 3:
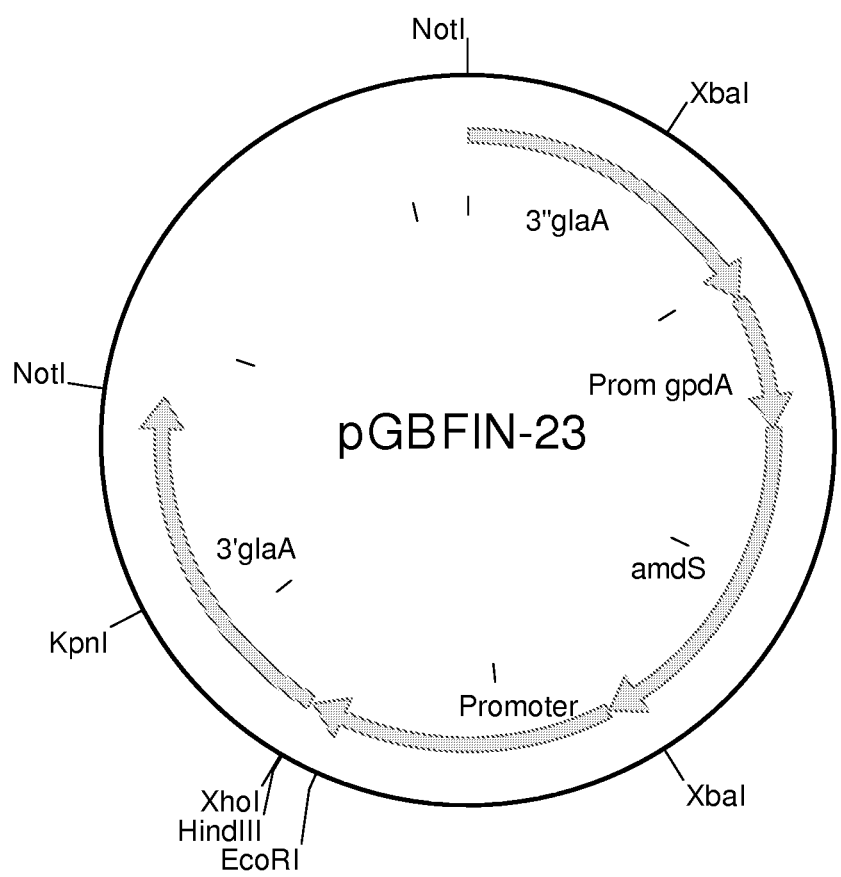

FIG. 3: Plasmid map of expression vector pGBFIN-23.

This is an example of a pGBFIN-based expression vector, such as pGBFIN-23. Indicated are the glaA flanking regions relative to the glaA promoter and HindIII-XhoI cloning site for a gene of interest. The *E. coli* DNA can be removed by digestion with restriction enzyme NotI, prior to transformation of the *A. niger* strains.

Figure 4:
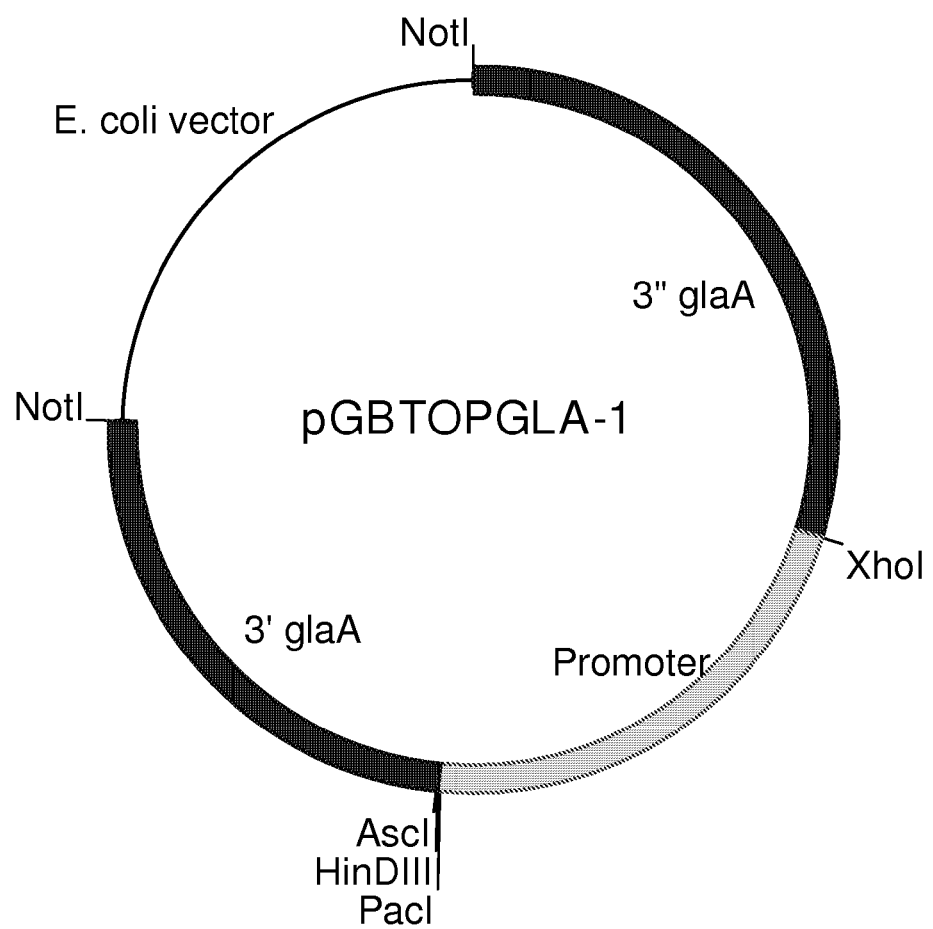

FIG. 4: Plasmid map of expression vector pGBTOPGLA-1.

This is an example of a pGBTOP-based expression vector. Indicated is the plasmid map of pGBTOPGLA-1, which is an integrative expression vector containing a promoter in operative association with a coding sequence of a gene of interest.

Figure 5:
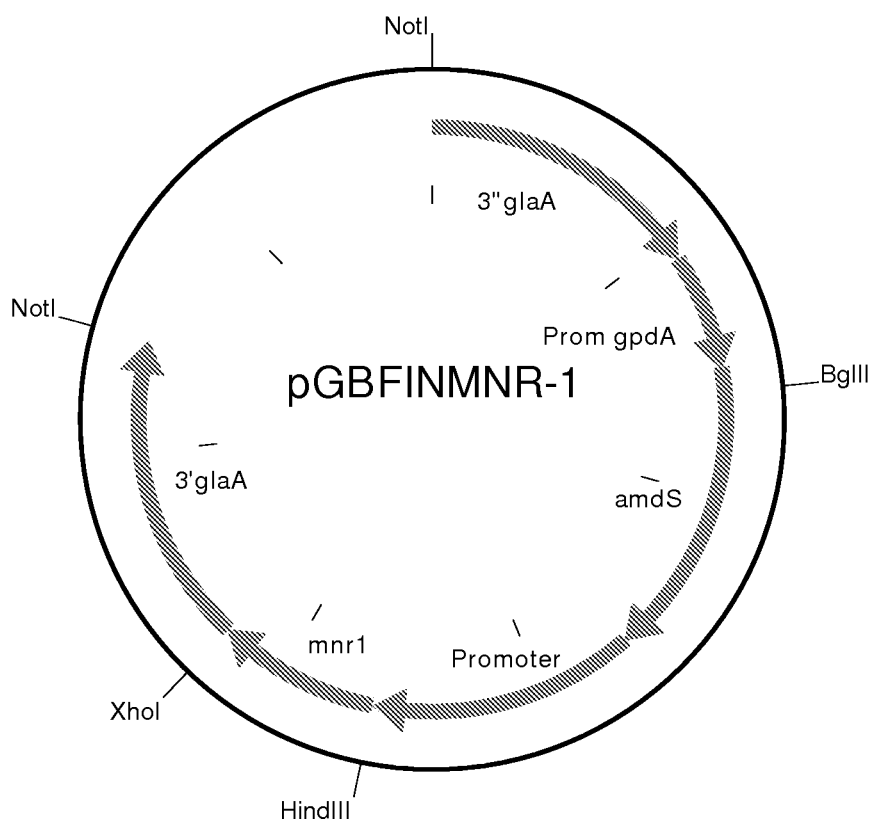

FIG. 5: Plasmid map of overexpression vector pGBFIN-MNR-1.

This plasmid comprises the TS08 gene, which is depicted as mnr1. Indicated are the glaA flanking regions relative to the glaA promoter and the insert encoding the manganese resistance protein of the invention in the HindIII-XhoI cloning site. The *E. coli* DNA can be removed by digestion with restriction enzyme NotI prior to transformation of the *A. niger* strains.

Figure 6:
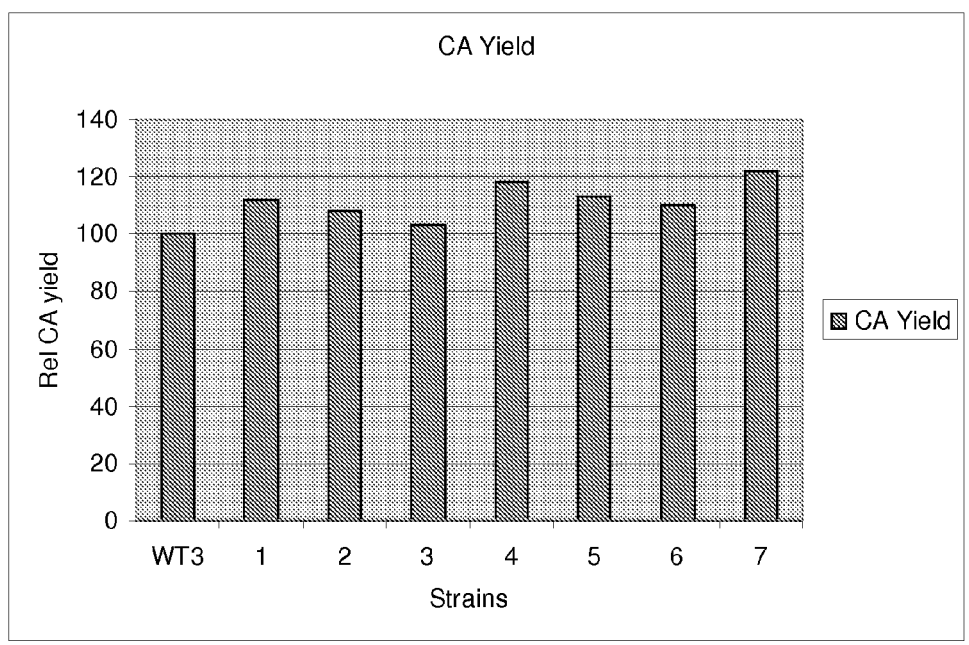

FIG. 6: Performance of overexpression strains in surface fermentation.

Indicated are the strains of Table 2, fermented as described in Example 4. Performance of the various strains is depicted as the yield of citric acid production compared to the yield of the WT3 strain, which was set at 100%.

Figure 7:
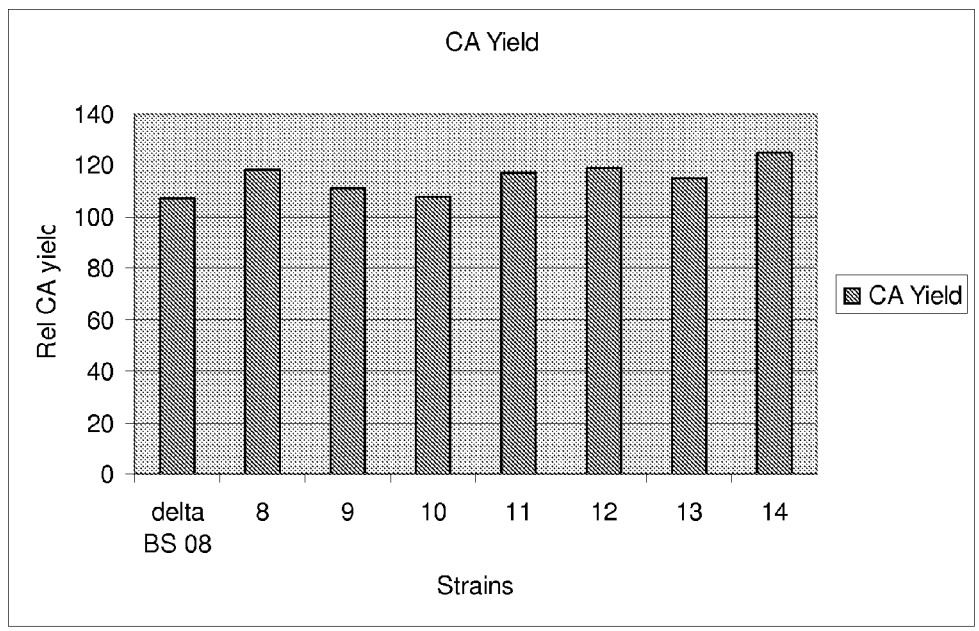

FIG. 7: Performance of overexpression strains in an BS08 disrupted background in surface fermentation.

Indicated are the strains of Table 2, fermented as described in Example 4. Performance of the various strains is depicted as the yield of citric acid production compared to the yield of the WT3 strain, which was set at 100%.

Figure 8:
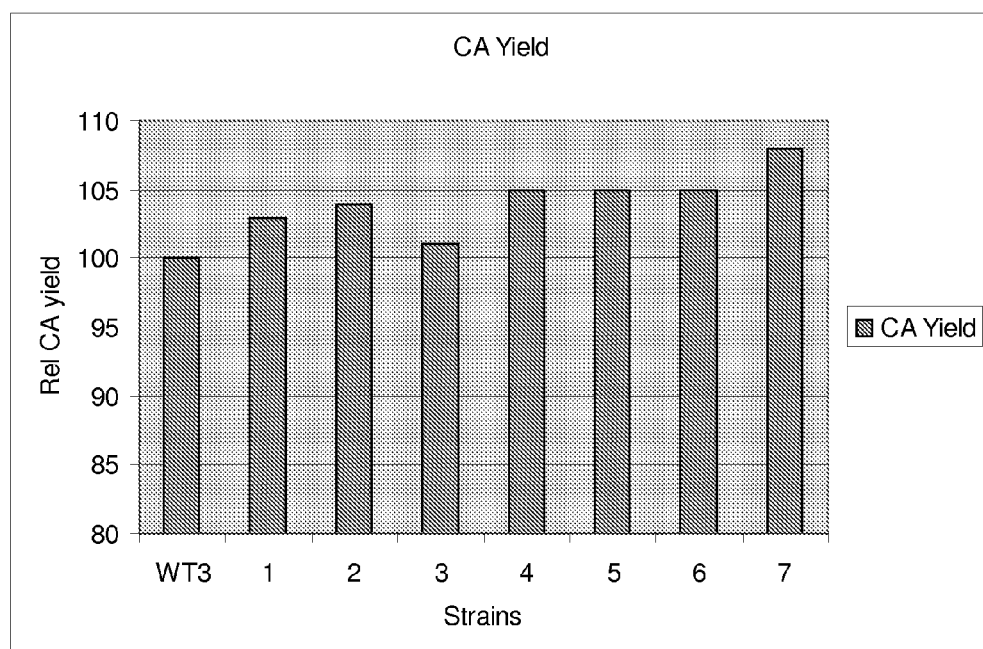

FIG. 8: Performance of overexpression strains in submerged fermentation.

Indicated are the strains of Table 2, fermented as described in Example 5. Performance of the various strains is depicted as the yield of citric acid production compared to the yield of the WT3 strain, which was set at 100%.

Figure 9:
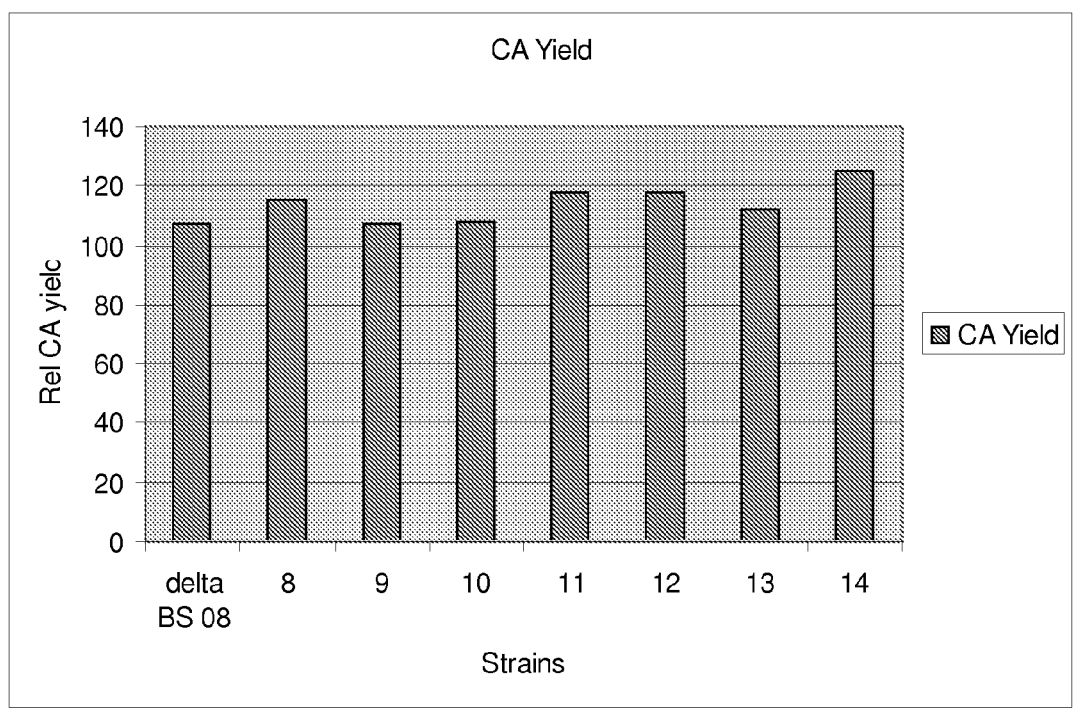

FIG. 9: Performance of overexpression strains in a BS08 disrupted background in submerged fermentation.

Indicated are the strains of Table 2, fermented as described in Example 5. Performance of the various strains is depicted as the yield of citric acid production compared to the yield of the WT3 strain, which was set at 100%.

DETAILED DESCRIPTION OF THE INVENTION

Surprisingly, it has now been found that proteins encoded by polynucleotides having a nucleotide sequence that hybridizes preferably under highly stringent conditions to TS08, TS09, CS07 and BS08 nucleotide sequences selected from the group of SEQ ID NO's: 1, 6, 11 and 16, respectively, play an important role in the biotechnological production of citric acid. It has also been found, that by genetically altering the expression level of nucleotides according to the invention in a microorganism, such as for example *Aspergillus*, the efficiency of said citric acid production within said microorganism can be even greatly improved leading e.g. to higher production and/or yield of citric acid.

Consequently, the invention relates to a TS08, TS09, CS07 and/or BS08 polynucleotide selected from the group consisting of:

(a) polynucleotides encoding a TS08, TS09, CS07 or BS08 polypeptide comprising an amino acid sequence selected from the group of SEQ ID NO's: 2, 7, 12 and 17, respectively;

(b) polynucleotides comprising the nucleotide sequence selected from the group of SEQ ID NO's: 1, 6, 11 and 16;

(c) polynucleotides comprising a nucleotide sequence obtainable by nucleic acid amplification such as polymerase chain reaction, using genomic DNA from a microorganism as a template and a primer set selected from the group of SEQ ID NO: 3 and SEQ ID NO:4, SEQ ID NO:8 and SEQ ID NO:9, SEQ ID NO:13 and SEQ ID NO:14, or SEQ ID NO:18 and SEQ ID NO:19, respectively;

(d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the activity of a TS08, TS09, CS07 or BS08 polypeptide;

(e) polynucleotides the complementary strand of which hybridizes under stringent conditions to a polynucleotide as defined in any one of (a) to (d) and which encode a TS08, TS09, CS07 or BS08 polypeptide;

(f) polynucleotides which are at least 70%, such as 75, 80, 85, 90, 91, 92, 93, 94, 95, 96, 97, 98 or 99% homologous to a polynucleotide as defined in any one of (a) to (d) and which encode a TS08, TS09, CS07 or BS08 polypeptide, or the complementary strand of such a polynucleotide.

In a preferred embodiment of the invention, the invention relates to a TS08 and/or TS09 polynucleotide is selected from the group consisting of:

(a) polynucleotides encoding a TS08 or TS09 polypeptide comprising an amino acid sequence according to SEQ ID NO: 2 or SEQ ID NO: 7, respectively;

(b) polynucleotides comprising a nucleotide sequence according to SEQ ID NO: 1 or SEQ ID NO: 6;

(c) polynucleotides comprising a nucleotide sequence obtainable by nucleic acid amplification such as polymerase chain reaction, using genomic DNA from a microorganism as a template and a primer set according to SEQ ID NO:3 and SEQ ID NO:4, or SEQ ID NO:8 and SEQ ID NO:9, respectively;

(d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the activity of a TS08 or TS09 polypeptide;

(e) polynucleotides the complementary strand of which hybridizes under stringent conditions to a polynucleotide as defined in any one of (a) to (d) and which encode a TS08 or TS09 polypeptide;

(f) polynucleotides which are at least 70%, such as 75, 80, 85, 90, 91, 92, 93, 94, 95, 96, 97, 98 or 99% homologous to a polynucleotide as defined in any one of (a) to (d) and which encode a TS08 or TS09 polypeptide or the complementary strand of such a polynucleotide.

The TS, CS and BS proteins as isolated from *Aspergillus niger* CBS 513.88 shown in SEQ ID NO's: 2, 7, 12 and 17 and described herein were found to be particularly useful TS proteins, since it appeared that they perform a crucial function in the citric acid production in microorganisms, in particular in fungi, such as *Aspergillus*. Accordingly, the invention relates to a polynucleotide encoding a polypeptide selected from the group of SEQ ID NO's: 2, 7, 12 and 17. The protein may be encoded by a nucleotide sequence selected from the group of SEQ ID NO's: 1, 6, 11 and 16, respectively. The invention therefore also relates to polynucleotides comprising the nucleotide sequence selected from the group of SEQ ID NO's: 1, 6, 11 and 16. The corresponding cDNA's are shown in SEQ ID NO's: 5, 10, 15 and 20, respectively.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). From the searches, the TS08 polynucleotide according to SEQ ID NO:1 was annotated as encoding a protein having manganese resistance protein 1 activity. The TS09 polynucleotide according to SEQ ID NO:6 was annotated as encoding a protein having transport activity for iron and manganese. The CS07 polynucleotide according to SEQ ID NO:11 was annotated as encoding a protein having citrate synthase activity. Improvement of citric acid production can be expected from enhanced expression of a CS and/or TS gene and increased or improved activity of a TS and/or CS polypeptide.

The BS08 polynucleotide according to SEQ ID NO:16 was annotated as encoding a protein having mitochondrial superoxide dismutase MnSOD activity. Improvement of Citric acid production can be expected from the down regulation/disruption of the MnSOD gene, encoding the manganese-dependent mitochondrial superoxide dismutase. Disruption of MnSOD would cause impairment of degradation of the formed superoxide ion-radicals. The "damage" caused by the superoxide to proteins, lipids and nucleic acids, can explain many pleiotropic effects of Mn-deficiency in *A. niger* giving rise to accumulation of citric acid.

A nucleic acid encoding a TS08, TS09, CS07 or BS08 polypeptide according to SEQ ID No's: 2, 7, 12 and 17, respectively, may be obtained by nucleic acid amplification using cDNA, mRNA or alternatively, genomic DNA, as a template and appropriate oligonucleotide primers such as the nucleotide primer sets according to SEQ ID NO:3 and SEQ ID NO:4, SEQ ID NO:8 and SEQ ID NO:9, SEQ ID NO:13 and SEQ ID NO:14, SEQ ID NO:18 and SEQ ID NO:19, respectively, according to standard PCR amplification techniques. Preferably, a primer set according to SEQ ID NO:3 and SEQ ID NO:4, or SEQ ID NO:8 and SEQ ID NO:9 is utilized to obtain a nucleic acid encoding a TS polypeptide, preferably a TS08 or TS09 polypeptide according to SEQ ID No's: 2 and 7, respectively. The nucleic acid thus amplified may be cloned into an appropriate vector and characterized by DNA sequence analysis. Additionally, the nucleic acid may be obtained through synthetic construction of the nucleic acid.

An overview of SEQ ID NO's of the DNA, polypeptides, coding sequences and nucleotide primers of the present invention is presented in Table 1. The terms "polynucleotide" and "nucleic acid" as used herein are intended to depict a DNA or coding sequence. Consequently, e.g. the term "a TS08 polynucleotide" inter alia encompasses a TS08 DNA according to SEQ ID NO: 1 and a TS08 coding sequence according to SEQ ID NO: 5, but not a TS08 Forward/Reverse primer according to SEQ ID NO's: 3 and 4. Likewise, the terms "polypeptide" or "protein" as used herein are intended to depict a protein or polypeptide sequence. Consequently, e.g. the term "a TS08 polypeptide" inter alia encompasses a TS08 polypeptide according to SEQ ID NO: 2.

TABLE 1

Overview of SEQ ID NO's of the DNA, polypeptides, coding sequences and nucleotide primers of the present invention.

|  | TS08 | TS09 | CS07 | SB 08 |
| --- | --- | --- | --- | --- |
| DNA | SEQ ID NO: 1 | SEQ ID NO: 6 | SEQ ID NO: 11 | SEQ ID NO: 16 |
| Polypeptide | SEQ ID NO: 2 | SEQ ID NO: 7 | SEQ ID NO: 12 | SEQ ID NO: 17 |
| Forward primer | SEQ ID NO: 3 | SEQ ID NO: 8 | SEQ ID NO: 13 | SEQ ID NO: 18 |
| Reverse primer | SEQ ID NO: 4 | SEQ ID NO: 9 | SEQ ID NO: 14 | SEQ ID NO: 19 |
| Coding sequence | SEQ ID NO: 5 | SEQ ID NO: 10 | SEQ ID NO: 15 | SEQ ID NO: 20 |

The term "gene" as used herein refers to a polynucleotide which may be isolated from chromosomal DNA. Consequently, e.g. the term "a TS08 gene" inter alia encompasses a TS08 polynucleotide according to SEQ ID NO: 1.

The template for the reaction may be cDNA obtained by reverse transcription of mRNA prepared from strains known or suspected to comprise a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labelled and used to screen a bacteriophage or cosmid cDNA library. Alternatively, the labelled fragment may be used to screen a genomic library.

Accordingly, the invention relates to polynucleotides comprising a nucleotide sequence obtainable by nucleic acid amplification such as polymerase chain reaction, using DNA such as genomic DNA from a microorganism as a template and a primer set selected from the group of SEQ ID NO:3 and SEQ ID NO:4, SEQ ID NO:8 and SEQ ID NO:9, SEQ ID NO:13 and SEQ ID NO:14, SEQ ID NO:18 and SEQ ID NO:19, respectively. Preferably, a primer set according to SEQ ID NO:3 and SEQ ID NO:4, or SEQ ID NO:8 and SEQ ID NO:9 is utilized to respectively obtain a TS08 or TS09 polynucleotide of the invention.

The invention also relates to polynucleotides comprising a nucleotide sequence encoding a fragment or derivative of a CS07, BS08, TS08 or TS09 polypeptide encoded wherein in said derivative one or more amino acid residues are conservatively substituted compared to said polypeptide, and said fragment or derivative has the activity of a TS, CS or BS polypeptide, preferably a CS07, BS08, TS08 or TS09 polypeptide.

The invention also relates to polynucleotides the complementary strand of which hybridizes under stringent conditions to a polynucleotide as defined herein and which encode a TS, CS or BS polypeptide, preferably a CS07, BS08, TS08 or TS09 polypeptide.

The invention also relates to polynucleotides which are at least 70% homologous to a polynucleotide as defined herein and which encode a CS07, BS08, TS08 or TS09 polypeptide; and the invention also relates to polynucleotides being the complementary strand of a polynucleotide as defined herein above.

The invention also relates to primers, probes and fragments that may be used to amplify or detect a TS, CS and/or BS polynucleotide according to the invention and to identify related species or families of microorganisms also carrying such genes.

The present invention also relates to vectors which include polynucleotides of the invention. Accordingly, the present invention relates to vectors comprising a TS08, TS09, CS07 and/or BS08 polynucleotide, preferably a TS08 and/or a TS09 polynucleotide of the present invention and vectors containing a TS08, TS09, CS07 and/or BS08 polynucleotide, preferably a TS08 and/or a TS09 polynucleotide of the invention wherein said polynucleotide is operatively linked to expression control sequences allowing the expression in prokaryotic and eukaryotic cells.

The invention also relates to a microorganism which is genetically engineered with the TS08, TS09 and/or CS07 polynucleotides of the invention and/or with the vectors described immediately here above. These engineered microorganisms are designated: TS08, TS09, CS07, TS08/TS09, TS08/CS07, TS09/CS07 and TS08/TS09/CS07 microorganisms. In another embodiment, the aforementioned microorganisms are additionally genetically engineered with a polynucleotide comprising a polynucleotide for disruption or downregulation of a BS08 polynucleotide. These engineered microorganisms may be designated: TS08, TS09, CS07, TS08/TS09, TS08/CS07, TS09/CS07, TS08/TS09/CS07, deltaBS08-TS08, deltaBS08-TS09, deltaBS08-CS07, deltaBS08-TS08/TS09, deltaBS08-TS08/CS07, deltaBS08-TS09/CS07, and deltaBS08-TS08/TS09/CS07 microorganisms.

In a another embodiment in the aforementioned microorganisms, reduced production or activity of a BS08 polypeptide is obtained by modification or inactivation of a nucleic acid sequence present in the cell necessary for expression of the BS08 polynucleotide.

The invention also relates to the genetically engineered microorganisms TS08, TS09, CS07, TS08/TS09, TS08/CS07, TS09/CS07, TS08/TS09/CS07, deltaBS08-TS08, deltaBS08-TS09, deltaBS08-CS07, deltaBS08-TS08/TS09, deltaBS08-TS08/CS07, deltaBS08-TS09/CS07, and deltaBS08-TS08/TS09/CS07, wherein optionally reduced production or activity of a BS08 polypeptide is obtained by modification or inactivation of a nucleic acid sequence present in the cell necessary for expression of the BS08 polynucleotide, said microorganisms capable of producing citric acid from sucrose in a quantities of 100 g/l or more.

The invention also relates to processes for producing microorganisms capable of expressing a polypeptide encoded by the above defined polynucleotide and a polypeptide encoded by a polynucleotide as defined above. Accordingly, the invention relates to a process for producing cells capable of expressing a TS08, TS09, CS07, TS08/TS09, TS08/CS07, TS09/CS07, or a TS08/TS09/CS07 polypeptide comprising the step of genetically engineering cells with a TS08, TS09 and/or CS07 polynucleotide of the invention or a vector comprising a TS08, TS09 and/or CS07 polynucleotide of the invention. Preferably, the process comprises genetically engineering cells with a polynucleotide encoding a TS08, TS09 and/or CS07 polypeptide, which polynucleotide may be comprised in a vector.

In another embodiment, the process to produce the cells capable of expressing a TS08, TS09, CS07, TS08/TS09, TS08/CS07, TS09/CS07, or a TS08/TS09/CS07 polypeptide described here above, additionally comprises genetically engineering the cells with a polynucleotide comprising a polynucleotide for disruption or downregulation of a BS08 polynucleotide.

The invention also relates to the use of the TS08, TS09, CS07, TS08/TS09, TS08/CS07, TS09/CS07, or TS08/TS09/CS07 polynucleotides defined above, for the production of citric acid from a carbohydrate.

In preferred embodiment, the use of the TS08, TS09, CS07, TS08/TS09, TS08/CS07, TS09/CS07, or TS08/TS09/CS07 polynucleotides for the production of citric acid as described here above is combined with the use of a polynucleotide comprising a polynucleotide for disruption or downregulation of a BS08 polynucleotide.

In another embodiment, the TS08, TS09 or CS07 polynucleotide is operatively linked to expression control sequences and transferred into a microorganism. More preferably, the expression control sequences comprise a regulation- and/or promoter, and/or terminator sequence, wherein at least one of these sequences is altered in such a way that it leads to an improved yield and/or efficiency of production of citric acid from a carbohydrate produced by said microorganism. Even more preferably, said expression control sequences are altered in such a way that it leads to increased and/or improved activity of the respective encoding TS08, TS09 and/or CS07 polypeptide.

Preferably, the carbohydrate used for the production of citric acid is preferably a carbohydrate selected from the group consisting of glucose, fructose, sucrose, molasses, starch, corn, cassaya and polyalcohols.

The invention also relates to microorganisms wherein the activity of a TS and/or CS polypeptide, preferably a TS08, TS09, CS07, TS08/TS09, TS08/CS07, TS09/CS07, or TS08/TS09/CS07 polypeptide, such as the polypeptides according to SEQ ID NO's: 2, 7 and 12 respectively, is enhanced and/or improved so that the yield of citric acid which is produced from a carbohydrate is increased. Preferably, the yield of citric acid produced by a microorganism comprising a polypeptide with enhanced and/or improved activity as described above is increased by at least 1%, 2%, 3% 4%, 8%, 10%, 15%, 20%, 30%, 40%, 50%, 100%, 200%, 500% or more compared to the amount of citric acid produced by the parental microorganism. This may be accomplished, for example, by transferring a polynucleotide according to the invention into a recombinant or non-recombinant microorganism that may or may not contain an endogenous equivalent of a CS07, BS08, TS08 and/or TS09 gene.

The invention also relates to microorganisms wherein the activity of a TS and/or CS polypeptide, preferably a TS08, TS09, CS07, TS08/TS09, TS08/CS07, TS09/CS07, or TS08/TS09/CS07 polypeptide, such as the polypeptides according to SEQ ID NO's: 2, 7 and 12 respectively, is enhanced and/or improved and the activity of a BS08 protein, such as the polypeptide according to SEQ ID NO: 17, is decreased or abolished so that the yield of citric acid which is produced from a carbohydrate is increased. Preferably, the yield of citric acid produced by a microorganism comprising a polypeptide with enhanced and/or improved activity as described above is increased by at least 1%, 2%, 3% 4%, 8%, 10%, 15%, 20%, 30%, 40%, 50%, 100%, 200%, 500% or more compared to the amount of citric acid produced by the parental microorganism.

Accordingly, the invention relates to a process for the production of an enhanced endogenous TS08, TS09 or TS08/TS09 gene in a microorganism, said microorganism comprising a polynucleotide encoding a TS08 or TS09 polypeptide such as the TS08 or TS09 polypeptide according to SEQ ID NO's: 2 and 7, respectively, said process comprising the step of altering said polynucleotide in such a way that it leads to an improved yield and/or efficiency of production of citric acid produced from a carbohydrate by said microorganism.

In another embodiment, additionally in the microorganism with enhanced endogenous TS08, TS09 or TS08/TS09 gene described here above, a CS07 gene is enhanced by altering a polynucleotide comprising a polynucleotide encoding a CS07 polypeptide, such as the CS07 polypeptide according to SEQ ID NO: 12, contained within said microorganism.

In yet another embodiment, additionally in the microorganism with enhanced TS08, TS09, CS07, TS08/TS09, TS08/CS07, TS09/CS07, or TS08/TS09/CS07 described here above, an endogenous BS08 gene is disrupted and/or downregulated by altering a polynucleotide encoding a BS08 polypeptide such as the polypeptide according to SEQ ID NO: 17, contained within said microorganism.

In yet another embodiment, additionally in the microorganism with enhanced TS08, TS09, CS07, TS08/TS09, TS08/CS07, TS09/CS07, or TS08/TS09/CS07, or with enhanced TS08, TS09, CS07, TS08/TS09, TS08/CS07, TS09/CS07, or TS08/TS09/CS07, combined with a disrupted of downregulated BS08 gene, reduced expression of an endogenous BS08 gene is obtained by modification or inactivation of a polynucleotide sequence, preferably a control sequence, required for the expression of the BS08 gene.

In yet another embodiment, the invention relates to a process for the production of a TS08, TS09, CS07, TS08/TS09, TS08/CS07, TS09/CS07, or a TS08/TS09/CS07 polypeptide in a microorganism, comprising the step of altering said microorganism so that the microorganism produces said polypeptide with increased and/or improved TS08, TS09, CS07, TS08/TS09, TS08/CS07, TS09/CS07, or a TS08/TS09/CS07 activity, optionally combined with decreased or abolished BS08 activity leading to an improved yield and/or efficiency of production of citric acid produced from a carbohydrate by said microorganism.

In yet another embodiment, the invention relates to a process for the production of a microorganism capable of producing citric acid, comprising the step of altering said microorganism so that the microorganism produces a polypeptide with increased and/or improved TS08, TS09, CS07, TS08/TS09, TS08/CS07, TS09/CS07, or a TS08/TS09/CS07 activity, optionally combined with decreased or abolished BS08 activity, leading to an improved yield and/or efficiency of production of citric acid produced from a carbohydrate by said microorganism.

In yet another embodiment, the invention relates to a process for the production of a microorganism containing at least one endogenous gene comprising a polynucleotide of the invention, preferably a polynucleotide encoding a TS08, TS09 or CS07 polypeptide, comprising the step of altering said microorganism so that the at least one endogenous gene is overexpressed, leading to an improved yield and/or efficiency of citric acid produced from a carbohydrate by said microorganism.

In a preferred embodiment, the process additionally comprises the step of altering the microorganism so that an endogenous gene comprising a polynucleotide encoding a BS08 polypeptide is downregulated or disrupted.

The skilled person will know how to enhance and/or improve the activity of a TS and/or CS protein, preferably a TS08, TS09, CS07, TS08/TS09, TS08/CS07, TS09/CS07, or a TS08/TS09/CS07 protein. Such may be for instance accomplished by genetically modifying the host organism in such a way that it produces more or more stable copies of the TS and/or CS protein, preferably the TS08, TS09, CS07, TS08/TS09, TS08/CS07, TS09/CS07, or a TS08/TS09/CS07 protein, than the wild type organism or by increasing the specific activity of the TS and/or CS protein, preferably the TS08, TS09, CS07, TS08/TS09, TS08/CS07, TS09/CS07, or a TS08/TS09/CS07 protein.

The skilled person will understand that both recombinant and classical genetic techniques can be used to mutate, modify, enhance or overexpress a TS and/or CS gene to result in increased expression and/or improved activity of the gene or of the multiple genes.

Likewise, the skilled person will know how to reduce or abolish the activity of a BS protein, preferably a BS08 protein. Such may be for instance accomplished by genetically modifying the host organism in such a way that it produces less or no copies of the BS protein, preferably the BS08 protein, than the wild type organism or by decreasing or abolishing the specific activity of the BS protein, preferably the BS08 protein. Likewise, the skilled person will understand that both recombinant and classical genetic techniques can be used to decrease or abolish the specific activity of a BS protein. Moreover, the skilled person will understand that both recombinant and classical genetic techniques can be used to mutate, disrupt, delete, modify or inactivate a gene, preferably a BS08 gene to result in decreased expression of a gene or multiple genes.

Additionally, a microorganism comprising combinations of various upregulated and downregulated genes, such as may be obtained by combinations of recombinant and classical mutagenesis techniques. For example, overexpression of a TS08, TS09, CS07, TS08/TS09, TS08/CS07, TS09/CS07, or a TS08/TS09/CS07 polynucleotide may be attained by recombinant methods; subsequently an endogenous BS08 polynucleotide may be downregulated using classical mutagenesis. According to another example, the endogenous BS08 polynucleotide may be downregulated or disrupted by classical mutagenesis, followed by recombinant overexpression of a TS08, TS09, CS07, TS08/TS09, TS08/CS07, TS09/CS07, or a TS08/TS09/CS07 polynucleotide. Other combinations of classical and recombinant techniques are also anticipated by the current invention.

In the following description, procedures are detailed to achieve the increase in the yield and/or production of citric acid which is which is produced from a carbohydrate by increasing the activity of a TS08, TS09, CS07, TS08/TS09, TS08/CS07, TS09/CS07, or a TS08/TS09/CS07 protein. These procedures apply mutatis mutandis for other TS and/or CS proteins.

Modifications in order to have the organism produce more copies of the TS08, TS09, CS07, TS08/TS09, TS08/CS07, TS09/CS07, or a TS08/TS09/CS07 genes and/or protein may include the use of a strong promoter, or the mutation (e.g. insertion, deletion or point mutation) of (parts of) the TS08, TS09, CS07, TS08/TS09, TS08/CS07, TS09/CS07, or a TS08/TS09/CS07 gene or its regulatory elements. It may also involve the insertion of multiple copies of the gene into a suitable microorganism. An increase in the specific activity of a TS08, TS09, CS07, TS08/TS09, TS08/CS07, TS09/CS07, or a TS08/TS09/CS07 protein may also be accomplished by methods known in the art. Such methods may include the mutation (e.g. insertion, deletion or point mutation) of (parts of) the TS08, TS09, CS07, TS08/TS09, TS08/CS07, TS09/CS07, or a TS08/TS09/CS07 gene(s).

Examples of a physical or chemical mutagenizing agent suitable for the classical mutagenesis include gamma or ultraviolet (UV) radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogs. When such agents are used, the mutagenesis is typically performed by incubating the parent cell to be mutagenized in the presence of the mutagenizing agent of choice under suitable conditions, and selecting for mutant cells exhibiting reduced expression of the gene.

Also known in the art are methods of increasing the activity of a given protein by contacting the TS08, TS09, CS07, TS08/TS09, TS08/CS07, TS09/CS07, or a TS08/TS09/CS07 protein with specific enhancers or other substances that specifically interact with the TS08, TS09, CS07, TS08/TS09, TS08/CS07, TS09/CS07, or a TS08/TS09/CS07 protein. In order to identify such specific enhancers, the TS08, TS09, CS07, TS08/TS09, TS08/CS07, TS09/CS07, or a TS08/TS09/CS07 protein may be expressed and tested for activity in the presence of compounds suspected to enhance the activity of the respective TS08, TS09, CS07, TS08/TS09, TS08/CS07, TS09/CS07, or a TS08/TS09/CS07 protein. The activity of the TS08, TS09, CS07, TS08/TS09, TS08/CS07, TS09/CS07, or a TS08/TS09/CS07 protein may also be increased by stabilizing the messenger RNA encoding the TS08, TS09, CS07, TS08/TS09, TS08/CS07, TS09/CS07, or a TS08/TS09/CS07 protein, respectively. Such methods are also known in the art, see for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

In the following description, procedures are detailed to achieve the increase in the yield and/or production of citric acid which is produced from a carbohydrate by reducing or abolishing the activity of a BS08 protein. These procedures apply mutatis mutandis for other BS proteins.

Modifications in order to have the organism produce less or no copies of the BS08 gene and/or protein may include the use of a weak promoter, or the mutation (e.g. insertion, deletion or point mutation) of (parts of) the BS08 gene or its regulatory elements. Decreasing or abolishing the specific activity of a BS08 protein may also be accomplished by methods known in the art. Such methods may include the mutation (e.g. insertion, deletion or point mutation) of (parts of) the BS08 gene.

Also known in the art are methods of reducing or abolishing the activity of a given protein by contacting the BS08 protein with specific inhibitors or other substances that specifically interact with the BS08 protein. In order to identify such specific inhibitors, the BS08 protein may be expressed and tested for activity in the presence of compounds suspected to inhibit the activity of the BS08 protein. Potential inhibiting compounds may for instance be monoclonal or polyclonal antibodies against the BS08 protein. Such antibodies may be obtained by routine immunization protocols of suitable laboratory animals.

The invention may be performed in any microorganism carrying a TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or a TS08/TS09/CS07/BS08 gene or homologue thereof. Suitable microorganisms may be selected from fungi, in particular filamentous fungi, or yeast either as wild type strains, mutant strains derived by classic mutagenesis and selection methods or as recombinant strains. "Filamentous fungi" include all filamentous forms of the subdivision Eumycota and Oomycota (as defined by Hawksworth et al., 1995, supra). Examples of such microorganisms include but are not limited to *Aspergillus, Acremonium, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma*. Preferred microorganisms of the invention are selected from the group of filamentous fungi, preferably from *Aspergillus*, more preferably from *A. niger, A. awamori, A. aculeatus, A. japonicus, A. oryzae, A. vadensis, A. carbonarius, A. tubingensis, A. lacticoffeatus, A. brasiliensis, A. piperis A. costaricaensis* or *A. foetidus*, even more preferably *A. foetidus* var *acidus* or *A. foetidus* var *pallidus*, even more preferably from *A. niger* var *awamori*, even more preferably from *A. niger* ATCC1015 and most preferably from *A. niger* CBS 513.88. A microorganism as of the present invention may carry further modifications either on the DNA or protein level (see above), as long as such modification has a direct impact on the yield, production and/or efficiency of the production of citric acid. As such, a microorganism of the present invention may carry further modifications resulting in improved citric acid productivity by a combination of classical mutagenesis and molecular biology. Such further modifications may for instance affect other genes encoding TS proteins such as e.g. ion or sugar transporters, BS genes that are involved in so-called "by-pass routes" such as e.g. oxaloacetate hydrolases, glucose oxidase and/or glycolate (oxido-) reductases, CS genes encoding proteins that are involved in citrate biosynthesis such as e.g. citrate synthases, aconitases, genes encoding proteins that are involved in the respiratory system such as e.g. mitochondrial proton-pumping NADH: ubiquinone reductase or oxidases, 6-phosphofructokinase pfkA, or mutations in the cytochrome-dependent respiratory enzymes or alternative respiratory pathway. Methods of performing such modifications are known in the art, with some examples further described herein.

In one embodiment, the present invention is related to a modified microorganism wherein the activity of a TS08, TS09, CS07, TS08/TS09, TS08/CS07, TS09/CS07, or a TS08/TS09/CS07 polypeptide, is enhanced and/or improved and optionally, the activity of a BS protein, preferably a BS08 protein, is decreased or abolished so that the yield of citric acid which is produced from a carbohydrate is increased combined with a further modification as defined above, in particular carrying a further deficiency in the gene encoding oxaloacetate hydrolase, such as described in e.g. WO 04/070022, useful for the production of citric acid.

In accordance with a further object of the present invention there is provided the use of a polynucleotide as defined above or a microorganism which is genetically engineered using such polynucleotides in the production of citric acid.

The invention also relates to processes for the expression of endogenous genes in a microorganism, to processes for the production of polypeptides as defined above in a microorganism and to processes for the production of microorganisms capable of producing citric acid. All these processes may comprise the step of altering a microorganism, wherein "altering" as used herein encompasses the process for "genetically altering" or "altering the composition of the cell culture media and/or methods used for culturing" in such a way that the yield and/or productivity of the fermentation product can be improved compared to the wild-type organism.

In accordance with still another aspect of the invention there is provided a process for the production of citric acid by fermentation. Accordingly, there is provided a process for the production of citric acid from a carbohydrate wherein a microorganism of the invention as described here above is cultivated in an aqueous nutrient medium under conditions that allow the production of citric acid from said carbohydrate and wherein citric acid is isolated as the fermentation product. In a preferred embodiment, there is provided a process for the production of citric acid with a microorganism obtainable from one of the methods of the invention wherein said microorganism is cultivated in an aqueous nutrient medium under conditions that allow the production of citric acid from a carbohydrate and wherein citric acid is isolated as the fermentation product. More preferably, the carbohydrate is selected from the group consisting of glucose, fructose, sucrose, molasses, starch, corn, cassaya and polyalcohols. The microorganisms of this embodiment comprise:

1) A microorganism which is genetically engineered with the TS08, TS09 and/or CS07 polynucleotides of the invention and/or with the vectors described immediately here above. These engineered microorganisms are designated: TS08, TS09, CS07, TS08/TS09, TS08/CS07, TS09/CS07 and TS08/TS09/CS07 microorganisms. Optionally, the aforementioned microorganisms are additionally genetically engineered with a polynucleotide comprising a polynucleotide for disruption or downregulation of a BS08 polynucleotide. These engineered microorganisms may be designated: TS08, TS09, CS07, TS08/TS09, TS08/CS07, TS09/CS07, TS08/TS09/CS07, deltaBS08-TS08, deltaBS08-TS09, deltaBS08-CS07, deltaBS08-TS08/TS09, deltaBS08-TS08/CS07, deltaBS08-TS09/CS07, and deltaBS08-TS08/TS09/CS07 microorganisms. Optionally, in the aforementioned microorganisms, reduced production or activity of a BS08 polypeptide is obtained by modification or inactivation of a nucleic acid sequence present in the cell necessary for expression of the BS08 polynucleotide.

2) The microorganism of (1) capable of producing citric acid from sucrose in quantities of 100 g/l or more.

3) A microorganism wherein the activity of a TS and/or CS polypeptide, preferably a TS08, TS09, CS07, TS08/TS09, TS08/CS07, TS09/CS07, or TS08/TS09/CS07 polypeptide, such as the polypeptides according to SEQ ID NO's: 2, 7 and 12 respectively, is enhanced and/or improved so that the yield of citric acid which is produced from a carbohydrate is increased. Preferably, the yield of citric acid produced by a microorganism comprising a polypeptide with enhanced and/or improved activity as described above is increased by at least 1%, 2%, 3% 4%, 8%, 10%, 15%, 20%, 30%, 40%, 50%, 100%, 200%, 500% or more compared to the amount of citric acid produced by the parental microorganism.

4) A microorganism wherein the activity of a TS and/or CS polypeptide, preferably a TS08, TS09, CS07, TS08/TS09, TS08/CS07, TS09/CS07, or TS08/TS09/CS07 polypeptide, such as the polypeptides according to SEQ ID NO's: 2, 7 and 12 respectively, is enhanced and/or improved and the activity of a BS08 protein, such as the polypeptide according to SEQ ID NO: 17, is decreased or abolished so that the yield of citric acid which is produced from a carbohydrate is increased. Preferably, the yield of citric acid produced by a microorganism comprising a polypeptide with enhanced and/or improved activity as described above is increased by at least 1%, 2%, 3% 4%, 8%, 10%, 15%, 20%, 30%, 40%, 50%, 100%, 200%, 500% or more compared to the amount of citric acid produced by the parental microorganism.

5) The microorganism of any one of (1) to (4), wherein the microorganism is selected from the group of filamentous fungi, preferably from *Aspergillus*, more preferably from *A. niger, A. awamori, A. aculeatus, A. japonicus, A. oryzae, A. vadensis, A. carbonarius, A. tubingensis, A. lacticoffeatus, A. brasiliensis, A. piperis A. costaricaensis* or *A. foetidus*, even more preferably *A. foetidus* var *acidus* or *A. foetidus* var *pallidus*, even more preferably from *A. niger* var *awamori*, even more preferably from *A. niger* ATCC1015 and most preferably from *A. niger* CBS 513.88.

Suitable carbohydrates that can be converted into citric acid may be for instance glucose or selected from carbon sources the assimilation of which results in the formation of glucose, such as e.g. sucrose, starch, corn, molasses, cassaya or polyalcohols. In case of molasses, beet or cane molasses may be used. The carbohydrates may be in liquefied form, such as for instance liquefied corn, starch or cassaya or it may be in the form of a syrup, such as for instance glucose, fructose, sucrose or molasses syrup. A combination of said substrates is also possible. Depending on the fermentation conditions and the used strains, the carbohydrates used as substrates may vary. In case of submerged fermentation, the preferred carbohydrate is selected from e.g. glucose, sucrose syrups or liquefied starches. In case of surface fermentation, the preferred carbohydrate is selected from e.g. molasses or sucrose syrup. Both submerged and surface fermentation are encompassed by the invention. An example of the industrial production of citric acid is described in U.S. Pat. No. 5,081, 025.

Conversion of the carbohydrate into citric acid in connection with the above process using a microorganism means that the conversion of the carbohydrate resulting in citric acid is performed by the microorganism, i.e. the substrate may be directly converted into citric acid. Said microorganism is cultured under conditions which allow such conversion from the carbohydrate as defined above. Microorganisms suitable for the production of citric acid from a given carbohydrate are capable of the conversion of said carbohydrate into the specified product, i.e. citric acid, by means of one or more biological conversion steps, without the need of any additional chemical conversion step.

A medium as used herein for the above process using a microorganism may be any suitable medium for the production of citric acid. Typically, the medium is an aqueous medium comprising for instance salts, substrate(s), and a certain pH.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable carbohydrates into the desired product such as citric acid. An example of such process for the production of citric acid is described in "Citric Acid", Max Roehr, Christian Kubicek, Jiri Kominek, in Biotechnology $2^{nd}$ Ed, Wiley VCH, 1997, pp 308-345 (as incorporated herein by reference). The fermentations are typically performed in batch, fed-batch or continuous mode.

The sequence of the genes comprising a nucleotide sequence selected from the group of SEQ ID NO's: 1, 6, 11 and 16, encoding a, TS08, TS09, CS07 or BS08 protein, respectively, was determined by sequencing a genomic clone obtained from *Aspergillus niger* CBS 513.88.

The invention also relates to a polynucleotide encoding at least a biologically active fragment or derivative of a TS08, TS09, CS07 and/or BS08 polypeptide according to SEQ ID NO's: 2, 7, 12 and 17, respectively.

As used herein, "biologically active fragment or derivative" means a polypeptide which retains essentially the same biological function or activity as a polypeptide selected from the group of SEQ ID NO's: 2, 7, 12 and 17. Examples of biological activity may for instance be enzymatic activity, signaling activity, transporter activity, or antibody reactivity activity. The term "biological function" or "functional equivalent" as used herein means that the protein has essentially the same biological activity, e.g. enzymatic, transporter, signaling or antibody reactivity activity, as a polypeptide selected from the group of SEQ ID NO's: 2, 7, 12 and 17.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide", "gene" and "recombinant gene" refer to nucleic acid molecules which may be isolated from chromosomal DNA, which include an open reading frame encoding a protein, e.g. *A. niger* CBS 513.88 TS, CS or BS proteins. A polynucleotide may include a polynucleotide sequence selected from the group of SEQ ID NO's: 1, 6, 11 and 16 or fragments thereof and regions upstream and downstream of the gene sequences which may include, for example, promoter regions, regulator regions and terminator regions important for the appropriate expression and stabilization of the polypeptide derived thereof.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of TS, CS or BS proteins may exist within a population, e.g., the *Aspergillus niger* population. Such genetic polymorphism in the CS07, BS08, TS08 or TS09 gene may exist among individuals within a population due to natural variation or in cells from different populations. Such natural variations can typically result in 1-5% variance in the nucleotide sequence of the CS07, BS08, TS08 or TS09 gene. Any and all such nucleotide variations and the resulting amino acid polymorphism in CS07, BS08, TS08 or TS09 are the result of natural variation and that do not alter the functional activity of TS proteins are intended to be within the scope of the invention.

As used herein, the terms "polynucleotide" or "nucleic acid molecule" or "nucleic acid" are interchangeable and are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

A polynucleotide of the invention may entirely or for a part be a synthetic polynucleotide. The codon use of the polynucleotide may be adapted for increased expression in a specific host. An example of a method to adapt codon use of a polynucleotide is described in WO 2006/077258.

The sequence information as provided herein should not be so narrowly construed as to require inclusion of erroneously identified bases. The specific sequences disclosed herein may be readily used to isolate the complete gene from a recombinant or non-recombinant microorganism capable of converting a carbohydrate into citric acid, in particular *Aspergillus niger*, preferably *Aspergillus niger* CBS 513.88 which in turn may easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequences shown in SEQ ID NO's: 1, 6, 11 or 16, for example a fragment which may be used as a probe or primer such as for instance SEQ ID NO's: 3, 4, 8, 9, 13, 14, 18 or 19, or a fragment encoding a portion of a protein according to the invention. The nucleotide sequence determined from the cloning of the TS08, TS09, CS07 or BS08 gene allows for the generation of probes and primers designed for use in identifying and/or cloning other TS08, TS09, CS07 or BS08 family members, as well as TS08, TS09, CS07 or BS08 homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence selected from the group of SEQ ID NO's: 1, 6, 11 or 16, or a fragment or derivative thereof.

A nucleic acid molecule encompassing all or a portion of a nucleic acid sequence selected from the group of SEQ ID NO's: 1, 6, 11 or 16 may be also isolated by the polymerase chain reaction (PCR) using synthetic oligonucleotide primers designed based upon the sequence information contained herein. Additionally, a nucleic acid molecule may be generated trough gene synthesis.

A nucleic acid of the invention may be amplified using cDNA, mRNA or alternatively, genomic DNA, as a template and appropriate oligonucleotide primers according to standard PCR amplification techniques. The nucleic acid thus amplified may be cloned into an appropriate vector and characterized by DNA sequence analysis.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, may be used as hybridization probes or polymerase chain reaction (PCR) primers. Uses of the nucleic acid molecules of the present invention that do not encode a polypeptide having a TS08, TS09, CS07 or BS08 activity include, inter alia, (1) isolating the gene encoding the protein of the present invention, or allelic variants thereof from a cDNA library, e.g., from other organisms than *Aspergillus niger* and (2) Northern blot analysis for detecting expression of mRNA of said protein in specific cells or (3) use in enhancing and/or improving the function or activity of homologous TS08, TS09, CS07 or BS08 genes in said other organisms.

Probes based on the nucleotide sequences provided herein may be used to detect transcripts or genomic sequences encoding the same or homologous proteins for instance in other organisms. Nucleic acid molecules corresponding to natural variants and non-*G. oxydans* homologues of the *A. niger* TS08, TS09, CS07 or BS08 DNA, which are also embraced by the present invention may be isolated based on their homology to the *A. niger* TS08, TS09, CS07 or BS08 nucleic acid disclosed herein using the *A. niger* DNA, or a portion thereof, as a hybridization probe according to standard hybridization techniques, preferably under highly stringent hybridization conditions.

In preferred embodiments, the probe further comprises a label group attached thereto, e.g., the label group can be a radioisotope, a fluorescent compound, an enzyme, or an enzyme cofactor.

Homologous gene sequences may be isolated, for example, by performing PCR using two degenerate oligonucleotide primer pools designed on the basis of nucleotide sequences as taught herein.

The template for the reaction may be cDNA obtained by reverse transcription of mRNA prepared from strains known or suspected to express a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

PCR technology can also be used to isolate full-length cDNA sequences from other organisms. For example, RNA may be isolated, following standard procedures, from an appropriate cellular or tissue source. A reverse transcription reaction may be performed on the RNA using an oligonucleotide primer specific for the most 5'-end of the amplified fragment for the priming of first strand synthesis.

The resulting RNA/DNA hybrid may then be "tailed" (e.g., with guanines) using a standard terminal transferase reaction, the hybrid may be digested with RNaseH, and second strand synthesis may then be primed (e.g., with a poly-C primer). Thus, cDNA sequences upstream of the amplified fragment may easily be isolated. For a review of useful cloning strategies, see e.g., Sambrook et al., supra; and Ausubel et al., supra.

Also, nucleic acids encoding other TS08, TS09, CS07 or BS08 family members, which thus have a nucleotide sequence that differs from the respective nucleotide sequence according to SEQ ID NO's: 1, 6, 11 or 16, are within the scope of the invention. Moreover, nucleic acids encoding TS08, TS09, CS07 or BS08 proteins from different species which thus may have a nucleotide sequence which differs from the respective nucleotide sequence according to SEQ ID NO's: 1, 6, 11 or 16 are within the scope of the invention.

The invention also relates to an isolated polynucleotide hybridisable under stringent conditions, preferably under highly stringent conditions, to a polynucleotide as of the present invention, such as for instance a polynucleotide according to SEQ ID NO's: 1, 6, 11 or 16. Advantageously, such polynucleotide may be obtained from a microorganism capable of converting a carbohydrate into citric acid, in particular *Aspergillus niger*, preferably *Aspergillus niger* CBS 513.88.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence selected from the group of SEQ ID NO's: 1, 6, 11 or 16, or a complement thereof.

A preferred, non-limiting example of such hybridization conditions are hybridization in 6× sodium chloride/sodium citrate (SSC) at about 45° c., followed by one or more washes in 1×SSC, 0.1% SDS at 50° C., preferably at 55° C., more preferably at 60° C. and even more preferably at 65° C.

Highly stringent conditions include, for example, hybridizing at 68° C. in 6×SSC/5×Denhardt's solution/1.0% SDS and washing in 0.2×SSC/0.1% SDS at room temperature. Alternatively, washing may be performed at 42° C., 50° C., 60° C., 65° C. or alternatively 68° C. for very high stringency.

"Stringency" of hybridization reactions is readily determinable by one of ordinary skill in the art. For additional details and explanation of stringency of hybridization reactions, see Ausubel et al., Current Protocols in Molecular Biology, Wiley Interscience Publishers, (1995).

Preferably, an isolated nucleic acid molecule of the invention that hybridizes under preferably highly stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *A. niger* TS08, TS09, CS07 or BS08 protein.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, genomic DNA or cDNA libraries constructed from other organisms, e.g. microorganisms capable of converting a carbohydrate into citric acid, in particular other *Aspergillus* species may be screened.

For example, *Aspergillus* strains may be screened for homologous polynucleotides by Northern blot analysis. Upon detection of transcripts homologous to polynucleotides according to the invention, DNA libraries may be constructed from RNA isolated from the appropriate strain, utilizing standard techniques well known to those of skill in the art. Alternatively, a total genomic DNA library may be screened using a probe hybridisable to a polynucleotide according to the invention.

A nucleic acid molecule of the present invention, such as for instance a nucleic acid molecule selected from the group of SEQ ID NO's: 1, 6, 11 or 16, or a fragment or derivative thereof, may be isolated using standard molecular biology techniques and the sequence information provided herein. For example, using all or portion of a nucleic acid sequence selected from the group of SEQ ID NO's: 1, 6, 11 or 16 as a hybridization probe, nucleic acid molecules according to the invention may be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at http://www.accelrys.com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.accelrys.com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available at http://vega.igh.cnrs.fr/bin/align-guess.cgi) using a PAM120 weight residue table, a gap length penalty of 12 and a gap penalty of 4. In yet another embodiment, the percent identity between two nucleotide sequences is determined using the CDA program (Huang, 1994, A Context Dependent Method for Comparing Sequences, Proceedings of the 5th Symposium on Combinatorial Pattern Matching, Lecture Notes in Computer Science 807, Springer-Verlag, 54-63) with the parameters set as follows: (i) for (poly)peptide alignments: Mismatch:-2 GapOpen:11 GapExtend:1 ContextLength:10 MatchBonus:1, and (ii) for nucleotide sequence alignments Mismatch:-15 GapOpen:5 GapExtend:2 ContextLength:10 Match Bonus:1.

Examples of alternative programs used for alignments and determination of homology are Clustal method (Higgins, 1989, CABIOS 5: 151-153) or Clustal W (Thompson J D, Higgins D G, and Gibson T J (1994)—CLUSTAL W: improving the sensitivity of progressive multiple sequence alignment through sequence weighting, positions-specific gap penalties and weight matrix choice. Nucleic Acids Research 22:4673-4680).

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=11 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. See httpcolonbackslashbackslashwwwdotncbidotnlmdotnihdotgov.

In another preferred embodiment, an isolated nucleic acid molecule of the invention comprises a nucleic acid molecule which is the complement of a nucleotide sequence of the present invention, such as for instance a sequence selected from the group of SEQ ID NO's: 1, 6, 11 or 16. A nucleic acid molecule, which is complementary to a nucleotide sequence disclosed herein, is one that is sufficiently complementary to a nucleotide sequence selected from the group of SEQ ID NO's: 1, 6, 11 or 16 such that it may hybridize to said nucleotide sequence thereby forming a stable duplex.

In a further preferred embodiment, a nucleic acid of the invention selected from the group of SEQ ID NO's: 1, 6, 11 or 16, or the complement thereof contains at least one mutation leading to a gene product with modified function/activity. The at least one mutation may be introduced by methods described herein. In one aspect, the at least one mutation leads to a respective TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein whose function and/or activity compared to the wild type counterpart is enhanced or improved. Methods for introducing such mutations are well known in the art.

The term "increase" of activity as used herein encompasses increasing activity of one or more polypeptides in the producing organism, which in turn are encoded by the corresponding polynucleotides described herein. There are a number of methods available in the art to accomplish increase of activity of a given protein, in this case the TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein. In general, the specific activity of a protein may be increased or the copy number of the protein may be increased. The term increase of activity or equivalent expressions also encompasses the situation wherein TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein activity is introduced in a cell that did not contain this activity before, e.g. by introducing a gene encoding TS08, TS09, CS07, TS08/TS09, TS08/CS07, TS09/CS07, TS08/TS09/CS07, TS08/BS08, TS09/BS08, CS07/BS08, TS09/BS08, TS08/CS07/BS08, TS09/CS07/BS08, or TS08/TS09/CS07/BS08 in a cell that did not contain an equivalent of this gene(s) before, or that could not express an active form of the corresponding protein before. To facilitate such an increase, the copy number of the genes corresponding to the polynucleotides described herein may be increased. Alternatively, a strong promoter may be used to direct the expression of the polynucleotide. In another embodiment, the promoter, regulatory region and/or the ribosome binding site upstream of the gene can be altered to increase the expression. The expression may also be enhanced or increased by increasing the relative half-life of the messenger RNA. In another embodiment, the activity of the polypeptide itself may be increased by employing one or more mutations in the polypeptide amino acid sequence, which increases the activity. For example, altering the affinity of the polypeptide for its corresponding substrate may result in improved activity. Likewise, the relative half-life of the polypeptide may be increased. In either scenario, that being enhanced gene expression or increased specific activity, the improvement may be achieved by altering the composition of the cell culture media and/or methods used for culturing. "Enhanced expression" or "improved activity" as used herein means an increase of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are enhanced and/or improved. The activity of the TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein may also be enhanced by contacting the protein with a specific or general enhancer of its activity.

In a further embodiment, in addition to enhanced and/or improved activity of a TS08, TS09, CS07, TS08/TS09, TS08/CS07, TS09/CS07, or TS08/TS09/CS07 protein, a BS08 encoding nucleic acid of the invention such as shown in SEQ ID NO:16 or the complement thereof contains at least one mutation leading to a gene product with modified function/activity, preferably reduced activity. The (at least) one mutation(s) may be introduced by methods described herein. In one aspect, the (at least) one mutation(s) leads to a BS08 protein whose function compared to the wild type counterpart is completely or partially destroyed. Methods for introducing such mutations are well known in the art.

The term "reduction" of activity as used herein encompasses decreasing activity of one or more polypeptides in the producing organism, which in turn are encoded by the corresponding polynucleotides described herein. There are a number of methods available in the art to accomplish reduction of activity of a given protein, in this case the BS08 protein. In general, the specific activity of a protein may be decreased or the copy number of the protein may be decreased.

To facilitate such a decrease, the copy number of the genes corresponding to the polynucleotides described herein may be decreased. This decrease could include the disruption, modification or inactivation of the genes corresponding to the polynucleotides described herein. Modification or inactivation of the gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. An example of expressing an antisense-RNA is shown in Appl Environ Microbiol. 2000 February; 66(2):775-82. (Characterization of a foldase, protein disulfide isomerase A, in the protein secretory pathway of *Aspergillus niger*. Ngiam C, Jeenes D J, Punt P J, Van Den Hondel Calif., Archer D B) or (Zrenner R, Willmitzer L, Sonnewald U. Analysis of the expression of potato uridinediphosphate-glucose pyrophosphorylase and its inhibition by antisense RNA. Planta. (1993); 1 90(2):247-52). Furthermore, modification, downregulation or inactivation of the gene may be obtained via the RNA interference (RNAi) technique (FEMS Microb. Lett. 237 (2004): 317-324). The RNA interference techniques described in WO 05/05672 A1 and/or WO 05/026356 A1 may be used for downregulation, modification or inactivation of the gene. Alternatively, a weak promoter may be used to direct the expression of the polynucleotide. In another embodiment, the promoter, regulatory region and/or the ribosome binding site upstream of the gene can be altered to achieve the down-expression. The expression may also be reduced by decreasing the relative half-life of the messenger RNA. In another embodiment, the activity of the polypeptide itself may be decreased by employing one or more mutations in the polypeptide amino acid sequence, which decrease the activity. For example, altering the affinity of the polypeptide for its corresponding substrate may result in reduced activity. Likewise, the relative half-life of the polypeptide may be decreased. In either scenario, that being reduced gene expression or reduced activity, the reduction may be achieved by altering the composition of the cell culture media and/or methods used for culturing. "Reduced expression", "down-regulation" or "reduced activity" as used herein means a decrease of at least 5%, 10%, 25%, 50%, 75%, 80%, 90%, 95% or even 100% compared to a wild-type (BS08) protein, polynucleotide, gene; or the activity and/or the concentration of the protein present before the polynucleotides or polypeptides are reduced. The activity of the BS08 protein may also be reduced by contacting the protein with a specific or general inhibitor of its activity.

Another aspect of the invention pertains to vectors, containing a nucleic acid encoding a protein according to the invention or a functional equivalent or portion thereof. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). An autonomously maintained cloning vector for a filamentous fungus may comprise the AMA1-sequence (see e.g. Aleksenko and Clutterbuck (1997), Fungal Genet. Biol. 21: 373-397). Other vectors (e.g., non-episomal mammalian vectors) are integrated into the genome of a host cell upon introduction into the host cell, and thereby are replicated along with the host genome.

Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions. Examples of the general design of expression vectors and the use of expression vectors for gene overexpression can be found in WO 99/32617, WO 01/21779 or WO 05/100573.

The recombinant vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g. attenuator). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, encoded by nucleic acids as described herein, including, but not limited to, mutant proteins, fragments thereof, variants or functional equivalents thereof, and fusion proteins, encoded by a nucleic acid as described herein, e.g., TS08, TS09, CS07 and/or BS08 proteins, mutant forms of TS08, TS09, CS07 and/or BS08 proteins, fusion proteins and the like.

The recombinant expression vectors of the invention may be designed for expression of TS08, TS09, CS07 and/or BS08 proteins in a suitable microorganism. For example, a protein according to the invention may be expressed in fungal cells such as strains belonging to the genera *Aspergillus, Acremonium, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma*. Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

Alternatively, the vector may be one which, when introduced into the filamentous fungal cell, is integrated into the genome and replicated together with the chromosome (s) into which it has been integrated. The integrative cloning vector may integrate at random or at a predetermined target locus in the chromosomes of the filamentous fungal host cell. In a preferred embodiment of the invention, the integrative cloning vector comprises a DNA fragment, which is homologous to a DNA sequence in a predetermined target locus in the genome of the filamentous fungal host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell. Such phenotype of the cell preferably involves a deficient ku70 gene as described in WO2005/095624. WO2005/095624, which is herein enclosed by reference, discloses a preferred method to obtain a filamentous fungal cell comprising increased efficiency of targeted integration. Preferably, the DNA sequence in the cloning vector, which is homologous to the target locus, is derived from a highly expressed locus meaning that it is derived from a gene, which is capable of high expression level in the filamentous fungal host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127). A number of preferred highly expressed fungal genes are given by way of example: the amylase, glucoamylase, alcohol dehydrogenase, xylanase, glyceraldehyde-phosphate dehydrogenase or cellobiohydrolase (cbh) genes from *Aspergilli* or *Trichoderma*. Most preferred highly expressed genes for these purposes are a glucoamylase gene, preferably an *A. niger* glucoamylase gene, an *A. oryzae* TAKA-amylase gene, an *A. nidulans* gpdA gene, a *Trichoderma reesei* cbh gene, preferably cbh1. The vector system may be a single vector or plasmid or two or more vectors or plasmids, which together contain the total DNA to be introduced into the genome of the filamentous fungal cell, or a transposon. More than one copy of a nucleotide sequence encoding a polypeptide may be inserted into the cell to increase production of the gene product. This can be done, preferably by integrating into the cell's chromosome of the nucleotide sequence, more preferably by targeting the integration of the nucleotide sequence at one of the highly expressed loci listed above. Integration may be enhanced by a recombinase. Alternatively, this can be done by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent. To increase even more the number of copies of the DNA sequence to be over expressed, the technique of gene conversion as described in WO 98/46772 may be used.

Alternatively, the recombinant expression vector can be transcribed and translated in vitro, for example using T7 promoter regulatory sequences and T7 polymerase.

The DNA insert may be operatively linked to an appropriate promoter, which may be either a constitutive or inducible promoter such as for instance the phage lambda PL promoter, the *E. coli* lac, trp and tac promoters, the SV40 early and late promoters and promoters of retroviral LTRs. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Preferably, the promoter may be derived from a gene, which is highly expressed (defined herein as the mRNA concentration with at least 0.5% (w/w) of the total cellular mRNA). In another preferred embodiment, the promoter may be derived from a gene, which is medium expressed (defined herein as the mRNA concentration with at least 0.01% until 0.5% (w/w) of the total cellular mRNA). In another preferred embodiment, the promoter may be derived from a gene, which is low expressed (defined herein as the mRNA concentration lower than 0.01% (w/w) of the total cellular mRNA).

More preferably, micro array data is used to select genes, and thus promoters of those genes, that have a certain transcriptional level and regulation. In this way one can adapt the gene expression cassettes optimally to the conditions it should function in. These promoter fragments can be derived from many sources, i.e. different species, PCR amplified, synthetically and the like.

The control sequence may also include a suitable transcription termination sequence, a sequence recognized by a eukaryotic cell to terminate transcription. The terminator sequence is operably linked to the 3'-terminus of the nucleic acid sequence encoding the polypeptide. Any terminator, which is functional in the cell, may be used in the present invention.

Preferred terminators for filamentous fungal cells are obtained from the genes encoding *Aspergillus oryzae* TAKA amylase; the *Penicillium chrysogenum* pcbAB, pcbC and penDE terminators; *Aspergillus niger* glucoamylase; *Aspergillus nidulans* anthranilate synthase; *Aspergillus niger* alpha-glucosidase; *Aspergillus nidulans* trpC gene; *Aspergillus nidulans* amdS; *Aspergillus nidulans* gpdA; *Fusarium oxysporum* trypsin-like protease.

The control sequence may also be a suitable leader sequence, a non-translated region of an mRNA that is important for translation by the cell. The leader sequence is operably linked to the 5'-terminus of the nucleic acid sequence encoding the polypeptide. Any leader sequence, which is functional in the cell, may be used in the present invention. Preferred leaders for filamentous fungal cells are obtained from the genes encoding *Aspergillus oryzae* TAKA amylase and *Aspergillus nidulans* triose phosphate isomerase and *Aspergillus niger* glaA.

The control sequence may also be a polyadenylation sequence, a sequence which is operably linked to the 3'-terminus of the nucleic acid sequence and which, when transcribed, is recognized by the cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding *Aspergillus oryzae* TAKA amylase, *Aspergillus niger* glucoamylase, *Aspergillus nidulans* anthranilate synthase, *Fusarium oxysporum* trypsin-like protease and *Aspergillus niger* alpha-glucosidase.

Control sequences may be the Kozak sequences, coding translation initiation sequences and termination sequences such as described in WO 2006/077258.

Vector DNA may be introduced into suitable host cells via conventional transformation or transfection techniques. As used herein, the terms "transformation", "transconjugation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells may be found in Sambrook, et al. (supra), Davis et al., Basic Methods in Molecular Biology (1986) and other laboratory manuals.

Transformation methods of *A. niger* are well-known to the skilled person (Biotechnology of Filamentous fungi: Technology and Products. (1992) Reed Publishing (USA); Chapter 6: Transformation pages 113 to 156). The skilled person will recognize that successful transformation of *A. niger* is not limited to the use of vectors, selection marker systems, promoters and transformation protocols specifically exemplified herein. Specific transformation protocols for *A. niger* are described in e.g. WO 99/32617 or WO 98/46772.

The vectors preferably contain one or more selectable markers, which permit easy selection of transformed cells. A selectable marker is a gene the product of which provides for biocide or viral resistance, resistance to heavy metals, prototrophy to auxotrophs, and the like. A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* and *Penicillium* cell are the amdS (EP 635574, WO 97/06261) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selection marker gene is the *A. nidulans* amdS coding sequence fused to the *A. nidulans* gpdA promoter as disclosed in EP 635574, which is herein enclosed by reference. AmdS genes from other fungi may also be used, e.g. the ones disclosed in WO 97/06261.

A nucleic acid encoding a selectable marker is preferably introduced into a host cell on the same vector as that encoding a protein according to the invention or can be introduced on a separate vector such as, for example, a suicide vector, which cannot replicate in the host cells. Cells stably transformed with the introduced nucleic acid can be identified by drug selection (e.g., cells that have incorporated the selectable marker gene will survive, while the other cells die).

The invention also provides an isolated polypeptide having an amino acid sequence according to SEQ ID NO's: 2, or 7, respectively or an amino acid sequence obtainable by expressing a polynucleotide of the present invention, such as for instance a polynucleotide sequence according to SEQ ID NO's: 1 or 6, respectively in an appropriate host.

In another embodiment, there is provided a polypeptide having the activity of a TS08 or TS09 protein, wherein said polypeptide is polypeptide having an amino acid sequence which has at least 70% homology, such as 75, 80, 85, 90, 91, 92, 93, 94, 95, 96, 97, 98, 99 or 99.5% with the amino acid sequence of SEQ ID NO: 2, or SEQ ID NO: 7, respectively.

Polypeptides (the terms "polypeptide" and "protein" are interchangeably used herein) according to the invention may contain only conservative substitutions of one or more amino acids in the amino acid sequences represented by SEQ ID NO's: 2, 7, 11 or 17, or substitutions, insertions or deletions of non-essential amino acids. Accordingly, a non-essential amino acid is a residue that may be altered in the amino acid sequences shown in SEQ ID NO's: 2, 7, 11 or 17 without substantially altering the biological function. For example, amino acid residues that are conserved among the proteins of the present invention, are predicted to be particularly unnameable to alteration. Furthermore, amino acids conserved among the proteins according to the present invention and other TS08, TS09, CS07 and/or BS08 proteins are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As mentioned above, the polynucleotides of the invention may be utilized in the genetic engineering of a suitable host cell to make it better and more efficient in the fermentation, for example in a fermentation process for citric acid.

According to the invention a genetically engineered/recombinantly produced host cell (also referred to as recombinant cell or transformed cell) carrying such a modified polynucleotide wherein the function of the linked protein is significantly modified in comparison to a wild-type cell such that the yield, production and/or efficiency of production of one or more fermentation products such as citric acid is improved. The host cell may be selected from a microorganism capable of producing one or more fermentation products such as for instance citric acid from a carbohydrate, such as filamentous fungi, in particular *Aspergillus*, preferably *Aspergillus niger*, more preferably *A. niger* CBS 513.88.

A "transformed cell" or "recombinant cell" is a cell into which (or into an ancestor of which) has been introduced, by means of recombinant DNA techniques, a nucleic acid according to the invention, or wherein the activity of the TS08, TS09, CS07 protein has been increased and/or enhanced and/or the activity of the BS08 protein has been decreased or abolished. Suitable host cells include cells of microorganisms capable of producing a given fermentation product, e.g., converting a given carbohydrate into citric acid.

In particular, these include strains selected from the group of filamentous fungi, preferably from *Aspergillus*, more preferably from *A. niger, A. awamori, A. aculeatus, A. japonicus, A. oryzae, A. vadensis, A. carbonarius, A. tubingensis, A. lacticoffeatus, A. brasiliensis, A. piperis A. costaricaensis* or *A. foetidus*, even more preferably *A. foetidus* var *acidus* or *A. foetidus* var *pallidus*, even more preferably from *A. niger* var *awamori*, even more preferably from *A. niger* ATCC1015 and most preferably from *A. niger* CBS 513.88.

Improved gene expression may also be achieved by modifying the TS08, TS09, CS07, TS08/TS09, TS08/CS07, TS09/CS07, or TS08/TS09/CS07 gene, e.g., by introducing one or more mutations into the TS08, TS09 and/or CS07 gene wherein said modification leads to a TS08, TS09, CS07, TS08/TS09, TS08/CS07, TS09/CS07, or TS08/TS09/CS07 protein with a function which is significantly improved in comparison to the wild-type protein.

Therefore, in one other embodiment, the polynucleotide carrying the at least one mutation is derived from a polynucleotide selected from the group of SEQ ID NO's: 1, 6 and/or 11, or equivalents thereof.

A mutation as used herein may be any mutation leading to a more functional or more stable polypeptide, e.g. more functional or more stable TS08, TS09, CS07, TS08/TS09, TS08/CS07, TS09/CS07, or TS08/TS09/CS07 gene products. This may include for instance an alteration in the genome of a microorganism, which improves the synthesis of a TS08, TS09, CS07, TS08/TS09, TS08/CS07, TS09/CS07, or TS08/TS09/CS07 protein or leads to the expression of a TS08, TS09, CS07, TS08/TS09, TS08/CS07, TS09/CS07, or TS08/TS09/CS07 protein with an altered amino acid sequence whose function compared with the wild type counterpart having a non-altered amino acid sequence is improved and/or enhanced. The improvement may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a more functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout or suppress a repressor of the TS08, TS09 and/or CS07 gene of the present invention, i.e., wherein its repressor gene expression is artificially suppressed in order to improve the yield, productivity, and/or efficiency of production of the fermentation product when introduced into a suitable host cell. Methods of providing knockouts as well as microorganisms carrying such suppressed genes are well known in the art. The suppression of the repressor gene may be induced by deleting at least a part of the repressor gene or the regulatory region thereof. As used herein, "suppression of the gene expression" includes complete and partial suppression, as well as suppression under specific conditions and also suppression of the expression of either one of the two alleles.

To improve the citric acid production of a recombinant host cell wherein TS08, TS09, CS07, TS08/TS09, TS08/CS07, TS09/CS07, or TS08/TS09/CS07 activity is enhanced or improved, gene expression of BS08 may be inhibited in that organism for instance by targeting nucleotide sequences complementary to the regulatory region of a BS08 nucleotide sequence (e.g., a BS08 promoter and/or enhancers) to form triple helical structures that prevent transcription of a BS08 gene in target cells. See generally, Helene, C. (1991) Anti cancer Drug Des. 6 (6): 569-84; Helene, C. et al. (1992) Ann. N.Y. Acad. Sci. 660: 27-36; and Maher, L. J. (1992) Bioassays 14 (12): 807-15.

Inhibition or prevention of gene expression may also be achieved by modifying a BS08 encoding gene, e.g., by introducing one or more mutations into the BS08 encoding gene wherein said modification leads to a BS08 protein with a function which is significantly decreased in comparison to the wild-type protein.

Therefore, in one other embodiment, the polynucleotide carrying the at least one mutation is derived from a polynucleotide encoding a BS08 polypeptide such as represented by SEQ ID NO: 16 or equivalents thereof.

A mutation as used herein may be any mutation leading to a less functional or unstable polypeptide, e.g. less functional or unstable BS08 gene products. This may include for instance an alteration in the genome of a microorganism, which interferes with the synthesis of BS08 or leads to the expression of a BS08 protein with an altered amino acid sequence whose function compared with the wild type counterpart having a non-altered amino acid sequence is completely or partially destroyed. The interference may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a less or non-functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout the BS08 encoding gene of the present invention, i.e., wherein its gene expression is artificially suppressed in order to improve the yield, productivity, and/or efficiency of production of the fermentation product when introduced into a suitable host cell. Methods of providing knockouts as well as microorganisms carrying such suppressed genes are well known in the art. The suppression of an endogenous BS08 gene may be induced by deleting at least a part of the gene or the regulatory region thereof.

As used herein, "suppression of gene expression" includes complete and partial suppression, as well as suppression under specific conditions and also suppression of the expression of either one of the two alleles.

In order to create a knockout microorganism in which the expression of a BS08 gene is artificially suppressed, first the BS08 gene may be cloned and then a vector for homologous recombination may be constructed by using the gene to inactivate the endogenous BS08 gene in the target microorganism. The vector for homologous recombination then contains a nucleic acid sequence designed to inactivate the endogenous BS08 gene in the target microorganism. Such a nucleic acid may be for instance a nucleic acid sequence of the BS08 gene or the regulatory region thereof, such as the existing flanking region of the gene to be inactivated (in cis), or existing separately (in trans), containing at least a partial deletion, or alternatively it may be a nucleic acid sequence of the BS08 gene or the regulatory region thereof containing other genes. Disruption and gene replacement are disclosed in EP 635 574 and WO 98/46772 and WO 05/095624. A gene which can also function as a marker is preferably selected as the gene to be inserted into the BS08 gene or the regulatory region thereof. The insert genes to be used include for instance drug-resistance genes as defined above. There is no particular limitation on the position where the genes may be inserted in the BS08 gene, as long as the insertion at that position results in the suppression of the expression of the endogenous BS08 gene in the target. To avoid polar effects of the insertion, in-frame silent deletions can be introduced by using, for example, the sacB system or long-flanking homology PCR. These techniques are well known to the person skilled in the art.

The aforementioned mutagenesis strategies for BS08 proteins may result in increased yields of a desired compound in particular citric acid. This list is not meant to be limiting; variations on these mutagenesis strategies will be readily apparent to one of ordinary skill in the art. By these mechanisms, the nucleic acid and protein molecules of the invention may be utilized to generate microorganisms such as *Aspergillus niger* or related strains of fungi expressing mutated BS08 nucleic acid and protein molecules such that the yield, productivity, and/or efficiency of production of a desired compound such as citric acid is improved.

The aforementioned mutagenesis strategies for a TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein may result in increased yields of a desired compound in particular citric acid. This list is not meant to be limiting; variations on these mutagenesis strategies will be readily apparent to one of ordinary skill in the art. By these mechanisms, the nucleic acid and protein molecules of the invention may be utilized to generate microorganisms such as *Aspergillus niger* or related strains expressing mutated TS08, TS09, CS07 and/or BS08 nucleic acid and protein molecules such that the yield, productivity, and/or efficiency of production of a desired compound such as citric acid is improved.

In one aspect of the invention, microorganisms (in particular filamentous fungi such as *Aspergillus*) are provided that are able to produce citric acid from a suitable carbohydrate like e.g. glucose, fructose, sucrose, molasses, cassaya, starch or corn. Measurement of citric acid is done by simple acid-base titration with NaOH keeping in mind that all acids are measured in this way. To measure citric acid in the presence of other acids, HPLC is used (e.g. with IonPac AS-11 anion exchange column of Dionex, as described in their publicly available application note no 123 of December 1998 "The determination of inorganic anions and organic acids in fermentation broths", Dionex Corp., Sunnyvale, Calif.). When measured for instance by HPLC or titration, these organisms were found to be able to produce citric acid from sucrose up to a level of 100 g/l respectively. In another aspect of the invention, a microorganism is provided capable of producing citric acid in quantities of 300 g/l when produced by submerged fermentation starting from sucrose. Such may be achieved by increasing the activity of a TS and/or CS polypeptide, preferably a TS08, TS09 and/or CS07 polypeptide. The yield of citric acid produced from e.g. sucrose may even be as high as 1.5, 2, 4, 10, 20, 50 g/l, or even exceed 400, 600, 1000 g/l Such may be achieved by enhancing or improving the activity of a TS, or CS polypeptide, preferably a TS08, TS09, CS07, TS08/TS09, TS08/CS07, TS09/CS07, or TS08/TS09 and CS07 polypeptide, optionally combined with decreasing or abolishing the activity of a BS protein, preferably a BS08 protein. The yield of citric acid produced from e.g. sucrose may even be as high as 1.5, 2, 4, 10, 20, 50 g/l or even exceed 400, 600, 1000 g/l. The yield of citric acid using a microorganism carrying the modified gene as described herein may be increased by at least 1%, 2%, 3% 4%, 8%, 10%, 15%, 20%, 30%, 40%, 50%, 100%, 200%, 500% or more compared to the amount of citric acid produced by the wild-type strain such as e.g. *A. niger* CBS 513.88.

The recombinant microorganism carrying e.g. a modified TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 gene and which is able to produce the fermentation product in significantly higher yield, productivity, and/or efficiency may be cultured in an aqueous medium supplemented with appropriate nutrients under suitable conditions. Production of citric acid may be conducted via submerged or surface fermentation starting from different carbohydrates and/or raw materials.

In one embodiment, citric acid is produced via submerged fermentation starting from a carbohydrate raw material such as for instance cassaya and/or corn, which may be milled and mixed with water. A seed fermentation may be prepared in a separate fermentor. The liquefaction of the starch may be performed in the presence of an amylolytic enzyme such as for instance amylases, cellulases, lactases or maltases and additives and nutrients such as antifoam may be added before or during fermentation. For the main fermentation, the concentration of carbohydrate, e.g. starch, in the mix may be in the range of 150 to 200 g/l, preferably about 180 g/l.

In a further embodiment, citric acid is produced via surface fermentation starting from a carbohydrate raw material such as for instance a mix of beet and cane molasses or sucrose.

The nucleic acid molecules, polypeptides, vectors, primers, and recombinant microorganisms described herein may be used in one or more of the following methods: identification of *Aspergillus niger* and related organisms; mapping of genomes of organisms related to *Aspergillus niger*; identification and localization of *Aspergillus niger* sequences of interest; evolutionary studies; determination of TS08, TS09, CS07 and/or BS08 protein regions required for function; modulation of a TS08, TS09, CS07 and/or BS08 protein activity or function; modulation of the activity of a TS pathway; and modulation of cellular production of a desired compound, such as citric acid.

The invention provides methods for screening molecules which modulate the activity of a TS08, TS09 and/or CS07 protein, either by interacting with the protein itself or a substrate or binding partner of a TS08, TS09 and/or CS07 protein, or by modulating the transcription or translation of a TS08, TS09, CS07 and/or SB08 nucleic acid molecule of the invention. In such methods, a microorganism expressing a TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 proteins of the invention is contacted with one or more test compounds, and the effect of each test compound on the activity or level of expression of the TS08, TS09, CS07 and/or BS08 protein is assessed.

The biological, enzymatic or other activity of TS, CS and/or BS proteins can be measured by methods well known to a skilled person, such as, for example, by incubating a membrane fraction containing the TS08, TS09, CS07 and/or BS08 protein with the radioactively marked sugar, sugar alcohol or carboxylates which can be actively transported by a TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein. The incorporation of radioactivity into the cell mass is directly proportional to the activity of the transporter. Thus, for example, the activity of a transporter can be measured in an assay where intact cells containing the specific transporter are incubated in the presence of phosphate buffer at pH 6 and the radioactively marked carbon source such as e.g. glucose. The rate of assimilation of radioactive carbon source such as e.g. glucose by the cells can be measured by methods known to the skilled person, and is directly proportional to the TS, CS and/or BS protein activity present in the membrane fraction.

In an alternative assay, the biological, enzymatic or other activity of TS, CS and/or BS proteins can be measured by methods well known to a skilled person, such as, for example, by complementing a *Saccharomyces* disruption mutant for a corresponding (orthologue) transporter gene with an *A. niger* cDNA clone encoding a TS08, TS09, CS07, TS08/TS09, TS08/CS07, TS09/CS07, TS08/TS09/CS07, TS08/BS08, TS09/BS08, CS07/BS08, TS08/TS09/BS08, TS08/CS07/BS08, TS09/CS07/BS08, or TS08/TS09/CS07/BS08 protein of the invention. Positive complementation of a transporter minus phenotype is an indication for transporter activity.

It may be evident from the above description that the fermentation product of the methods according to the invention may not be limited to citric acid alone. The "desired compound" or "fermentation product" as used herein may be any natural or heterologous products of *Aspergillus niger*, which includes the final products and intermediates of biosynthesis pathways, such as for example primary and secondary metabolites as e.g. beta-lactams, proteins or enzymes in particular the biosynthetic generation of citric acid.

Thus, the present invention is directed to the use of a polynucleotide, polypeptide, vector, primer and recombinant microorganism as described herein in the production of citric acid, i.e., the conversion of a carbon source into citric acid. In a preferred embodiment, a modified polynucleotide, polypeptide, vector and recombinant microorganism as described herein is used for improving the yield, productivity, and/or efficiency of the production of citric acid.

The terms "production" or "productivity" are art-recognized and include the concentration of the fermentation product (for example, citric acid) formed within a given time and a given fermentation volume (e.g., kg product per hour per litre). The term "efficiency of production" includes the time required for a particular level of production to be achieved (for example, how long it takes for the cell to attain a particular rate of output of a fermentation product). The term "yield" is art-recognized and includes the efficiency of the conversion of the carbohydrate into the product (i.e., citric acid). This is generally written as, for example, kg product per kg carbon source. By "increasing the yield and/or production", or increasing the performance of production" of the compound it is meant that the quantity of recovered molecules, or of useful recovered molecules of that compound in a given amount of culture over a given amount of time is increased.

The terms "biosynthesis" or a "biosynthetic pathway" are art-recognized and include the synthesis of a compound, preferably an organic compound, by a cell from intermediate compounds in what may be a multi-step and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The language "transport" or "import" is art-recognized and includes the facilitated movement of one or more molecules across a cellular membrane through which the molecule would otherwise either be unable to pass or be passed inefficiently.

Citric acid as used herein may be any chemical form of citric acid found in aqueous solutions, such as for instance un-dissociated, in its free acid form or dissociated as an anion. The solubilized salt form of citric acid may be characterized as the anion in the presence of any kind of cations usually found in fermentation supernatants, such as for instance potassium, sodium, calcium or ammonium. Also included may be isolated crystals of the free acid form of citric acid. On the other hand, isolated crystals of a salt form of citric acid are called by their corresponding salt name, i.e. sodium citrate, potassium citrate, calcium citrate and the like.

In one preferred embodiment, the present invention is related to a process for the production of citric acid wherein a nucleotide according to the invention or a modified polynucleotide sequence as described above is introduced into a suitable microorganism, the recombinant microorganism is cultured under conditions that allow the production of citric acid in high productivity, yield, and/or efficiency, the produced fermentation product is isolated from the culture medium and optionally further purified.

In a further aspect, the process for the production of citric acid as described above may be combined with further steps of separation and/or purification of the produced citric acid from other components in the fermentation broth, i.e. so-called downstream processing steps. These steps may include any means known to a skilled person, such as, for instance, concentration, crystallization, precipitation, adsorption, ion exchange, electrodialysis, bipolar membrane electrodialysis and/or reverse osmosis. Citric acid may be further purified as the free acid form or any of its known salt forms by means of operations such as for instance treatment with activated carbon, ion exchange, adsorption and elution, concentration, crystallization, filtration and drying. Combination of the mentioned steps, e.g., electrodialysis and bipolar membrane electrodialysis into one step might be also used as well as combination of the mentioned steps e.g. several steps of ion exchange by using simulated moving bed chromatographic methods. Any of these procedures alone or in combination constitute a convenient means for isolating and purifying the product, i.e. citric acid. The product thus obtained may further be isolated in a manner such as, e.g. by concentration, crystallization, precipitation, washing and drying of the crystals and/or further purified by, for instance, treatment with activated carbon, ion exchange and/or re-crystallization.

The downstream processing procedure may include for instance the isolation of citric acid by means of precipitation with lime, chromatography or solvent extraction. Purification may include treatment with activated carbon, ion exchangers, crystallization and/or filtration steps. Final product forms are obtained by concentration and crystallization, or for the salt forms, by neutralizing the citric acid with the wanted base (like NaOH, KOH, $NH_3$ and the like). These crystals can be separated, washed and dried. If necessary, the crystals may be again re-solubilized in water, treated with activated carbon and/or ion exchange resins and recrystallized. These crystals can then be separated, washed and dried.

Citric acid may be converted for instance into monosodium citrate, trisodium citrate, tricalcium citrate, trisodium citrate dihydrate, tripotassium citrate, monosodium citrate anhydrous, or crystallized as citric acid anhydrous or citric acid monohydrate.

Citric acid and its salts as produced by a method described herein may be further used as ingredient or additive for e.g. food (such as e.g. bakery products, baby food, fats and oils, sweets, cheese products, dairy products), beverages such as e.g. carbonated soft drinks, syrups, fruit juices and drinks, wines, ready-to-drink teas), pharmaceuticals (such as e.g. tablets, syrups, suspensions/solutions), cleaners and detergents (such as e.g. deodorant soap, dish washing liquids/powders), in personal care products (such as e.g. shampoos, creams and lotions, hygiene products, toothpastes) or in other industrial applications such as in adhesives, animal feed, photo chemicals and the like.

Thus in one embodiment the present invention is related to a food, feed, beverage, pharmaceutical, cleaner, detergent or personal care product comprising citric acid as produced by a process described herein.

This invention is further illustrated by the following examples which should not be construed as limiting. The contents of all references, patent applications, patents and published patent applications, cited throughout this application are hereby incorporated by reference.

EXAMPLES

Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574 B1. This patent discloses how to delete glaA specific DNA sequences in the genome of CBS 513.88. The procedure resulted in a MARKER-GENE FREE delta-glaA recombinant *A. niger* CBS 513.88 strain, possessing no foreign DNA sequences.

WT 3: This *A. niger* strain is a WT 2 strain comprising a mutation which results in an oxalate deficient *A. niger* strain. WT 3 was constructed by using the method as described in EP1590444. This patent application, discloses how to screen for an oxalate deficient *A. niger* strain. Strain WT3 was constructed according to the methods of examples 1 and 2 of EP1590444, strain WT 3 is mutant strain 22 of EP1590444 (designated FINAL in EP1590444).

Example 1

Preparation of Chromosomal DNA and Amplification of DNA Fragment by PCR

Chromosomal DNA of *Aspergillus niger* CBS 513.88 was prepared from cells cultivated in 500 ml flasks with baffle with 100 ml fermentation broth (MM-G) as indicated at 30° C. and 150 rpm for 16-20 h. MM-G medium contains per litre: 20 g D-glucose, 6 g NaNO$_3$, 0.25 g KCl, 1.5 g KH$_2$PO$_4$, 1.13 ml 4 M KOH, 0.5 g MgSO$_4$.7H$_2$O, 1 ml of stock trace elements (stock trace elements per liter: 22 g ZnSO$_4$.7H$_2$O, 11 g H$_3$BO$_3$, 5 g FeSO$_4$.7H$_2$O, 1.7 g CoCl$_2$.6H$_2$O, 1.6 g CuSO$_4$.5H$_2$O, 5 g MnCl$_2$-4H$_2$O, 1.5 g Na$_2$MoO$_4$.2H$_2$O, 50 g EDTA, adjusted the pH to 6.5 with 4 M KOH, filter sterilized and stored in the dark at 4° C.). Shake-flask fermentation and chromosomal DNA isolation are in more detail described in WO 98/46772.

DNA fragments were prepared by PCR with the chromosomal DNA prepared above and a set of primers, Pf (SEQ ID NO's: 3, 8, 13 and 18 respectively) and Pr (SEQ ID NO's: 4, 9, 14 and 19, respectively). For the reaction, the Platinum Pfx polymerase (Invitrogen) and 50 ng of the chromosomal DNA was used in total volume of 50 µl according to the supplier's instruction to generate the respective PCR products containing the respective DNA sequences (SEQ ID NO's: 1, 6, 11 and 16). The PCR products were recovered from the reaction mix and the correct sequences were confirmed.

Construction of Overexpression and Knock-Out Vectors

Figure 1:
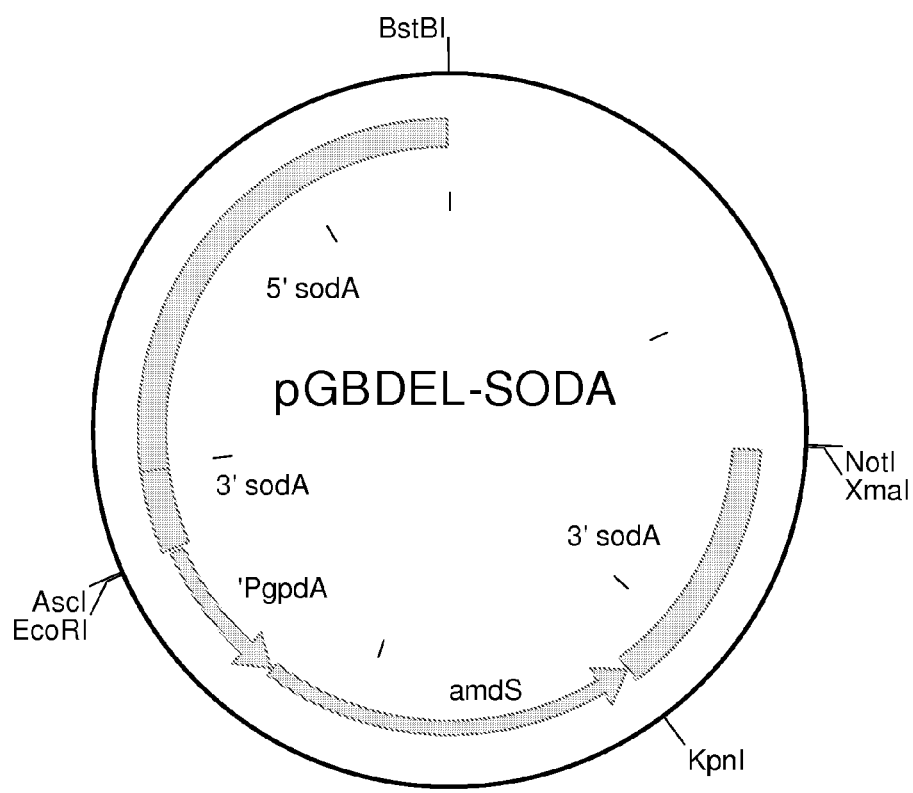
FIG. 1: Plasmid map of the BS08 gene replacement vector pGBDEL-SODA.

Cloning techniques and plasmid DNA isolation was performed according to known principles and routine plasmid isolation techniques (Sambrook, J. et al., 1989). Sequences, which are candidate for disruption, comprise the open reading frame (ORF) (with introns) and approximately 1500 bp 5' and 3' sequence of the genes. A gene replacement vector for the SB 08 gene was designed according to known principles and constructed according to routine cloning procedures (see FIG. 1). In essence, these vectors comprise approximately 1500 bp flanking regions of the SB 08 ORF, for homologous recombination at the predestined genomic SB 08 locus. In addition, they contain the *A. nidulans* bi-directional amdS selection marker, in-between direct repeats. The general design of these deletion vectors were previously described in EP635574B and WO 98/46772.

Overexpression vectors for the TS08, TS09 and CS07 genes were designed according to known principles and constructed according to routine cloning procedures. Examples of the general design of expression vectors and the use of expression vectors for gene overexpression can be found in WO199932617, WO200121779 and WO2005100573.

In essence, expression vectors comprise at least a promoter and terminator for proper expression of a gene. The genomic TS08, TS09 and CS07 DNA's or cDNA's, as listed in Table 1 for example, were used for cloning and overexpression of the genes mentioned. A selection marker for transformation, such as the *A. nidulans* bi-directional amdS selection marker can be on the vector or can be used as separated vector in co-transformation. Examples of pGBTOP-based or pGBFIN-based expression vectors can be found in FIG. 3 or 4. All *A. niger* TS08, TS09 and CS07 genes were cloned in a pGBFIN-based overexpression vector. The pGBFINMNR-1 vector is an example of a pGBFIN-based vector for overexpression vector of the TS08 protein (FIG. 5).

Example 2

Disruption of the BS08 Gene in *A. niger* WT3

Linear DNA of a deletion vector digested with appropriate restriction enzymes, such as pGBDEL-SODA (FIG. 3), was isolated and used to transform *A. niger* WT 3 using methods earlier described (Biotechnology of Filamentous fungi: Technology and Products. (1992) Reed Publishing (USA); Chapter 6: Transformation pages 113 to 156). This linear DNA can integrate into the genome at the homologous locus, thus substituting the endogenous BS08 gene, encoding the BS08 polypeptide, by the amdS gene. An illustration of this event is as depicted in FIG. 2. Transformants were selected on acetamide media and colony purified according to standard procedures as described in EP 635 574. Spores were plated on fluoro-acetamide media to select strains, which lost the amdS marker. Growing colonies were diagnosed by PCR for integration at the homologous locus and candidate strains tested by Southern analyses for deletion of the endogenous BS08 gene. Deletion of the BS08 gene was detectable by ~0.9 kb size reduction of DNA fragments covering the entire locus and hybridized to appropriate probes of flanking sequences. Approximately 3 strains showed a removal of the genomic BS08 gene from a pool of approximately 100 initial transformants. Strain delta BS08 was selected as a representative strain with the endogenous sodA gene inactivated.

Example 3

Overexpression of the TS08, TS09 and CS07 Genes in A. niger WT3 and Delta BS08

The TS08, TS09 and CS07 genes obtained in Example 1 were cloned into a pGBFIN overexpression vector (WO99/32617). After linearization with an appropriate restriction enzyme, the linear DNA was used to transform A. niger strain WT 3 and delta SB 08 [for transformation, see e.g. Biotechnology of Filamentous fungi: Technology and Products. (1992) Reed Publishing (USA); Chapter 6: Transformation pages 113 to 156]. The linear DNA was integrated into the genome and transformants for A. niger overexpressing TS08, TS09, and CS07 were selected on acetamide media and colony purified according to standard procedures as described in e.g. EP 635 574. The transformation and subsequent transformant selection are disclosed in WO 98/46772. Strains WT3-TS08, WT3-TS09, WT3-CS07, delta BS08-TS08, delta BS08-TS09 and delta BS08-CS07 were selected as representative strains with the indicated genes overexpressed and the endogenous BS08 gene inactivated, respectively.

By use of co-transformation with all three pGBFIN overexpression constructs (TS08, TS09 and CS07) strains were constructed having multiple overexpression constructs (delta BS08-TS08/TS09, delta BS08-TS08/CS07, delta BS08-TS09/CS07 and delta BS08-TS08/TS09/CS07). These strains were diagnosed and selected by PCR for integration of one or more of the respective genes of interest.

Representative strains, with a genetic makeup as indicated in Table 2, were selected for further experiments.

TABLE 2

Genetic make-up of obtained *Aspergillus niger* clones

| Strain | TS08 | TS09 | CS07 | BS08 |
|---|---|---|---|---|
| WT 3 | | | | |
| delta BS08 | | | | delta |
| WT3-TS08 | + | | | |
| WT3-TS09 | | + | | |
| WT3-CS07 | | | + | |
| WT3-TS08/TS09 | + | + | | |
| WT3-TS08/CS07 | + | | + | |
| WT3-TS09/CS07 | | + | + | |
| WT3-TS08/TS09/CS09 | + | + | + | |
| delta BS08-TS08 | + | | | delta |
| delta BS08-TS09 | | + | | delta |
| delta BS08-CS07 | | | + | delta |
| delta BS08-TS08/TS09 | + | + | | delta |
| delta BS08-TS08/CS07 | + | | + | delta |
| delta BS08-TS09/CS07 | | + | + | delta |
| delta BS08-TS08/TS09/CS07 | + | + | + | delta |

Example 4

Production of Citric Acid by Surface Fermentation Using the Disruption and Overexpression A. niger Strains A mixture of beet and cane molasses was diluted with demineralized water to obtain 240 g sucrose per liter. To this mixture 3 ml phosphoric acid 5%, 0.5 g $Na_4Fe(CN)_6 \cdot 10H_2O$, 0.45 g powdered activated carbon and 1.0 mg Zn was added. The pH was adjusted to 6.15 with sulphuric acid and the mixture was put in a tray with a depth of 10 cm. This tray was pasteurized at 70° C. and allowed to cool down to 40° C. Spores of the transformed A. niger strains obtained in Example 3 as well as the WT 3 and delta BS08 strains were added to the media and the trays were incubated in a climate room at a temperature of 35° C. and a relative humidity of at least 70%. The mycelium was cultivated to form a layer on the surface of the liquid and sucrose from the liquid was converted to citric acid. Fermentation was stopped when the sucrose, glucose and fructose concentration had dropped below 4 g/l as measured by HPLC. After pasteurization to stop enzymatic activity, the citric acid concentration in the liquid was measured by HPLC or titration. Production performance of the various strains was calculated as the yield of citric acid production compared to the yield of the WT3 strain, which was set at 100%. The A. niger strains overexpressing the CS07 gene, the TS08 gene or the TS09 gene, and A. niger strains overexpressing combinations of these genes, produced at least approximately 3% to over 20% more citric acid than obtained with A. niger strain WT 3 when cultured under the same conditions. These results are depicted in FIG. 6.

The strains with the BS08 disrupted background produced at least approximately 5% more citric acid under the same conditions than obtained with A. niger strain WT 3. In this BS08 disrupted background, A. niger strains overexpressing the CS07 gene, the TS08 gene or the TS09 gene, and A. niger strains overexpressing combinations of these genes, produced at least approximately 1% to over 15% more citric acid than obtained with strain A. niger delta BS08 when cultured under the same conditions. These results are depicted in FIG. 7.

These results confirm that overexpression of TS08 and/or TS09 and/or CS07 have a positive effect on citric acid production in surface fermentation, which possibly can be combined with BS08 disruption or reduced expression, in a citric acid producing cell. This improvement is found in a strain with an improved background for citric acid production compared to wild-type A. niger CBS513.88.

Example 5

Production of Citric Acid by Submerged Fermentation Using the Disruption and Overexpression A. niger Strains The carbohydrate raw material, e.g. cassaya and/or corn, were milled and mixed with water. A seed fermentation is started in a separate fermentor, containing a slurry of corn flour as carbohydrate, liquefied with an amylolytic enzyme at a temperature of 90° C. After cooling to 37° C., spores of either the A. niger strain WT 3, delta SB08 or the A. niger transformant strains as constructed in Example 3 were brought in the fermentor and the seed fermentation was carried out with an air flow rate of 0.1 to 0.2 vvm and the temperature was controlled at 37° C. After approximately 20 hours, the seed fermentor contents was transferred to the main fermentor. The main fermentor was prepared with a mix of corn and/or cassaya flour by adding water, additives and nutrients, wherein the concentration of carbohydrate in the mix was preferably 180 g/l and an amylolytic enzyme and antifoam was added. After heating to 90° C. to liquefy the starch and subsequently cooling to 35° C., the content of a seed fermentor was transferred to the main fermentor. After the transfer, the fermentation was controlled by cooling at an air flow rate of 0.1 vvm and stopped when the carbohydrate was consumed, which typically took 60-100 hours. The citric acid concentration in the liquid was measured by HPLC or titration. Performance of the various strains was calculated as the yield of citric acid production compared to the yield of the WT3 strain, which was set at 100%. The yield of citric acid monohydrate obtained by conversion of glucose was at least approximately 1% to over 8% more for *A. niger* strains overexpressing the CS07 gene, the TS08 gene or the TS09 gene, and *A. niger* strains overexpressing combinations of these genes, than obtained with *A. niger* strain WT 3 when cultured under the same conditions. These results are depicted in FIG. 8.

In addition, the strain with the BS08 disrupted background produced at least 5% more citric acid under the same conditions than obtained with strain *A. niger* WT 3. In this BS08 disrupted background, *A. niger* strains overexpressing the CS07 gene, the TS08 gene or the TS09 gene, and *A. niger* strains overexpressing combinations of these genes, produced at least approximately equal to over 15% more citric acid than obtained with strain *A. niger* delta BS08 when cultured under the same conditions. These results are depicted in FIG. 9.

These results confirm that overexpression of TS08, TS09 and/or CS07 have a positive effect on citric acid production in submerged fermentations, which possibly can be combined with BS08 disruption or reduced expression, in a cell producing citric acid. This improvement is found in a strain with an improved background for citric acid production compared to wild-type *A. niger* CBS513.88.

The invention claimed is:

1. A genetically modified TS08 polynucleotide selected from the group consisting of:
   (a) polynucleotides encoding a TS08 polypeptide active in the transport of substances over a membrane and having manganese resistance protein 1 activity (TS08 polypeptide) comprising an amino acid sequence according to SEQ ID NO: 2;
   (b) a polynucleotide comprising a nucleotide sequence according to SEQ ID NO: 1;
   (c) polynucleotides comprising a nucleotide sequence obtainable by nucleic acid amplification such as polymerase chain reaction, using genomic DNA from a microorganism as a template and a primer set having the nucleotide sequences of SEQ ID NO:3 and SEQ ID NO:4, respectively;
   (d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the ability to increase citric acid production;
   (e) polynucleotides which are at least 95% identical to a polynucleotide as defined in any one of (a) to (d) and which encode a TS08 polypeptide, or the full complementary strand of said polynucleotide and which retain the ability to increase citric acid production; and
   (f) fragments of the polynucleotides of (e) which retain the ability to increase citric acid production.

2. A vector comprising the TS08 polynucleotide according to claim 1.

3. The vector of claim 2 in which the TS08 polynucleotide is operatively linked to expression control sequences allowing the expression in prokaryotic or eukaryotic host cells.

4. An isolated microorganism genetically engineered with a TS08 polynucleotide according to claim 1.

5. A TS08 microorganism according to claim 4, additionally genetically engineered with a polynucleotide comprising a polynucleotide encoding a protein involved in the citrate synthesis system (a CS07 protein).

6. A TS08, or TS08/CS07 microorganism according to claim 4, additionally genetically engineered with a polynucleotide comprising a polynucleotide for disruption or downregulation of a BS08 polynucleotide encoding a protein having mitochondrial superoxide dismutase MnSOD activity.

7. A TS08, TS08/CS07, deltaBS08-TS08, or deltaBS08-TS08/CS07 microorganism according to claim 4, wherein additionally, reduced production or activity of a BS08 polypeptide is obtained by modification or inactivation of a nucleic acid sequence present in the cell necessary for expression of the BS08 polynucleotide.

8. A microorganism according to claim 4 capable of producing citric acid from sucrose in quantities of 100 g/l or more.

9. A Process for the production of a polypeptide having the activity of a TS08 protein, having an amino acid sequence which has at least 95% identity with the amino acid sequence of SEQ ID NO: 2, comprising the step of altering said microorganism so that the microorganism produces said polypeptide with increased and/or improved TS08, or TS08/CS07, activity, optionally combined with decreased or abolished BS08 activity leading to an improved yield and/or efficiency of production of citric acid produced from a carbohydrate by said microorganism.

10. The polynucleotide of claim 1, wherein in item (e) the polynucleotide is at least 98% identical to a polynucleotide as defined in anyone of (a) to (c) of claim 1 and which encodes a TS08 polypeptide, or the full complementary strand of said polynucleotide and which retain the ability to increase citric acid production.

11. The polynucleotide of claim 1, wherein in item (e) the polynucleotide is at least 99% identical to a polynucleotide as defined in anyone of (a) to (c) of claim 1 and which encodes a TS08 polypeptide, or the full complementary strand of said polynucleotide and which retain the ability to increase citric acid production.

* * * * *

SEQUENCE LISTING

```
<160> NUMBER OF SEQ ID NOS: 20

<210> SEQ ID NO 1
<211> LENGTH: 4849
<212> TYPE: DNA
<213> ORGANISM: Aspergillus niger

<400> SEQUENCE: 1
ataattttgt aagctataag ctgtcttcaa tttagacata ccaacataac agccagttgt      60
atcagcgcat tccatctggt ttaggctgaa gacgcctgaa tataggggac tcagacaagt     120
tcctcaatgt cgaaaacaga tgatttggtg actagcattc gtcttgggta gctttcgagt     180
ccctggtaca ttgaaaagac ttttgtgaaa cggtgactgc ccatctagtc aacttgccca     240
aggtaatagt cgtcgtgcac tggatatcag ttgggggagc tctcgcaata aatagccatc     300
gaaagggtca ccactggagt agggtcttgg agagtgcgtc ttttctgat  tgccattacg     360 cgttctttga cccgcaatcg gtataccaag aaattgttcg gaaccacat  aatatgctgg     420 ccgaggcatc tggtcccccta tcttgtgaat tcgatagcat ggcgttggga agaaacctct     480
ggagccgctc tagcatggaa tctagacgct tggctcaagg gttggcgaat ccatcaaccc     540
aattgcgcga ttaaagtgat ttggaatggt gttttccaca atgtagtatt ccgaagccac     600
aacggtgcgg ttccatttgc atgaatggtc cgatatcgaa taaagatctt ggtcccattg     660
attgccgacg cggcagcagc cgcacggaaa catcagaatc tcgcggttcc agactgcggc     720
cctatctgta attctacaac ccaatatggc cattatcatc aagtaaatgc tgccgttgtg     780
tactatgaag aagcagatct aggcgcttaa atcccatgga gcttatcgaa tcagagggaa     840
gataaggcca agcagatcga tcagctgcag caagggagaa ggacaaggcg catcacggga     900
ttacaaggat tccataactt ggctgccaaa ccacctcaat cttctatcat atgttcatct     960
tctgtgctca ttgagccttt ctttccggtt acccatgggg tatccatgca gagtccgttt    1020
ttcgctgaaa accaatgtgt caccgaatct acgagaacac aatgttgcct agaactgttg    1080
tttttagtcg gtctgggcgc ggcccagttg gccacacttc accgcgaaca gcctcgaaac    1140
cgcatgccgt catgctacca aaattctgaa tttcccctt  ctcttccctc tcctgcttcc    1200
gactggagtg aaagtcactg atttcatctt ttggaccccat cttccgtcgt aacaactgca    1260
```

```
cttgaacaca tagcagtcga tctatctatt tcctccggct ctcttccctg ttccgcagtg   1320
gacgtgtcta cagcgactac cgcaatcggg cagtttcggg caggcttccc cgcagggtcc   1380
ttgagtccta gactgacgtc ccgaagtggc gttgcctaaa taccccgatc tcgtggctat   1440
cggaatagct gcaattgcta atatttcaag ttgtgtcact gaagagcttc tcagtccgcc   1500
atgaattgtc cttcgcgcac cgatgacacc ctcgagcacc cgggatggaa ccagaatccg   1560
ccggcgctga atgccgacat taccactcga agcgacttca acggcattgc gaactcgaag   1620
gtgcatcgga gacatgcagg cggtatggga ggggctgcag ctgaaggtat tgcggcgatg   1680
gatcatagac caaatagtct agatggaaac gagcccgaga tggagaagaa gacacccggc   1740
gaagtgattg ctgccgctcc tggggaccaa tcacccagga cgagcagcga atcacctcgc   1800
cgtcctttca aaaatcaac tatatctttc tttctccgtc tagctcaaag tatcaagaag    1860
tttggtcgct tcgtgggccc tggattcctg atcgcggtag cctacattga tccgggaaac   1920
tactccaccg atgtcgccgc aggcgcggag tttcgctatg cttttgctct tcatcgtccta  1980 gtgtccaacc ttttgctat ttttctacag tcgctgtgta tcaaactcgg cacagtgaca    2040
gggctcaatc tggcggaaaa ctgcaggagc atctgcccca gtggttgaaa ctacatcctg   2100 tatgttttg cggaggccgc catcgtggca accgatatcg cagaggtacg cagccaatgt    2160
ttcccctccc tgttttctga cgctggtgct aagctggttt cctaggttgt cgggtctgcg   2220
atttcgctca accttctcct gaaaatccct ctggtggctg gatgcgcaat cacattagcc   2280
gatgttcttt tcatcctgat attctaccga ccgaatggcg ccatgtgggg actgcgtcta   2340
ttcgagttct tcgtcatgct gttggttctg ggagttgtca tatgcttttg catccagctt   2400
gcccttatca agaacagtc ggtcggagct gttttccggg gctacttgcc ttcgtctgcc    2460
atagtgcagt ccaatgggtg agtagcccga tttgtatatg actggaaaca ctgagtttgc   2520
taatatattg ttttccagtc tgtatcaaag ctgtggtatc ctcggtgcta cagtgatgcc   2580
tcactccatg tttcttggca gcggagttgt ccaatcgcga ctgaaggaat tcgatgttac   2640
ccaaggctac gtcgatccct ccgtctgcct tggaagcacc aacggagaag tggaatacag   2700
gccgtcaatc caggcgatta ggggctgtct gaagtattcc gtcattgagc ttacgttgtc   2760 ccttttaca tttgccctct tcgtcaacag cgccattctc atagttgctg gtgcttccct    2820
gtacggaacg tcgggagctg atgaagcaga cctctggggc atctacaatc ttctctccag   2880
ctccattgct ccggctgcag gtcttatctt tgcactggcc ctacttctct caggtatctc   2940
ggccggcatt gtctgtacca tggctgggca aatggttagc gagggaatgc tgaactggag   3000
catcagacct tggcttcgcc gactggtcac gcggtccatc agtatcatcc ctagcataat   3060
cattgcagct gctgtcggca aggagggatt gaacaaaact ctcaacgcca gtcaagtggt   3120
attgagtgtc atccttccgt ttgtcaccgc tcctctagtt tactttacgt gccgcaaccg   3180
ttacatgact gttcctacgg acagaaactt cactggcgag gattcctcgg ctgacggagt   3240
caagatgaga aacaactggc ttgttactgc catcgctgtc attgtttggg taatcattgc   3300
ggtcatgaac gttgctttgc tcatccttat tgggctcggc aaagcctgag agcgagaaac   3360
gcatggaacg ccgaatccag ggaacaacat cttttcagaa ggaagtttcg ctggaatgtg   3420
caagccgtgt ggctcagaat agtggacaca tagtaagata cactccgaag atgcagacac   3480
ataggggacg ggagagcgca gaaagaacat agataataaa agctcgtaga atgaacacag   3540
cttagtcgat tcatttaagg ggaagaaaaa gtgaacaaga aaaatccaaa ctccgatgcc   3600
accatgatct gaactcctaa acgctattct cgtaaaacat gtaatcctaa cccaacccac   3660
```

-continued

```
tagcaggctc cttaacctta gtctgctctg ggggctcatc aatgaactgc ggcggcgcca    3720
cctcatcttg caggaagcta ggcatagcac tatcagccat cgagctctcc atcatagtct    3780
cctcgcctag cgcctccaat tccgcatcga gttccgcctc atcgacatcc tcgggaacgt    3840
catacgcccg cgatatactt tcctggattt cattccccac gtccatcaaa tccgccatct    3900
catcctgcag ccgttcaatc ttatcaatat caatctgacc atactgcttc ttgagggtct    3960
tggttgtcgt cttcatagca tcaaccgtcg tcatacatt cttcagatta tcctgcatca    4020
tgcccgcctg ctccatattc catgactgct gcgacagctg atcccgctgc gcttcgtact    4080
gtttccgtcg ctggagaacc ttgagggctt tctgccgtaa cgcggttttt cccggcccgt    4140
cgcgcatctt ggagatcttg gtttgatagg tagatagttc cgagttgaga gccgccagct    4200
tgacgtcaat gctggaaatg cgtgtttcca cctgtcgggg aaatgttaat catgcggggt    4260
caggcggata agggacgaga tgaattcgga gagttgggca caatgatga atgacgaagg    4320 ttggaaggga aaaggggaaa cgtacattgg ttatggcccc atctagcgtt ggcttgggtg    4380
ccgtgttctt cgtaccgaat agccgattca ttttggctgg ctaggtgtga ggattggaag    4440
tgaactcttg tggcaagctt gaggtcttga acaggcaccg aactgggggg tagatatggt    4500
ctggttggtc ttagcggccg cggcctcgcc gccttggaga taccggtcgg gagtatagag    4560
ctgtgtcggg tgtttctgtg agttgggact ttgtgcaaac gaagtcttca gagattgcaa    4620
gagacgagac tgatagtgag cgccagtgag gatgtgagta gtccagtaat aatttcaact    4680
attagaaaag aatatggagt agcggggtgg atgttatcag ttgcgctcga gacgaagctt    4740
aggctgctac ctagaattgc ccccacgtga tggggtataa tacagtaaga tgtggtaata    4800
tcctgaaggt acggctatgt gccgttctgg ttaaattggt cagtgtaat                 4849
```

<210> SEQ ID NO 2
<211> LENGTH: 575
<212> TYPE: PRT
<213> ORGANISM: Aspergillus niger

<400> SEQUENCE: 2

```
Met Asn Cys Pro Ser Arg Thr Asp Asp Thr Leu Glu His Pro Gly Trp
  1               5                  10                  15

Asn Gln Asn Pro Pro Ala Leu Asn Ala Asp Ile Thr Thr Arg Ser Asp
             20                  25                  30

Phe Asn Gly Ile Ala Asn Ser Lys Val His Arg Arg His Ala Gly Gly
         35                  40                  45

Met Gly Gly Ala Ala Ala Glu Gly Ile Ala Ala Met Asp His Arg Pro
     50                  55                  60

Asn Ser Leu Asp Gly Asn Glu Pro Glu Met Glu Lys Lys Thr Pro Gly
 65                  70                  75                  80

Glu Val Ile Ala Ala Pro Gly Asp Gln Ser Pro Arg Thr Ser Ser
             85                  90                  95

Glu Ser Pro Arg Arg Pro Phe Lys Lys Ser Thr Ile Ser Phe Phe Leu
            100                 105                 110

Arg Leu Ala Gln Ser Ile Lys Lys Phe Arg Phe Val Gly Pro Gly
        115                 120                 125

Phe Leu Ile Ala Val Ala Tyr Ile Asp Pro Gly Asn Tyr Ser Thr Asp
    130                 135                 140

Val Ala Ala Gly Ala Glu Phe Arg Tyr Ala Leu Leu Phe Ile Val Leu
145                 150                 155                 160

Val Ser Asn Leu Phe Ala Ile Phe Leu Gln Ser Leu Cys Ile Lys Leu
                165                 170                 175
```

Gly Thr Val Thr Gly Leu Asn Leu Ala Glu Asn Cys Arg Glu His Leu
            180                 185                 190

Pro Lys Trp Leu Asn Tyr Ile Leu Tyr Val Phe Ala Glu Ala Ala Ile
            195                 200                 205

Val Ala Thr Asp Ile Ala Glu Val Val Gly Ser Ala Ile Ser Leu Asn
210                 215                 220

Leu Leu Leu Lys Ile Pro Leu Val Ala Gly Cys Ala Ile Thr Leu Ala
225                 230                 235                 240

Asp Val Leu Phe Ile Leu Ile Phe Tyr Arg Pro Asn Gly Ala Met Trp
            245                 250                 255

Gly Leu Arg Leu Phe Glu Phe Phe Val Met Leu Leu Val Leu Gly Val
            260                 265                 270

Val Ile Cys Phe Cys Ile Gln Leu Ala Leu Ile Lys Glu Gln Ser Val
            275                 280                 285

Gly Ala Val Phe Arg Gly Tyr Leu Pro Ser Ser Ala Ile Val Gln Ser
            290                 295                 300

Asn Gly Leu Tyr Gln Ser Cys Gly Ile Leu Gly Ala Thr Val Met Pro
305                 310                 315                 320

His Ser Met Phe Leu Gly Ser Gly Val Val Gln Ser Arg Leu Lys Glu
            325                 330                 335

Phe Asp Val Thr Gln Gly Tyr Val Asp Pro Ser Val Cys Leu Gly Ser
            340                 345                 350

Thr Asn Gly Glu Val Glu Tyr Arg Pro Ser Ile Gln Ala Ile Arg Gly
            355                 360                 365

Cys Leu Lys Tyr Ser Val Ile Glu Leu Thr Leu Ser Leu Phe Thr Phe
370                 375                 380

Ala Leu Phe Val Asn Ser Ala Ile Leu Ile Val Ala Gly Ala Ser Leu
385                 390                 395                 400

Tyr Gly Thr Ser Gly Ala Asp Glu Ala Asp Leu Trp Gly Ile Tyr Asn
            405                 410                 415

Leu Leu Ser Ser Ser Ile Ala Pro Ala Ala Gly Leu Ile Phe Ala Leu
            420                 425                 430

Ala Leu Leu Leu Ser Gly Ile Ser Ala Gly Ile Val Cys Thr Met Ala
            435                 440                 445

Gly Gln Met Val Ser Glu Gly Met Leu Asn Trp Ser Ile Arg Pro Trp
450                 455                 460

Leu Arg Arg Leu Val Thr Arg Ser Ile Ser Ile Pro Ser Ile Ile
465                 470                 475                 480

Ile Ala Ala Ala Val Gly Lys Glu Gly Leu Asn Lys Thr Leu Asn Ala
            485                 490                 495

Ser Gln Val Val Leu Ser Val Ile Leu Pro Phe Val Thr Ala Pro Leu
            500                 505                 510

Val Tyr Phe Thr Cys Arg Asn Arg Tyr Met Thr Val Pro Thr Asp Arg
            515                 520                 525

Asn Phe Thr Gly Glu Asp Ser Ser Ala Asp Gly Val Lys Met Arg Asn
530                 535                 540

Asn Trp Leu Val Thr Ala Ile Ala Val Ile Val Trp Val Ile Ile Ala
545                 550                 555                 560

Val Met Asn Val Ala Leu Leu Ile Leu Ile Gly Leu Gly Lys Ala
            565                 570                 575

<210> SEQ ID NO 3
<211> LENGTH: 20
<212> TYPE: DNA

```
<213> ORGANISM: Artificial Sequence
<220> FEATURE:
<223> OTHER INFORMATION: primer

<400> SEQUENCE: 3
ataattttgt aagctataag                                                       20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
attacactga ccaatttaac                                                       20

<210> SEQ ID NO 5
<211> LENGTH: 1728
<212> TYPE: DNA
<213> ORGANISM: Aspergillus niger
<220> FEATURE:
<221> NAME/KEY: CDS
<222> LOCATION: (1)..(1728)

<400> SEQUENCE: 5
```

| | | | | | | | | | | | | | | | | |
|---|---|---|---|---|---|---|---|---|---|---|---|---|---|---|---|---|
| atg | aat | tgt | cct | tcg | cgc | acc | gat | gac | acc | ctc | gag | cac | ccg | gga | tgg | 48 |
| Met | Asn | Cys | Pro | Ser | Arg | Thr | Asp | Asp | Thr | Leu | Glu | His | Pro | Gly | Trp | |
| 1 | | | 5 | | | | | 10 | | | | | 15 | | | |
| aac | cag | aat | ccg | ccg | gcg | ctg | aat | gcc | gac | att | acc | act | cga | agc | gac | 96 |
| Asn | Gln | Asn | Pro | Pro | Ala | Leu | Asn | Ala | Asp | Ile | Thr | Thr | Arg | Ser | Asp | |
| | | 20 | | | | | 25 | | | | | 30 | | | | |
| ttc | aac | ggc | att | gcg | aac | tcg | aag | gtg | cat | cgg | aga | cat | gca | ggc | ggt | 144 |
| Phe | Asn | Gly | Ile | Ala | Asn | Ser | Lys | Val | His | Arg | Arg | His | Ala | Gly | Gly | |
| 35 | | | | | 40 | | | | | 45 | | | | | | |
| atg | gga | ggg | gct | gca | gct | gaa | ggt | att | gcg | gcg | atg | gat | cat | aga | cca | 192 |
| Met | Gly | Gly | Ala | Ala | Ala | Glu | Gly | Ile | Ala | Ala | Met | Asp | His | Arg | Pro | |
| 50 | | | | | 55 | | | | | 60 | | | | | | |
| aat | agt | cta | gat | gga | aac | gag | ccc | gag | atg | gag | aag | aag | aca | ccc | ggc | 240 |
| Asn | Ser | Leu | Asp | Gly | Asn | Glu | Pro | Glu | Met | Glu | Lys | Lys | Thr | Pro | Gly | |
| 65 | | | | | 70 | | | | | 75 | | | | | 80 | |
| gaa | gtg | att | gct | gcc | gct | cct | ggg | gac | caa | tca | ccc | agg | acg | agc | agc | 288 |
| Glu | Val | Ile | Ala | Ala | Ala | Pro | Gly | Asp | Gln | Ser | Pro | Arg | Thr | Ser | Ser | |
| | | | | 85 | | | | | 90 | | | | | 95 | | |
| gaa | tca | cct | cgc | cgt | cct | ttc | aaa | aaa | tca | act | ata | tct | ttc | ttt | ctc | 336 |
| Glu | Ser | Pro | Arg | Arg | Pro | Phe | Lys | Lys | Ser | Thr | Ile | Ser | Phe | Phe | Leu | |
| | | | 100 | | | | | 105 | | | | | 110 | | | |
| cgt | cta | gct | caa | agt | atc | aag | aag | ttt | ggt | cgc | ttc | gtg | ggc | cct | gga | 384 |
| Arg | Leu | Ala | Gln | Ser | Ile | Lys | Lys | Phe | Gly | Arg | Phe | Val | Gly | Pro | Gly | |
| | | 115 | | | | | 120 | | | | | 125 | | | | |
| ttc | ctg | atc | gcg | gta | gcc | tac | att | gat | ccg | gga | aac | tac | tcc | acc | gat | 432 |
| Phe | Leu | Ile | Ala | Val | Ala | Tyr | Ile | Asp | Pro | Gly | Asn | Tyr | Ser | Thr | Asp | |
| 130 | | | | | 135 | | | | | 140 | | | | | | |
| gtc | gcc | gca | ggc | gcg | gag | ttt | cgc | tat | gct | ttg | ctc | ttc | atc | gtc | cta | 480 |
| Val | Ala | Ala | Gly | Ala | Glu | Phe | Arg | Tyr | Ala | Leu | Leu | Phe | Ile | Val | Leu | |
| 145 | | | | | 150 | | | | | 155 | | | | | 160 | |
| gtg | tcc | aac | ctt | ttt | gct | att | ttt | cta | cag | tcg | ctg | tgt | atc | aaa | ctc | 528 |
| Val | Ser | Asn | Leu | Phe | Ala | Ile | Phe | Leu | Gln | Ser | Leu | Cys | Ile | Lys | Leu | |
| | | | | 165 | | | | | 170 | | | | | 175 | | |
| ggc | aca | gtg | aca | ggg | ctc | aat | ctg | gcg | gaa | aac | tgc | agg | gag | cat | ctg | 576 |
| Gly | Thr | Val | Thr | Gly | Leu | Asn | Leu | Ala | Glu | Asn | Cys | Arg | Glu | His | Leu | |
| | | | 180 | | | | | 185 | | | | | 190 | | | |
| ccc | aag | tgg | ttg | aac | tac | atc | ctg | tat | gtt | ttt | gcg | gag | gcc | gcc | atc | 624 |

```
        Pro Lys Trp Leu Asn Tyr Ile Leu Tyr Val Phe Ala Glu Ala Ala Ile
            195                 200                 205 gtg gca acc gat atc gca gag gtt gtc ggg tct gcg att tcg ctc aac        672
Val Ala Thr Asp Ile Ala Glu Val Val Gly Ser Ala Ile Ser Leu Asn
210                 215                 220 ctt ctc ctg aaa atc cct ctg gtg gct gga tgc gca atc aca tta gcc        720
Leu Leu Leu Lys Ile Pro Leu Val Ala Gly Cys Ala Ile Thr Leu Ala
225                 230                 235                 240 gat gtt ctt ttc atc ctg ata ttc tac cga ccg aat ggc gcc atg tgg        768
Asp Val Leu Phe Ile Leu Ile Phe Tyr Arg Pro Asn Gly Ala Met Trp
                245                 250                 255 gga ctg cgt cta ttc gag ttc ttc gtc atg ctg ttg gtt ctg gga gtt        816
Gly Leu Arg Leu Phe Glu Phe Phe Val Met Leu Leu Val Leu Gly Val
            260                 265                 270 gtc ata tgc ttt tgc atc cag ctt gcc ctt atc aaa gaa cag tcg gtc        864
Val Ile Cys Phe Cys Ile Gln Leu Ala Leu Ile Lys Glu Gln Ser Val
        275                 280                 285 gga gct gtt ttc cgg ggc tac ttg cct tcg tct gcc ata gtg cag tcc        912
Gly Ala Val Phe Arg Gly Tyr Leu Pro Ser Ser Ala Ile Val Gln Ser
    290                 295                 300 aat ggt ctg tat caa agc tgt ggt atc ctc ggt gct aca gtg atg cct        960
Asn Gly Leu Tyr Gln Ser Cys Gly Ile Leu Gly Ala Thr Val Met Pro
305                 310                 315                 320 cac tcc atg ttt ctt ggc agc gga gtt gtc caa tcg cga ctg aag gaa       1008
His Ser Met Phe Leu Gly Ser Gly Val Val Gln Ser Arg Leu Lys Glu
                325                 330                 335 ttc gat gtt acc caa ggc tac gtc gat ccc tcc gtc tgc ctt gga agc       1056
Phe Asp Val Thr Gln Gly Tyr Val Asp Pro Ser Val Cys Leu Gly Ser
            340                 345                 350 acc aac gga gaa gtg gaa tac agg ccg tca atc cag gcg att agg ggc       1104
Thr Asn Gly Glu Val Glu Tyr Arg Pro Ser Ile Gln Ala Ile Arg Gly
        355                 360                 365 tgt ctg aag tat tcc gtc att gag ctt acg ttg tcc ctt ttt aca ttt       1152
Cys Leu Lys Tyr Ser Val Ile Glu Leu Thr Leu Ser Leu Phe Thr Phe
    370                 375                 380 gcc ctc ttc gtc aac agc gcc att ctc ata gtt gct ggt gct tcc ctg       1200
Ala Leu Phe Val Asn Ser Ala Ile Leu Ile Val Ala Gly Ala Ser Leu
385                 390                 395                 400 tac gga acg tcg gga gct gat gaa gca gac ctc tgg ggc atc tac aat       1248
Tyr Gly Thr Ser Gly Ala Asp Glu Ala Asp Leu Trp Gly Ile Tyr Asn
                405                 410                 415 ctt ctc tcc agc tcc att gct ccg gct gca ggt ctt atc ttt gca ctg       1296
Leu Leu Ser Ser Ser Ile Ala Pro Ala Ala Gly Leu Ile Phe Ala Leu
            420                 425                 430 gcc cta ctt ctc tca ggt atc tcg gcc ggc att gtc tgt acc atg gct       1344
Ala Leu Leu Leu Ser Gly Ile Ser Ala Gly Ile Val Cys Thr Met Ala
        435                 440                 445 ggg caa atg gtt agc gag gga atg ctg aac tgg agc atc aga cct tgg       1392
Gly Gln Met Val Ser Glu Gly Met Leu Asn Trp Ser Ile Arg Pro Trp
    450                 455                 460 ctt cgc cga ctg gtc acg cgg tcc atc agt atc atc cct agc ata atc       1440
Leu Arg Arg Leu Val Thr Arg Ser Ile Ser Ile Ile Pro Ser Ile Ile
465                 470                 475                 480 att gca gct gct gtc ggc aag gag gga ttg aac aaa act ctc aac gcc       1488
Ile Ala Ala Ala Val Gly Lys Glu Gly Leu Asn Lys Thr Leu Asn Ala
                485                 490                 495 agt caa gtg gta ttg agt gtc atc ctt ccg ttt gtc acc gct cct cta       1536
Ser Gln Val Val Leu Ser Val Ile Leu Pro Phe Val Thr Ala Pro Leu
            500                 505                 510 gtt tac ttt acg tgc cgc aac cgt tac atg act gtt cct acg gac aga       1584
```

| | | | | | | | | | | | | | | |
|---|---|---|---|---|---|---|---|---|---|---|---|---|---|---|
| Val | Tyr | Phe | Thr | Cys | Arg | Asn | Arg | Tyr | Met | Thr | Val | Pro | Thr | Asp | Arg |
| | 515 | | | | | 520 | | | | | 525 | | | | |

| aac | ttc | act | ggc | gag | gat | tcc | tcg | gct | gac | gga | gtc | aag | atg | aga | aac | 1632 |
|---|---|---|---|---|---|---|---|---|---|---|---|---|---|---|---|---|
| Asn | Phe | Thr | Gly | Glu | Asp | Ser | Ser | Ala | Asp | Gly | Val | Lys | Met | Arg | Asn | |
| 530 | | | | | 535 | | | | | 540 | | | | | | |

| aac | tgg | ctt | gtt | act | gcc | atc | gct | gtc | att | gtt | tgg | gta | atc | att | gcg | 1680 |
|---|---|---|---|---|---|---|---|---|---|---|---|---|---|---|---|---|
| Asn | Trp | Leu | Val | Thr | Ala | Ile | Ala | Val | Ile | Val | Trp | Val | Ile | Ile | Ala | |
| 545 | | | | 550 | | | | | 555 | | | | | 560 | | |

| gtc | atg | aac | gtt | gct | ttg | ctc | atc | ctt | att | ggg | ctc | ggc | aaa | gcc | tga | 1728 |
|---|---|---|---|---|---|---|---|---|---|---|---|---|---|---|---|---|
| Val | Met | Asn | Val | Ala | Leu | Leu | Ile | Leu | Ile | Gly | Leu | Gly | Lys | Ala | | |
| | | | | 565 | | | | | 570 | | | | | 575 | | |

<210> SEQ ID NO 6
<211> LENGTH: 5492
<212> TYPE: DNA
<213> ORGANISM: Aspergillus niger

<400> SEQUENCE: 6

| | | | | | |
|---|---|---|---|---|---|
| gtactcccta | ctctggtact | gatatatctt | ccggcttagg | agaccatttg | gatcttgact | 60 |
| ttggagaacc | tggattattg | ttttccaacc | cgattggtat | ggatgctaca | gacacatatt | 120 |
| ccattgattc | tgcgatggaa | agctttctcg | ccgaatttgt | ccgcggagac | tggggctggg | 180 |
| acccattctc | aggcacaacg | gctttgtgaa | agcacatcag | cctgttatca | cggtcgctcc | 240 |
| cacctcataa | ggcttttgt | cgactggaac | cgacagacta | tataaaacga | ataccacagt | 300 |
| gtgtctctca | tatactatac | attccggtac | atttcataga | ggcaccaata | tgtattctaa | 360 |
| atcacgagtc | tgcgagaagg | gatatattgc | ccttgaaaaa | caaacaacg | aaacaagctg | 420 |
| gaactcagga | cctgtctatt | tcctcagcct | cttgatagtg | ctccctatttt | catcaccccg | 480 |
| ttccaggcaa | cgccgtgtct | cctcatcaat | ttcaaagcgt | tcctggcaga | gttgtacaca | 540 |
| ctcttctgcc | ttttcaggcg | gaacgaccac | cacccccatct | gcatctccaa | ggatataatc | 600 |
| accaggattg | atgacaacct | gccctccatt | ttctgaattc | ttatagataa | ccggtacatc | 660 |
| caattcagag | gagcgagtga | agtattaga | tccaaggatg | ctaatgccgc | gcgcaaacag | 720 |
| ggtcattccc | agctcgcggt | gctcattgat | atcacgaaat | ttgccatcaa | tgatgactcc | 780 |
| ggcggcacca | cgtttctgag | cccgagtgct | catgagtcct | ccccaacaag | cactgattaa | 840 |
| gcctttgggt | tgtgacacaa | atacaacact | gtctttgggg | atggcatcgg | cgaagtgaac | 900 |
| ctttggcgtt | ggcgaagcct | tgtccgaggc | atgcaccatt | ttcactgtgt | atgccgggcc | 960 |
| gaggaacttt | gctgtgggtg | acatgaaatc | cggagagtac | attttaaggc | cggataaata | 1020 |
| gccgccctga | gagactccaa | gcttgacgag | tgcatcgccg | acctgaaggg | attggttgag | 1080 |
| ctctagccag | aattgcgccg | aatagtgtat | cttacatcac | aggaggtgaa | gcgccgcaac | 1140 |
| gcgctgagga | cgtttggtct | aatagccata | gttgcttgtc | cgcgattgaa | tcgatggtac | 1200 |
| aggataagat | acaaatgggc | aagacggtcg | ccacagaagg | tagatagaag | tggtggccag | 1260 |
| cttcaaaagc | ggggagacaa | tcggaccatc | cgacggatga | tcccgtattc | tggagtagcc | 1320 |
| cggggcatgc | tttcgcactg | tcggatagct | ccgaagccag | atccggagta | gtcccgctct | 1380 |
| tttgcctcgg | ccgcgacag | agcttgacct | acgcgaacca | tgactgcttt | cgaggaatat | 1440 |
| tctttgtaac | tttctatact | caatggttaa | ccttcatacc | acgatactca | agccagcaca | 1500 |
| atgcagcgat | gtcgccaaaa | attaccggtg | atgcaagcat | cataccgatc | cctctgcctg | 1560 |
| aacggagctc | ggagctatgc | gacaaccgtt | ccaggtaacc | cagtcagtac | acctcgatct | 1620 |
| cagtccagag | catttggtgc | tgattttggc | cgttgaacag | attctaggcg | ttcactaccc | 1680 |
| caaacagatt | cgggccatcg | aagcgattaa | gcagggatca | aagcgcccgc | tcacgcttgc | 1740 |

```
tgaaaagaca ctatacagtc acttactgga cacggatagc ggtcgttgga acattgataa    1800
gattacgcgg ggaaagacca ttttggagct acgccctgat cgtgttgcct gccatgatgc    1860
gactgcaaca atggctttac tacagtttat cagcgctggc ctcccgcgtg tgatggtacc    1920
gacaacagtg cacagcgatc atcttattat ctcagagaat ggcgcggaga agatatgca    1980 gcgtgcgacc acagaacacg cagaggtata tgatttcttg agtagcgctt cgaagaagta    2040
cgggatcggc ttctggaagc ctggatctgg aatcatccat actgtcattt ttgagaacta    2100
cgcgatgtat gtctaccaca tgaagaccgc aattaccatc actgacaatt ttgggacata    2160
ggcctggagg tttgattatc ggtacggatt ctcatacgcc caatgcaggt gggatgggca    2220
tgcttggaat tggcgttggc ggagccgatg ctgttgacgc aatgtcgggg atggcttggg    2280
agttggttgc gccgaaagtc attggagtcg aacttacggg cgagcttcaa ggttgggcgt    2340
caacaaaaga tattatctgt aaactggcag gaatactcag tgtatcgggc gggaaaggtc    2400
gcatcattga attcttcggt cctggtacga agaccctggg cgcgacagct atggctacca    2460
tttgcaacat gtctgcggaa attgggtcga cttcttgtat cttcccctac tcggatgcga    2520
tcgcccgcta tttgagtgcc actgcgcgcg atcatgttgt gaaagcggca aactcagtca    2580
aagaccttct actcaccgca gatgagggct ccgaggagta ctacgacgaa atcatcaaga    2640
tcgatttgga cactctggag ccgcatgtta acggtccttt cacaccggat ctagctcatc    2700
ccatctcgaa gctgtctact gcggtcgctg agagcgattg gcctgtgaac ctaagccacg    2760
ccatggtggg tagctgtacc aacagctcct atgaggattt ggacaaggct cggcagctgg    2820
ttaaccaagc ccgggcggcc ggaataacaa agttcaagac tcctttcttg gtttcaccag    2880
gtagcgaaag aattcgggct accgccgagg aggctggtat cctgcaggat ctcgaggacg    2940
ctggtgctat gatcctcagc agctcttgcg gaccgtgtgt cgggtcgtgg gaccgcaagg    3000
acgtggatgt ccgcggaaaa gagaagaact cggtgatctc cagctacaac cgtaactttg    3060
tggggcgcca cgacagcaat ccggccacgc actcattcgt cacgtcgccg gagctagtca    3120
cagcctttgc ttatgctggt cgcctggact ttaaccctgt cactgacagt atctctgcgg    3180
aaggatctca gccactgcgg cttacgcctc ctgtaggtca ggaattgcca gaatcattca    3240
attccggtgc agatcgcttt caagagcctc cgtcagatgg ctcatcctac tcggttatta    3300
tcgatgagaa gtccgacagg ctacaactct tgaagccctt cccggcgtgg aagcacggaa    3360
atgcaacgga catggagttg ctgatgaagg taaagggcaa gtgtacgacg gatcacatat    3420
ccccggctgg cccgtggtac aaatatcgcg gtcatctgga gaacatcagc cacaacatgc    3480
tcaccaccgc aaccaatgca ttcttagaca atgacccgca aatgctaggc catacgacac    3540
atccgctaac gcgcaaggtc cagcttactc atgaagtggc ccgagacttg aagcaccgtt    3600
ccattcgttg gtgcgtggtt ggagacaaca actacggtga gggtagttcg cgagagcatg    3660
ccgcactgga gcctcgcttc ctcggtggca ttgccatcat agcccggtct ttcgctcgta    3720
tccacgagac gaatctgaag aaacagggaa tgcttccgct cacattcgct gatcctgctg    3780
actacgaccg agtgcaggag ggagatcgca tcactctgat tggcgtagaa gatggagagc    3840
tgcaaccggg gaagaatgtc accatgcggg ttactccgcg ccatggagac gcctgggagg    3900
ctgagttgtg ccacagctat catgccggac agctcccgtg gctccgggct ggtagtgcct    3960
tgaaccatat caaggctact gtacgcagct gagtgggttt ttgcatagaa tgataaatag    4020
attcaatgta cagaaaggtt tttatataca aagacaaatg ttacttggac tcacaccctg    4080
ccgaacggac tttacagcta gcctttttga aggtcttctc tttgtgattc tctcgaacac    4140
```

```
aatcttacct cagtaggaaa ctgagacttg tattaatctt accttctcaa ttactctgaa    4200
acctgtctcc gtagcagctt cgtagcgtcc gcctagtgcc cctggagctg tccccaatag    4260
gtgctttagg tgatcgtctt gcaggtgccg tacaaggtgc cttagatgac gcattagaaa    4320
atgctttagg ggttcccctt agatagtgcc ttggagatgg tcttagagat ggcctggggg    4380
tagcctgaag gcagtcttag aggtagtctt gagcataccc atttacagca ttcgactgaa    4440
agtgttttac ataaccagct tatgaatgat atcttggtta gctctattta ggcatgattg    4500
caaagtccgt ttggcagagt ggagtccaaa tggcagccgc ctatataaat gccgtatctc    4560
tcatcttata cggtatcccc taggttccac aagagtggcg ttcctactga agcacctccc    4620
tcattggtgg taccaaaatt gcaccatgtc aatgcgcggg aaatgcttct catggacagc    4680
tccggccacc cggagtagcc caagatatgc cccggattga ctccgcattc cccagacttg    4740
gcaggaaggg gatgacatcc gactagattg gattggctaa tgcccaccat cttgcagatg    4800
tggactgatt atgcctttgg ttgcataggc tgtgatatcc tggggtattt agtagatccc    4860
tctgcctgtg ttgtcaatct atctcatgct ggcagcccag gtctggtaac tagggatctc    4920
tcggtgtcga gcaatacgcc caaaacttac tttctccgtt caatatggga gcagcaggcg    4980
gcggtttctc cccccaagcc atcaaacaag tccctcctgc ggctcgagga ctttacatct    5040
ggttggcgat catctgggcc tcgtactgcg gtggtctgca tggttttaac acgtccaata    5100
tctcgggtgc tatgcagatg gagcaatggg atccagactt ggatgggac aagctttcca     5160 gcacgactgt ttcgaacaat gagggctggg tggtatcctc tatgctgctg gtatgtgatc    5220
tcacactata tagcatgaag tgcatttact gaggcagtat aactttatgc agggccaaac    5280
cgtcggagtc ttattcgcag gcccactagg ggaacgacgg ggccgaaagg cagtcatcct    5340
cgctgccgcc atctgctact cgatcggagc tattctcatg gctgccaacc tggggtcctt    5400
cgctgaactc ctggtcgggc gtattctttc cggattaggg tctggactgg gaatgtcagc    5460
aggaccggta tacatctccg aagttgcacc cc                                    5492
```

<210> SEQ ID NO 7
<211> LENGTH: 792
<212> TYPE: PRT
<213> ORGANISM: Aspergillus niger
<400> SEQUENCE: 7

```
Met Gln Arg Cys Arg Gln Lys Leu Pro Val Met Gln Ala Ser Tyr Arg
1               5                   10                  15

Ser Leu Cys Leu Asn Gly Ala Arg Ser Tyr Ala Thr Thr Val Pro Gly
            20                  25                  30

Asn Pro Ile Leu Gly Val His Tyr Pro Lys Gln Ile Arg Ala Ile Glu
        35                  40                  45

Ala Ile Lys Gln Gly Ser Lys Arg Pro Leu Thr Leu Ala Glu Lys Thr
    50                  55                  60

Leu Tyr Ser His Leu Leu Asp Thr Asp Ser Gly Arg Trp Asn Ile Asp
65                  70                  75                  80

Lys Ile Thr Arg Gly Lys Thr Ile Leu Glu Leu Arg Pro Asp Arg Val
                85                  90                  95

Ala Cys His Asp Ala Thr Ala Thr Met Ala Leu Leu Gln Phe Ile Ser
            100                 105                 110

Ala Gly Leu Pro Arg Val Met Val Pro Thr Thr Val His Ser Asp His
        115                 120                 125

Leu Ile Ile Ser Glu Asn Gly Ala Glu Lys Asp Met Gln Arg Ala Thr
```

-continued

```
            130                 135                 140
Thr Glu His Ala Glu Val Tyr Asp Phe Leu Ser Ser Ala Ser Lys Lys
145                 150                 155                 160

Tyr Gly Ile Gly Phe Trp Lys Pro Gly Ser Gly Ile Ile His Thr Val
                165                 170                 175

Ile Phe Glu Asn Tyr Ala Met Pro Gly Gly Leu Ile Ile Gly Thr Asp
                180                 185                 190

Ser His Thr Pro Asn Ala Gly Gly Met Gly Met Leu Gly Ile Gly Val
                195                 200                 205

Gly Gly Ala Asp Ala Val Asp Ala Met Ser Gly Met Ala Trp Glu Leu
210                 215                 220

Val Ala Pro Lys Val Ile Gly Val Glu Leu Thr Gly Glu Leu Gln Gly
225                 230                 235                 240

Trp Ala Ser Thr Lys Asp Ile Ile Cys Lys Leu Ala Gly Ile Leu Ser
                245                 250                 255

Val Ser Gly Gly Lys Gly Arg Ile Ile Glu Phe Phe Gly Pro Gly Thr
                260                 265                 270

Lys Thr Leu Gly Ala Thr Ala Met Ala Thr Ile Cys Asn Met Ser Ala
                275                 280                 285

Glu Ile Gly Ser Thr Ser Cys Ile Phe Pro Tyr Ser Asp Ala Ile Ala
290                 295                 300

Arg Tyr Leu Ser Ala Thr Ala Arg Asp His Val Val Lys Ala Ala Asn
305                 310                 315                 320

Ser Val Lys Asp Leu Leu Leu Thr Ala Asp Glu Gly Ser Glu Glu Tyr
                325                 330                 335

Tyr Asp Glu Ile Ile Lys Ile Asp Leu Asp Thr Leu Glu Pro His Val
                340                 345                 350

Asn Gly Pro Phe Thr Pro Asp Leu Ala His Pro Ile Ser Lys Leu Ser
                355                 360                 365

Thr Ala Val Ala Glu Ser Asp Trp Pro Val Asn Leu Ser His Ala Met
370                 375                 380

Val Gly Ser Cys Thr Asn Ser Ser Tyr Glu Asp Leu Asp Lys Ala Arg
385                 390                 395                 400

Gln Leu Val Asn Gln Ala Arg Ala Ala Gly Ile Thr Lys Phe Lys Thr
                405                 410                 415

Pro Phe Leu Val Ser Pro Gly Ser Glu Arg Ile Arg Ala Thr Ala Glu
                420                 425                 430

Glu Ala Gly Ile Leu Gln Asp Leu Glu Asp Ala Gly Ala Met Ile Leu
                435                 440                 445

Ser Ser Ser Cys Gly Pro Cys Val Gly Ser Trp Asp Arg Lys Asp Val
450                 455                 460

Asp Val Arg Gly Lys Glu Lys Asn Ser Val Ile Ser Ser Tyr Asn Arg
465                 470                 475                 480

Asn Phe Val Gly Arg His Asp Ser Asn Pro Ala Thr His Ser Phe Val
                485                 490                 495

Thr Ser Pro Glu Leu Val Thr Ala Phe Ala Tyr Ala Gly Arg Leu Asp
                500                 505                 510

Phe Asn Pro Val Thr Asp Ser Ile Ser Ala Glu Gly Ser Gln Pro Leu
                515                 520                 525

Arg Leu Thr Pro Pro Val Gly Gln Glu Leu Pro Glu Ser Phe Asn Ser
                530                 535                 540

Gly Ala Asp Arg Phe Gln Glu Pro Pro Ser Asp Gly Ser Ser Tyr Ser
545                 550                 555                 560
```

```
Val Ile Ile Asp Glu Lys Ser Asp Arg Leu Gln Leu Leu Lys Pro Phe
            565                 570                 575

Pro Ala Trp Lys His Gly Asn Ala Thr Asp Met Glu Leu Leu Met Lys
            580                 585                 590

Val Lys Gly Lys Cys Thr Thr Asp His Ile Ser Pro Ala Gly Pro Trp
            595                 600                 605

Tyr Lys Tyr Arg Gly His Leu Glu Asn Ile Ser His Asn Met Leu Thr
            610                 615                 620

Thr Ala Thr Asn Ala Phe Leu Asp Asn Asp Pro Gln Met Leu Gly His
625                 630                 635                 640

Thr Thr His Pro Leu Thr Arg Lys Val Gln Leu Thr His Glu Val Ala
            645                 650                 655

Arg Asp Leu Lys His Arg Ser Ile Arg Trp Cys Val Val Gly Asp Asn
            660                 665                 670

Asn Tyr Gly Glu Gly Ser Ser Arg Glu His Ala Ala Leu Glu Pro Arg
            675                 680                 685

Phe Leu Gly Gly Ile Ala Ile Ile Ala Arg Ser Phe Ala Arg Ile His
            690                 695                 700

Glu Thr Asn Leu Lys Lys Gln Gly Met Leu Pro Leu Thr Phe Ala Asp
705                 710                 715                 720

Pro Ala Asp Tyr Asp Arg Val Gln Glu Gly Asp Arg Ile Thr Leu Ile
            725                 730                 735

Gly Val Glu Asp Gly Glu Leu Gln Pro Gly Lys Asn Val Thr Met Arg
            740                 745                 750

Val Thr Pro Arg His Gly Asp Ala Trp Glu Ala Glu Leu Cys His Ser
            755                 760                 765

Tyr His Ala Gly Gln Leu Pro Trp Leu Arg Ala Gly Ser Ala Leu Asn
            770                 775                 780

His Ile Lys Ala Thr Val Arg Ser
785                 790

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gtactcccta ctctggtact                                              20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ggggtgcaac ttcggagatg                                              20

<210> SEQ ID NO 10
<211> LENGTH: 2379
<212> TYPE: DNA
<213> ORGANISM: Aspergillus niger
<220> FEATURE:
<221> NAME/KEY: CDS
<222> LOCATION: (1)..(2379)

<400> SEQUENCE: 10
```

```
atg cag cga tgt cgc caa aaa tta ccg gtg atg caa gca tca tac cga    48
Met Gln Arg Cys Arg Gln Lys Leu Pro Val Met Gln Ala Ser Tyr Arg
1               5                   10                  15 tcc ctc tgc ctg aac gga gct cgg agc tat gcg aca acc gtt cca ggt    96
Ser Leu Cys Leu Asn Gly Ala Arg Ser Tyr Ala Thr Thr Val Pro Gly
            20                  25                  30 aac cca att cta ggc gtt cac tac ccc aaa cag att cgg gcc atc gaa   144
Asn Pro Ile Leu Gly Val His Tyr Pro Lys Gln Ile Arg Ala Ile Glu
        35                  40                  45 gcg att aag cag gga tca aag cgc ccg ctc acg ctt gct gaa aag aca   192
Ala Ile Lys Gln Gly Ser Lys Arg Pro Leu Thr Leu Ala Glu Lys Thr
    50                  55                  60 cta tac agt cac tta ctg gac acg gat agc ggt cgt tgg aac att gat   240
Leu Tyr Ser His Leu Leu Asp Thr Asp Ser Gly Arg Trp Asn Ile Asp
65                  70                  75                  80 aag att acg cgg gga aag acc att ttg gag cta cgc cct gat cgt gtt   288
Lys Ile Thr Arg Gly Lys Thr Ile Leu Glu Leu Arg Pro Asp Arg Val
                85                  90                  95 gcc tgc cat gat gcg act gca aca atg gct tta cta cag ttt atc agc   336
Ala Cys His Asp Ala Thr Ala Thr Met Ala Leu Leu Gln Phe Ile Ser
            100                 105                 110 gct ggc ctc ccg cgt gtg atg gta ccg aca aca gtg cac agc gat cat   384
Ala Gly Leu Pro Arg Val Met Val Pro Thr Thr Val His Ser Asp His
        115                 120                 125 ctt att atc tca gag aat ggc gcg gag aaa gat atg cag cgt gcg acc   432
Leu Ile Ile Ser Glu Asn Gly Ala Glu Lys Asp Met Gln Arg Ala Thr
    130                 135                 140 aca gaa cac gca gag gta tat gat ttc ttg agt agc gct tcg aag aag   480
Thr Glu His Ala Glu Val Tyr Asp Phe Leu Ser Ser Ala Ser Lys Lys
145                 150                 155                 160 tac ggg atc ggc ttc tgg aag cct gga tct gga atc atc cat act gtc   528
Tyr Gly Ile Gly Phe Trp Lys Pro Gly Ser Gly Ile Ile His Thr Val
                165                 170                 175 att ttt gag aac tac gcg atg cct gga ggt ttg att atc ggt acg gat   576
Ile Phe Glu Asn Tyr Ala Met Pro Gly Gly Leu Ile Ile Gly Thr Asp
            180                 185                 190 tct cat acg ccc aat gca ggt ggg atg ggc atg ctt gga att ggc gtt   624
Ser His Thr Pro Asn Ala Gly Gly Met Gly Met Leu Gly Ile Gly Val
        195                 200                 205 ggc gga gcc gat gct gtt gac gca atg tcg ggg atg gct tgg gag ttg   672
Gly Gly Ala Asp Ala Val Asp Ala Met Ser Gly Met Ala Trp Glu Leu
    210                 215                 220 gtt gcg ccg aaa gtc att gga gtc gaa ctt acg ggc gag ctt caa ggt   720
Val Ala Pro Lys Val Ile Gly Val Glu Leu Thr Gly Glu Leu Gln Gly
225                 230                 235                 240 tgg gcg tca aca aaa gat att atc tgt aaa ctg gca gga ata ctc agt   768
Trp Ala Ser Thr Lys Asp Ile Ile Cys Lys Leu Ala Gly Ile Leu Ser
                245                 250                 255 gta tcg ggc ggg aaa ggt cgc atc att gaa ttc ttc ggt cct ggt acg   816
Val Ser Gly Gly Lys Gly Arg Ile Ile Glu Phe Phe Gly Pro Gly Thr
            260                 265                 270 aag acc ctg ggc gcg aca gct atg gct acc att tgc aac atg tct gcg   864
Lys Thr Leu Gly Ala Thr Ala Met Ala Thr Ile Cys Asn Met Ser Ala
        275                 280                 285 gaa att ggg tcg act tct tgt atc ttc ccc tac tcg gat gcg atc gcc   912
Glu Ile Gly Ser Thr Ser Cys Ile Phe Pro Tyr Ser Asp Ala Ile Ala
    290                 295                 300 cgc tat ttg agt gcc act gcg cgc gat cat gtt gtg aaa gcg gca aac   960
Arg Tyr Leu Ser Ala Thr Ala Arg Asp His Val Val Lys Ala Ala Asn
305                 310                 315                 320
```

```
tca gtc aaa gac ctt cta ctc acc gca gat gag ggc tcc gag gag tac    1008
Ser Val Lys Asp Leu Leu Leu Thr Ala Asp Glu Gly Ser Glu Glu Tyr
            325                 330                 335 tac gac gaa atc atc aag atc gat ttg gac act ctg gag ccg cat gtt    1056
Tyr Asp Glu Ile Ile Lys Ile Asp Leu Asp Thr Leu Glu Pro His Val
            340                 345                 350 aac ggt cct ttc aca ccg gat cta gct cat ccc atc tcg aag ctg tct    1104
Asn Gly Pro Phe Thr Pro Asp Leu Ala His Pro Ile Ser Lys Leu Ser
            355                 360                 365 act gcg gtc gct gag agc gat tgg cct gtg aac cta agc cac gcc atg    1152
Thr Ala Val Ala Glu Ser Asp Trp Pro Val Asn Leu Ser His Ala Met
        370                 375                 380 gtg ggt agc tgt acc aac agc tcc tat gag gat ttg gac aag gct cgg    1200
Val Gly Ser Cys Thr Asn Ser Ser Tyr Glu Asp Leu Asp Lys Ala Arg
385                 390                 395                 400 cag ctg gtt aac caa gcc cgg gcg gcc gga ata aca aag ttc aag act    1248
Gln Leu Val Asn Gln Ala Arg Ala Ala Gly Ile Thr Lys Phe Lys Thr
            405                 410                 415 cct ttc ttg gtt tca cca ggt agc gaa aga att cgg gct acc gcc gag    1296
Pro Phe Leu Val Ser Pro Gly Ser Glu Arg Ile Arg Ala Thr Ala Glu
            420                 425                 430 gag gct ggt atc ctg cag gat ctc gag gac gct ggt gct atg atc ctc    1344
Glu Ala Gly Ile Leu Gln Asp Leu Glu Asp Ala Gly Ala Met Ile Leu
            435                 440                 445 agc agc tct tgc gga ccg tgt gtc ggg tcg tgg gac cgc aag gac gtg    1392
Ser Ser Ser Cys Gly Pro Cys Val Gly Ser Trp Asp Arg Lys Asp Val
        450                 455                 460 gat gtc cgc gga aaa gag aag aac tcg gtg atc tcc agc tac aac cgt    1440
Asp Val Arg Gly Lys Glu Lys Asn Ser Val Ile Ser Ser Tyr Asn Arg
465                 470                 475                 480 aac ttt gtg ggg cgc cac gac agc aat ccg gcc acg cac tca ttc gtc    1488
Asn Phe Val Gly Arg His Asp Ser Asn Pro Ala Thr His Ser Phe Val
            485                 490                 495 acg tcg ccg gag cta gtc aca gcc ttt gct tat gct ggt cgc ctg gac    1536
Thr Ser Pro Glu Leu Val Thr Ala Phe Ala Tyr Ala Gly Arg Leu Asp
            500                 505                 510 ttt aac cct gtc act gac agt atc tct gcg gaa gga tct cag cca ctg    1584
Phe Asn Pro Val Thr Asp Ser Ile Ser Ala Glu Gly Ser Gln Pro Leu
            515                 520                 525 cgg ctt acg cct cct gta ggt cag gaa ttg cca gaa tca ttc aat tcc    1632
Arg Leu Thr Pro Pro Val Gly Gln Glu Leu Pro Glu Ser Phe Asn Ser
        530                 535                 540 ggt gca gat cgc ttt caa gag cct ccg tca gat ggc tca tcc tac tcg    1680
Gly Ala Asp Arg Phe Gln Glu Pro Pro Ser Asp Gly Ser Ser Tyr Ser
545                 550                 555                 560 gtt att atc gat gag aag tcc gac agg cta caa ctc ttg aag ccc ttc    1728
Val Ile Ile Asp Glu Lys Ser Asp Arg Leu Gln Leu Leu Lys Pro Phe
            565                 570                 575 ccg gcg tgg aag cac gga aat gca acg gac atg gag ttg ctg atg aag    1776
Pro Ala Trp Lys His Gly Asn Ala Thr Asp Met Glu Leu Leu Met Lys
            580                 585                 590 gta aag ggc aag tgt acg acg gat cac ata tcc ccg gct ggc ccg tgg    1824
Val Lys Gly Lys Cys Thr Thr Asp His Ile Ser Pro Ala Gly Pro Trp
            595                 600                 605 tac aaa tat cgc ggt cat ctg gag aac atc agc cac aac atg ctc acc    1872
Tyr Lys Tyr Arg Gly His Leu Glu Asn Ile Ser His Asn Met Leu Thr
            610                 615                 620 acc gca acc aat gca ttc tta gac aat gac ccg caa atg cta ggc cat    1920
Thr Ala Thr Asn Ala Phe Leu Asp Asn Asp Pro Gln Met Leu Gly His
625                 630                 635                 640
```

| | | | | | | | | | | | | | | | | |
|---|---|---|---|---|---|---|---|---|---|---|---|---|---|---|---|---|
| acg | aca | cat | ccg | cta | acg | cgc | aag | gtc | cag | ctt | act | cat | gaa | gtg | gcc | 1968 |
| Thr | Thr | His | Pro | Leu | Thr | Arg | Lys | Val | Gln | Leu | Thr | His | Glu | Val | Ala | |
| | | | | 645 | | | | | 650 | | | | | 655 | | |
| cga | gac | ttg | aag | cac | cgt | tcc | att | cgt | tgg | tgc | gtg | gtt | gga | gac | aac | 2016 |
| Arg | Asp | Leu | Lys | His | Arg | Ser | Ile | Arg | Trp | Cys | Val | Val | Gly | Asp | Asn | |
| | | | 660 | | | | | 665 | | | | | 670 | | | |
| aac | tac | ggt | gag | ggt | agt | tcg | cga | gag | cat | gcc | gca | ctg | gag | cct | cgc | 2064 |
| Asn | Tyr | Gly | Glu | Gly | Ser | Ser | Arg | Glu | His | Ala | Ala | Leu | Glu | Pro | Arg | |
| | | | 675 | | | | | 680 | | | | | 685 | | | |
| ttc | ctc | ggt | ggc | att | gcc | atc | ata | gcc | cgg | tct | ttc | gct | cgt | atc | cac | 2112 |
| Phe | Leu | Gly | Gly | Ile | Ala | Ile | Ile | Ala | Arg | Ser | Phe | Ala | Arg | Ile | His | |
| | | 690 | | | | | 695 | | | | | 700 | | | | |
| gag | acg | aat | ctg | aag | aaa | cag | gga | atg | ctt | ccg | ctc | aca | ttc | gct | gat | 2160 |
| Glu | Thr | Asn | Leu | Lys | Lys | Gln | Gly | Met | Leu | Pro | Leu | Thr | Phe | Ala | Asp | |
| 705 | | | | | 710 | | | | | 715 | | | | | 720 | |
| cct | gct | gac | tac | gac | cga | gtg | cag | gag | gga | gat | cgc | atc | act | ctg | att | 2208 |
| Pro | Ala | Asp | Tyr | Asp | Arg | Val | Gln | Glu | Gly | Asp | Arg | Ile | Thr | Leu | Ile | |
| | | | | 725 | | | | | 730 | | | | | 735 | | |
| ggc | gta | gaa | gat | gga | gag | ctg | caa | ccg | ggg | aag | aat | gtc | acc | atg | cgg | 2256 |
| Gly | Val | Glu | Asp | Gly | Glu | Leu | Gln | Pro | Gly | Lys | Asn | Val | Thr | Met | Arg | |
| | | | 740 | | | | | 745 | | | | | 750 | | | |
| gtt | act | ccg | cgc | cat | gga | gac | gcc | tgg | gag | gct | gag | ttg | tgc | cac | agc | 2304 |
| Val | Thr | Pro | Arg | His | Gly | Asp | Ala | Trp | Glu | Ala | Glu | Leu | Cys | His | Ser | |
| | | | 755 | | | | | 760 | | | | | 765 | | | |
| tat | cat | gcc | gga | cag | ctc | ccg | tgg | ctc | cgg | gct | ggt | agt | gcc | ttg | aac | 2352 |
| Tyr | His | Ala | Gly | Gln | Leu | Pro | Trp | Leu | Arg | Ala | Gly | Ser | Ala | Leu | Asn | |
| | | 770 | | | | | 775 | | | | | 780 | | | | |
| cat | atc | aag | gct | act | gta | cgc | agc | tga | | | | | | | | 2379 |
| His | Ile | Lys | Ala | Thr | Val | Arg | Ser | | | | | | | | | |
| 785 | | | | | 790 | | | | | | | | | | | |

<210> SEQ ID NO 11
<211> LENGTH: 5602
<212> TYPE: DNA
<213> ORGANISM: Aspergillus niger

<400> SEQUENCE: 11

| | | | | | |
|---|---|---|---|---|---|
| ggtggacgag | attttgtggt | gttgactcga | atccagtacg | ggaagaacag | gatacacgca | 60 |
| acagttttct | gttaatacta | tcgcttctca | agtatatggt | aaacgcgacc | ggatagtacc | 120 |
| actttcccaa | taagctgtta | ctactgggag | agatccagcg | cagctaaggt | ggcgatgatg | 180 |
| cttaagagag | gtatatcagc | aacctgcagg | gtcgtggcct | ctcgaatatg | atggaaaagt | 240 |
| gatttcctaa | gcggactttc | tggtcgtgtc | actacagact | ccacgagcgt | actctggcga | 300 |
| ccagggggc | cttccgccta | cagctggagc | acagccaagc | gatgctgtcc | agggccttgc | 360 |
| aactcgcgaa | cgagtacgtg | tacagagtac | gacctaaaaa | aagcgaagag | ctgagcgcaa | 420 |
| agaaaaagat | gcaaaggcgg | atattacaga | gttgccgact | ttgctgcaaa | aaagagtggg | 480 |
| gggatgagaa | acggtgcaga | agagatgaag | aaaggataga | aaggggagtt | gaaagggaag | 540 |
| ggatttcgta | gaaggtagta | aaggtggtca | gtcaggtgag | gagaaaaatc | agcatatatc | 600 |
| tgcgctaggc | tcgaaagggc | agcaacacct | aaaaacaagt | gaggtcgggt | atgcccagcc | 660 |
| actttccctt | ttcttttgcc | tcaggctgcc | agctatgctc | gttggcacgt | gacgtgtatc | 720 |
| tgagggagat | atgccaatga | ttacataagt | caagccaaag | catgaaacaa | gtgcatgagt | 780 |
| cgcagctcgg | tgagtcgaat | gaggtaatgc | gctgggcttc | cccatcatgt | taggtaaccg | 840 |
| attttctaca | caacaaatga | aggccgtccc | accgtttggg | aatccttaca | gagtacacca | 900 |
| ttaaccctg | gaaacattta | cacggagaca | cttatcaagt | agttagttag | ccatgagaac | 960 |

```
tgtgttctta caggctagga ctcagaatct ggataccttc ccttactgct tacttcacta    1020
tccaaccgca atcaccccat tccttcacgg gtgagtaccc ccttgtgacc atgcaaatca    1080
gcaacaatgg aaaaaaaaaa cacttcacca tgtagaggta tgaacttata tgtcgagcaa    1140
tgggtgtaaa gtattaccac tacgtacttg tattgttgtt atggctgggg aaatccgcgc    1200
ccatggaaac tcaatgggtg ggcaaaattg tggatgagat ggcgactgcc gacgtcacta    1260
gccatggacc aacagctcta ctgtggcact ccgtttacgg atgagacggc gccgatgatc    1320
gtcacaataa tagtagcccg aggcggcatt acagtgacta tatctatatt ccagcacatg    1380
catgaatgac cgtttgatag caagtgacag ctctggtctt tgcttttcaa cagatcccta    1440
taagctcgag caagtatgag agaatgacac ggtagaactc taaaaggtag tgataaatac    1500
atagcgtaaa aaggacacac agaccaagaa acaaaacgca aggaaagaga ggattttact    1560
ccggactccg ttccgtacaa cggaatcaag cgggtaaggg tcactaccaa acatgatgg     1620 atccttctga ttgccgctgg aaagcgcgcc gaaatcctgg ctcagactcg ggatatcggc    1680
caggttgaga ctagtgtgac cgtaagatac agccgcccac cattaccttg cggcgttgcc    1740
gtgtgttacc gtacagtccg cgtaccggct gtattggtac ggccagatgg aaaaaaaggg    1800
ccgcgcaaaa gagcttctcc ataacttggg aacaccgtgc ggcccatctt cctttttctt    1860
ttctctaccg tgtcctgata taccctcttt ctctcctctc cttttcttct tccaaccact    1920
caacttactg caagttgttc acattcgcca tggcttccac cttgagactg gcacctctg     1980 ctctccgttc cacctccatt gccgctaagc cggttgttca gtccgctgcc ttcaatggcc    2040
tgcgctgcta ctctaccggc aaggccaagg ttcgttctac ctcgataaca gtcattcctc    2100
ggatatttat actgatgtct ctcccttcta tagtccttga aggagacttt cgctgagaag    2160
ctccctgccg agatcgagaa ggtcaagaag ctccgcaagt acgcacagct ccctattcga    2220
cccttttgtc tacagcaggt gttgttaacc agtcaatcaa tgtgtgtagg gagcacggca    2280
gcaaggtcat cggcgaggtc acccttgacc aggcctatgg tggtgcccgt ggtgtcaagt    2340
gcctcgtgtg ggaggtatga tgaggaactt ggccaataat ttttttgagg agactatcta    2400
actgactttc ataggggttcc gtcctcgact ctgaggaggg tatccgtttc cgtggccgta    2460
ccgtaagttg catgtgacta aaacacaatt tgaaatgtat actgacagta ctttagatcc    2520
ccgagtgcca ggagctcctc cccaaggctc ccggtggtca ggagcctctt cccgagggtc    2580
tcttctggct gctcttgact ggcgagatcc ctaccgagca gcaggtccgc gatctgtctg    2640
ctgagtgggc tgcccgctcc gacctcccca agttcattga ggagctcatc gaccgctgcc    2700
ccagcactct gcaccccatg tcccagttct ctctggccgt caccgctctt gagcacgagt    2760
ctgctttcgc caaggcctat gccaagggta tcaacaagaa ggactactgg aactacacct    2820
tcgaggactc catggaccct attgccaagc tgcccaccat cgctgccaag atctaccgca    2880
acgtcttcaa ggatggcaag gtcgctccta tccagaagga caaggattac tcctacaact    2940
tggccaacca gctcggctac ggcgacaaca acgacttcgt tgagctcatg cgtctttacc    3000
tgaccatcca ctccgaccac gagggtggca acgtcagtgc tcacaccacc caccttgttg    3060
gtagcgctct gagctccccc atgctctctc tcgctgctgg tctgaacggt ctggctggac    3120
ctctccacgg attgtgagtt tttcaattct tttaatgtac gtcagattga agtgctttcg    3180
ctaatgtttc ttttttccaat cgcatagggc caaccaggaa gtccttaact ggctcaccaa    3240
gatgaaggcc gccattggca acgacctcag cgacgaggcc atcaagaact acctctggtc    3300
caccctgaac gccggccagg tcgttcccgg atacggtcac gccgtccttc gtaagaccga    3360
```

```
cccccgctac gtgtctcagc gcgagttcgc tcttcgcaag ctgcccgatg accccatgtt    3420
caagctggtc agccaggtct acaagatcgc tcctggtgtc ctgaccgagc acggcaagac    3480
caagaacccc taccccaacg tcgatgctgt aagttgcctc atgaatctgc gcccccgttg    3540
catgcgcgac cagtatactg accggtatgt agcactctgg tgtcctcctc cagtactatg    3600
gcctgactga ggccaactac tacaccgtcc tcttcggtgt ttcccgtgct ctgggtgtcc    3660
ttccccagct gatcatcgac cgtgcccttg gtgcccccat tgagcgcccc aagtcctaca    3720
gcaccgaggc cttcgccaag cttgttggtg ctaagctgta aatgagtttg ggatgacatg    3780
aaaaaccgga ggtgattctt atttcttttt acgataaaca cagcatcttg tattatgcct    3840
accctgttct ggtttagtat ttttgtgact ggggatgttt taaagtgttg gggtttgttc    3900
gattaatgta tgataggaca cggttcgagc gggccttgta acaaacagca cttgagaaat    3960
tccaagtcaa tcgtcttcta actctctttt ttttttttct taattcgtat gagattccgg    4020
gacagtatca cggagggaca ggcaagcaag cgtaaggggg gcggagggg caagctgac     4080
attgcaagtc ggatgccgaa gataagaatc agccagggag agagcaagag gagtgggatc    4140
ggcgcggtcg agaaacatac gtgattagtg ccaccagtgt cgagctgact gcaggtctgc    4200
atatcggtca aatcacagac cgaaggtgga aaaagctccg cggactgatc gtcgaacaac    4260
atagccagta aggcagcagg acaatgtgga agatgcattg ggtttcaatc aggattcgga    4320
gaatgaattg gacatttgag ttgtctagat acttatgcca acgctaattg cagaggttcg    4380
gggtgccgtg ggtgatctcc ggagcactcc atggccaagc ggaacaatac gagctacgta    4440
cggacagtga ggtcaggcag actgggagtc agatgagtaa ggactatcta gatagtcaat    4500
ccatggtcta ctccggaggt atctgaaggg aatgatgagg tactccgtat gagacaagca    4560
tatacacaaa ctactaacta cgggcgccgt agtccggggc gtgttcagag atcctgtcgg    4620
atcctcctca tcctcccatg atcgtggttg ctatggggga ggggcgggac tactccgtaa    4680
ctagtactga cctcccttt gtggtaccaa gtacgtagta gggagattct agatgttgtt    4740
attctgatta ttattattat tattattata ataattatta ttagtattgt aggagttaga    4800
tagatactcc gtgaatagat agtttgggtc tactatcatt ccagggccag ctggacgtgg    4860
gtcccccga tcgaccctct caaccgtttc ggaaaatgaa tgcagctcca gggtgtttgt    4920
tggggggag cccggtttgc tccgggcctc aactgaagcc ctcggctgtg gctcaccgcc    4980
gggcccgaag caggctagtg acctctgtgc cttgatcggg cttagtgcca tccccaatcg    5040
gccgatggcg ggcggtgatt ggatctcagt gggttcctgg ttgttgcggt ggtgagtgtg    5100
ctcattacta cggagtactc cttggtacgg agtgcttgga tgcgcccacg ccagacaaaa    5160
aaagcaactc tttgacctgc aattgggaga aaaaaccac catctgaatc gataggtacg    5220
tatgctctgc ctggaagccc gtcccacccc ctcgttgatc cttcttatat tttcatacct    5280
ctcttctctt ttccctcctc ttctctcctt catcttcttc cctcttcttc atccatacat    5340
acatacttcc tgctcctacc gtacatatac tcaaaccttc cccggagct acctgcttac     5400
ttggcctgtc ctcctcacca gtgacttctc catccgaaca acaaaaccgc tcttccctac    5460
tctcaaccca tttcgctctg gtcgttcgtc cttgacgttc cggacctgca gactatcttt    5520
cgattcttcg tgatccctta aggcgacgaa gcccccagat ttcccttggt cagggcccct    5580
ttcagcgctc ccaaggtcag ac                                            5602
```

<210> SEQ ID NO 12
<211> LENGTH: 474
<212> TYPE: PRT

<213> ORGANISM: Aspergillus niger

<400> SEQUENCE: 12

```
Met Ala Ser Thr Leu Arg Leu Gly Thr Ser Ala Leu Arg Ser Thr Ser
1               5                   10                  15

Ile Ala Ala Lys Pro Val Val Gln Ser Ala Ala Phe Asn Gly Leu Arg
            20                  25                  30

Cys Tyr Ser Thr Gly Lys Ala Lys Ser Leu Lys Glu Thr Phe Ala Glu
        35                  40                  45

Lys Leu Pro Ala Glu Ile Glu Lys Val Lys Lys Leu Arg Lys Glu His
    50                  55                  60

Gly Ser Lys Val Ile Gly Glu Val Thr Leu Asp Gln Ala Tyr Gly Gly
65                  70                  75                  80

Ala Arg Gly Val Lys Cys Leu Val Trp Glu Gly Ser Val Leu Asp Ser
                85                  90                  95

Glu Glu Gly Ile Arg Phe Arg Gly Arg Thr Ile Pro Glu Cys Gln Glu
            100                 105                 110

Leu Leu Pro Lys Ala Pro Gly Gly Gln Glu Pro Leu Pro Glu Gly Leu
        115                 120                 125

Phe Trp Leu Leu Leu Thr Gly Glu Ile Pro Thr Glu Gln Gln Val Arg
130                 135                 140

Asp Leu Ser Ala Glu Trp Ala Ala Arg Ser Asp Leu Pro Lys Phe Ile
145                 150                 155                 160

Glu Glu Leu Ile Asp Arg Cys Pro Ser Thr Leu His Pro Met Ser Gln
                165                 170                 175

Phe Ser Leu Ala Val Thr Ala Leu Glu His Glu Ser Ala Phe Ala Lys
            180                 185                 190

Ala Tyr Ala Lys Gly Ile Asn Lys Lys Asp Tyr Trp Asn Tyr Thr Phe
        195                 200                 205

Glu Asp Ser Met Asp Leu Ile Ala Lys Leu Pro Thr Ile Ala Ala Lys
    210                 215                 220

Ile Tyr Arg Asn Val Phe Lys Asp Gly Lys Val Ala Pro Ile Gln Lys
225                 230                 235                 240

Asp Lys Asp Tyr Ser Tyr Asn Leu Ala Asn Gln Leu Gly Tyr Gly Asp
                245                 250                 255

Asn Asn Asp Phe Val Glu Leu Met Arg Leu Tyr Leu Thr Ile His Ser
            260                 265                 270

Asp His Glu Gly Gly Asn Val Ser Ala His Thr Thr His Leu Val Gly
        275                 280                 285

Ser Ala Leu Ser Ser Pro Met Leu Ser Leu Ala Ala Gly Leu Asn Gly
    290                 295                 300

Leu Ala Gly Pro Leu His Gly Leu Ala Asn Gln Glu Val Leu Asn Trp
305                 310                 315                 320

Leu Thr Lys Met Lys Ala Ala Ile Gly Asn Asp Leu Ser Asp Glu Ala
                325                 330                 335

Ile Lys Asn Tyr Leu Trp Ser Thr Leu Asn Ala Gly Gln Val Val Pro
            340                 345                 350

Gly Tyr Gly His Ala Val Leu Arg Lys Thr Asp Pro Arg Tyr Val Ser
        355                 360                 365

Gln Arg Glu Phe Ala Leu Arg Lys Leu Pro Asp Pro Met Phe Lys
    370                 375                 380

Leu Val Ser Gln Val Tyr Lys Ile Ala Pro Gly Val Leu Thr Glu His
385                 390                 395                 400

Gly Lys Thr Lys Asn Pro Tyr Pro Asn Val Asp Ala His Ser Gly Val
```

```
                           405                 410                 415
Leu Leu Gln Tyr Tyr Gly Leu Thr Glu Ala Asn Tyr Tyr Thr Val Leu
                420                 425                 430

Phe Gly Val Ser Arg Ala Leu Gly Val Leu Pro Gln Leu Ile Ile Asp
            435                 440                 445

Arg Ala Leu Gly Ala Pro Ile Glu Arg Pro Lys Ser Tyr Ser Thr Glu
        450                 455                 460

Ala Phe Ala Lys Leu Val Gly Ala Lys Leu
465                 470

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ggtggacgag attttgtggt                                                  20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtctgacctt gggagcgctg                                                  20

<210> SEQ ID NO 15
<211> LENGTH: 1425
<212> TYPE: DNA
<213> ORGANISM: Aspergillus niger
<220> FEATURE:
<221> NAME/KEY: CDS
<222> LOCATION: (1)..(1425)

<400> SEQUENCE: 15 atg gct tcc acc ttg aga ctg ggc acc tct gct ctc cgt tcc acc tcc       48
Met Ala Ser Thr Leu Arg Leu Gly Thr Ser Ala Leu Arg Ser Thr Ser
1               5                   10                  15 att gcc gct aag ccg gtt gtt cag tcc gct gcc ttc aat ggc ctg cgc       96
Ile Ala Ala Lys Pro Val Val Gln Ser Ala Ala Phe Asn Gly Leu Arg
                20                  25                  30 tgc tac tct acc ggc aag gcc aag tcc ttg aag gag act ttc gct gag      144
Cys Tyr Ser Thr Gly Lys Ala Lys Ser Leu Lys Glu Thr Phe Ala Glu
            35                  40                  45 aag ctc cct gcc gag atc gag aag gtc aag aag ctc cgc aag gag cac      192
Lys Leu Pro Ala Glu Ile Glu Lys Val Lys Lys Leu Arg Lys Glu His
        50                  55                  60 ggc agc aag gtc atc ggc gag gtc acc ctt gac cag gcc tat ggt ggt      240
Gly Ser Lys Val Ile Gly Glu Val Thr Leu Asp Gln Ala Tyr Gly Gly
65                  70                  75                  80 gcc cgt ggt gtc aag tgc ctc gtg tgg gag ggt tcc gtc ctc gac tct      288
Ala Arg Gly Val Lys Cys Leu Val Trp Glu Gly Ser Val Leu Asp Ser
                85                  90                  95 gag gag ggt atc cgt ttc cgt ggc cgt acc atc ccc gag tgc cag gag      336
Glu Glu Gly Ile Arg Phe Arg Gly Arg Thr Ile Pro Glu Cys Gln Glu
                100                 105                 110 ctc ctc ccc aag gct ccc ggt ggt cag gag cct ctt ccc gag ggt ctc      384
Leu Leu Pro Lys Ala Pro Gly Gly Gln Glu Pro Leu Pro Glu Gly Leu
            115                 120                 125
```

|   |   |
|---|---|
| ttc tgg ctg ctc ttg act ggc gag atc cct acc gag cag cag gtc cgc<br>Phe Trp Leu Leu Leu Thr Gly Glu Ile Pro Thr Glu Gln Gln Val Arg<br>130                        135                        140 | 432 |
| gat ctg tct gct gag tgg gct gcc cgc tcc gac ctc ccc aag ttc att<br>Asp Leu Ser Ala Glu Trp Ala Ala Arg Ser Asp Leu Pro Lys Phe Ile<br>145                        150                        155                        160 | 480 |
| gag gag ctc atc gac cgc tgc ccc agc act ctg cac ccc atg tcc cag<br>Glu Glu Leu Ile Asp Arg Cys Pro Ser Thr Leu His Pro Met Ser Gln<br>                        165                        170                        175 | 528 |
| ttc tct ctg gcc gtc acc gct ctt gag cac gag tct gct ttc gcc aag<br>Phe Ser Leu Ala Val Thr Ala Leu Glu His Glu Ser Ala Phe Ala Lys<br>                  180                        185                        190 | 576 |
| gcc tat gcc aag ggt atc aac aag aag gac tac tgg aac tac acc ttc<br>Ala Tyr Ala Lys Gly Ile Asn Lys Lys Asp Tyr Trp Asn Tyr Thr Phe<br>                195                        200                        205 | 624 |
| gag gac tcc atg gac ctc att gcc aag ctg ccc acc atc gct gcc aag<br>Glu Asp Ser Met Asp Leu Ile Ala Lys Leu Pro Thr Ile Ala Ala Lys<br>210                        215                        220 | 672 |
| atc tac cgc aac gtc ttc aag gat ggc aag gtc gct cct atc cag aag<br>Ile Tyr Arg Asn Val Phe Lys Asp Gly Lys Val Ala Pro Ile Gln Lys<br>225                        230                        235                        240 | 720 |
| gac aag gat tac tcc tac aac ttg gcc aac cag ctc ggc tac ggc gac<br>Asp Lys Asp Tyr Ser Tyr Asn Leu Ala Asn Gln Leu Gly Tyr Gly Asp<br>                        245                        250                        255 | 768 |
| aac aac gac ttc gtt gag ctc atg cgt ctt tac ctg acc atc cac tcc<br>Asn Asn Asp Phe Val Glu Leu Met Arg Leu Tyr Leu Thr Ile His Ser<br>                  260                        265                        270 | 816 |
| gac cac gag ggt ggc aac gtc agt gct cac acc acc cac ctt gtt ggt<br>Asp His Glu Gly Gly Asn Val Ser Ala His Thr Thr His Leu Val Gly<br>                        275                        280                        285 | 864 |
| agc gct ctg agc tcc ccc atg ctc tct ctc gct gct ggt ctg aac ggt<br>Ser Ala Leu Ser Ser Pro Met Leu Ser Leu Ala Ala Gly Leu Asn Gly<br>                  290                        295                        300 | 912 |
| ctg gct gga cct ctc cac gga ttg gcc aac cag gaa gtc ctt aac tgg<br>Leu Ala Gly Pro Leu His Gly Leu Ala Asn Gln Glu Val Leu Asn Trp<br>305                        310                        315                        320 | 960 |
| ctc acc aag atg aag gcc gcc att ggc aac gac ctc agc gac gag gcc<br>Leu Thr Lys Met Lys Ala Ala Ile Gly Asn Asp Leu Ser Asp Glu Ala<br>                        325                        330                        335 | 1008 |
| atc aag aac tac ctc tgg tcc acc ctg aac gcc ggc cag gtc gtt ccc<br>Ile Lys Asn Tyr Leu Trp Ser Thr Leu Asn Ala Gly Gln Val Val Pro<br>                          340                        345                        350 | 1056 |
| gga tac ggt cac gcc gtc ctt cgt aag acc gac ccc cgc tac gtg tct<br>Gly Tyr Gly His Ala Val Leu Arg Lys Thr Asp Pro Arg Tyr Val Ser<br>                        355                        360                        365 | 1104 |
| cag cgc gag ttc gct ctt cgc aag ctg ccc gat gac ccc atg ttc aag<br>Gln Arg Glu Phe Ala Leu Arg Lys Leu Pro Asp Asp Pro Met Phe Lys<br>370                        375                        380 | 1152 |
| ctg gtc agc cag gtc tac aag atc gct cct ggt gtc ctg acc gag cac<br>Leu Val Ser Gln Val Tyr Lys Ile Ala Pro Gly Val Leu Thr Glu His<br>385                        390                        395                        400 | 1200 |
| ggc aag acc aag aac ccc tac ccc aac gtc gat gct cac tct ggt gtc<br>Gly Lys Thr Lys Asn Pro Tyr Pro Asn Val Asp Ala His Ser Gly Val<br>                        405                        410                        415 | 1248 |
| ctc ctc cag tac tat ggc ctg act gag gcc aac tac tac acc gtc ctc<br>Leu Leu Gln Tyr Tyr Gly Leu Thr Glu Ala Asn Tyr Tyr Thr Val Leu<br>                  420                        425                        430 | 1296 |
| ttc ggt gtt tcc cgt gct ctg ggt gtc ctt ccc cag ctg atc atc gac<br>Phe Gly Val Ser Arg Ala Leu Gly Val Leu Pro Gln Leu Ile Ile Asp<br>                  435                        440                        445 | 1344 |

```
cgt gcc ctt ggt gcc ccc att gag cgc ccc aag tcc tac agc acc gag    1392
Arg Ala Leu Gly Ala Pro Ile Glu Arg Pro Lys Ser Tyr Ser Thr Glu
    450                 455                 460 gcc ttc gcc aag ctt gtt ggt gct aag ctg taa                        1425
Ala Phe Ala Lys Leu Val Gly Ala Lys Leu
465                 470

<210> SEQ ID NO 16
<211> LENGTH: 3874
<212> TYPE: DNA
<213> ORGANISM: Aspergillus niger

<400> SEQUENCE: 16
ggtctcatag ggggaggtgg attgtcgctg ggtgtgctcg ttgttggcct ttcgaaggag      60
taggggctgg agacgacgga ggttggatac gaggaacgtc gggtccctga gaggctccca    120
ttcttccatc gcttggcgga aaagaggatg gatggctgcg acggccgttt ctggcagtcg    180
gtattcatca atctcgctgc ggtacttgat ctccatggac tccagcttat cggtgatttc    240
gtcgaacttt gctcgagtgt cttccttctg aagatctcct agttgcccga tggctgtgac    300
gagctcagac agctggtcga ccttgagctg atttgtatca agttgttcca cgacctgggc    360
ttcctctagc tcgatgtatt ttttccgctc tgtcagaccc ttccactcgt ctgcaaacgc    420
ctctaggtcg ttccgagcac gttgcgcgat tttccaggct ctccctcgc cttgagtaac    480 gaatgtttgc ggcgtcatca gaccagctgt agacgtgagc accttctggt ccttcccggt    540
cgcatcgata agcgacttta gcacgttcgg aacttccaag ccctccatat ccttttccat    600
ctcgcgcgca gttcggaact ggggcttcgc gcgagccact ggtgtcccgg tcccgctccg    660
gccctctcgt ttacgctcct ccttcttttt ccgtcgcctc ttgcgctctt catctgagct    720
atcctcgacg gactcgcccc ggagagctgc tgcccgcttt tcctcttctc gcgcttgctt    780
tgtcttctca cggaccgcac ccagaccggc acctgtagga cgagcctggg cctcgatcgg    840
gttgacgata ccttgaccgg aagaacccaa accctgtccc tcgacgtaac ccatcttggc    900
catcatgcgc gcggcgaagg agttgcctcc ggacattcct ttgccagcat gttgcctcc    960 gcctttcatc gctgactgcg cggtgttgtt ccgaggattg cgacgagagc ttcctagccc   1020
gccgtgagaa ggaggcgact cagagcgaga cgacgcgcga gcaaaaccgc gaaagcccat   1080
ggttgggcgg taatcttctt cttcctcttc atcggagctc atgtcggcga ttttgcgttt   1140
ctggccggcg tatggcgagg acgaggggga ctccatggcc gggcttgagg acaaaaggcg   1200
acacaaagga aggaatcgag attcacggcg aggaagtaga gagaaagccc ggcagcatga   1260
cggagatcct gattgagtat gaatggttga agctaaaaga tggtggatcc aaatgccggg   1320
aaacttcggc gcggggaaat gcgccctccg aagaaacaag ccgttatgac gttgaacttc   1380
ttcatctctc cttcttcctt cttcttcctt tttcccttca gcaactctcc tctcatccct   1440
ctaaacaccc ccgggtctat agtaatagtg catcttgctc tgttccaatt atcgctcaca   1500
atggctgctt ccctcgtccg cacctctgcc cgtacggccc tgcgcgccgg agcttcggct   1560
actcccagaa ctgccggcat ggcgggcttg accttggccc gcggcaaggc tactctccct   1620
gacctgtcct gtatgcatcc agctgccatt ctcgagacgc atagatcttg aagtcaccga   1680
actgactccc tgtagacgac tatggcgctc tcgagccctc catctccggc aagatcatgg   1740
agcttcacca caagaaccac caccagacct acgtcaacag ctacaacact gccattgagc   1800
agctccagga ggcccagcac aagaacgaca ttgcggccca gattgccctc aagcccctga   1860
tcaacttcca cggtggtggt cacctgaacc acaccctctt ctgggagaac cttgctccca   1920
```

```
agagcgctgg cggtggtgag cccccgtccg gtgccctgtc gactgccatc aacgacacct   1980
tcggcagcct ggaggagttc cagaacaaga tgaacgctgc tcttgctgct atccagggta   2040
gcggctgggc ctggctcgtc aaggacaagc agaccggtca cattggcatc aaggcctacg   2100
ccgtaagaat gcaccatgca tgcgaagaaa gtatttgagt tggctaacga tttcacagaa   2160
ccaggacccc gttgtcggtc agttccagcc cctgctgggt attgacgcct gggagcacgc   2220
ctactagtaa gtgcacctga cccaacccgt tggaatcatc aggagctaat attgtctatc   2280
tagcctccaa taccagaacc gcaaggccga gtacttcaag gccatctggg aggtcatcaa   2340
ctggaaggcc gtggagaagc gcttctccgc ctaaagcttt ctttatgata tgaactgtat   2400
attgacgcgg cttgattagc gattgtggat ctgcgtatta tgtgtactat ggatttggaa   2460
ctaatcaggc tcaatccgat gccctaatgc aaattccgta ttaatggcac tcttctcttc   2520
tttttatcct ctccgtaaac aaatagaccc ttgttcctca tcagccacag tggctgaagc   2580
tcggcaggtg gcggatggca gctccgtaac atccggtaaa cgtaatacag cgccgatcat   2640
gtttcacatt cgctgcatcg ccggcttcat cttcatcttt atcttctttt tgtcctccca   2700
tctcctccgc ttcttcctcc attcctcccc ccatgtctga tgacagtccg ggagaaaggc   2760
gcggcttccg ggccttcttc gccaatgctc tccggcccaa gaaatcccgg caagtcttgc   2820
gcaagggcta cagcgcatcc actccagacc tccgagccgg cttcaagcgg cccagcacta   2880
ccagcgaaga tgtccctccg ctgccctccc tggcgccatt ggaggcacat cgcctcaaat   2940
accgagaact caacgccaac aaagacaccc agctcggtga agccgcgat cacaccgaac    3000 tcctgcacgc catcggcgtc caggatctcg atccctcaga cccttacgcc aaccgcgccg   3060
attccgacaa ccgtcctcct ggcgagccgg taatcgccag tctcccccg atcctctggg    3120 aggagatctg ctcctatctc acgcccgcag accaagccag tctcgccttc gccagcaaaa   3180
ccctcctctc caagctcgcc ccgctccaac cctggcaagc cctcaaccac ccttccaacc   3240
gcgaataccg ctccgacttc ctcgtctccc aagatcgcta cctcccccat catctcctct   3300
gctttccatg cgcccgctac caccgtcgca cccaagaggg ccatgagaaa cttcaacccg   3360
cccatgtcat caatcccctc ttcaactgcc ccaacatgcg caacaccctc ctcccgcccc   3420
ctcgtcaccg catcacccac ggccgcaccc tccccttcag cttcgtccaa ctcgtcatgc   3480
gcgcccacaa atactcccct tcctacggcc tcgccccgga tccctctcc cgccgctggc    3540 gccgcgatga ctggtcccac cacacccgct tccacatcca caaggccac ctgctaatgc    3600 gggtcatcag cacccgcttc gcagacccag accttcctcc cagctcgcag cgtctcctcc   3660
tctactcccg cgaagactac tggccgtact tctccgcgtg cgcgcactgg cgcgacggcg   3720
aactcatgaa cgtgtgcaaa tgtgccctca ctcatgtccc cgcaccccgc gacacctctg   3780
ccctacaggg cctcgaacac cgcgctaagg atatcatggc gcggcgcatc cacaacccta   3840
actcaattgc cacccctatgc gggaaatgtc gtcc                              3874
```

<210> SEQ ID NO 17
<211> LENGTH: 231
<212> TYPE: PRT
<213> ORGANISM: Aspergillus niger

<400> SEQUENCE: 17

Met Ala Ala Ser Leu Val Arg Thr Ser Ala Arg Thr Ala Leu Arg Ala
1               5                   10                  15

Gly Ala Ser Ala Thr Pro Arg Thr Ala Gly Met Ala Gly Leu Thr Phe
            20                  25                  30

```
Ala Arg Gly Lys Ala Thr Leu Pro Asp Leu Ser Tyr Asp Tyr Gly Ala
         35                  40                  45

Leu Glu Pro Ser Ile Ser Gly Lys Ile Met Glu Leu His His Lys Asn
 50                  55                  60

His His Gln Thr Tyr Val Asn Ser Tyr Asn Thr Ala Ile Glu Gln Leu
 65                  70                  75                  80

Gln Glu Ala Gln His Lys Asn Asp Ile Ala Ala Gln Ile Ala Leu Lys
                 85                  90                  95

Pro Leu Ile Asn Phe His Gly Gly His Leu Asn His Thr Leu Phe
            100                 105                 110

Trp Glu Asn Leu Ala Pro Lys Ser Ala Gly Gly Glu Pro Pro Ser
            115                 120                 125

Gly Ala Leu Ser Thr Ala Ile Asn Asp Thr Phe Gly Ser Leu Glu Glu
130                 135                 140

Phe Gln Asn Lys Met Asn Ala Ala Leu Ala Ala Ile Gln Gly Ser Gly
145                 150                 155                 160

Trp Ala Trp Leu Val Lys Asp Lys Gln Thr Gly His Ile Gly Ile Lys
                165                 170                 175

Ala Tyr Ala Asn Gln Asp Pro Val Val Gly Gln Phe Gln Pro Leu Leu
            180                 185                 190

Gly Ile Asp Ala Trp Glu His Ala Tyr Tyr Leu Gln Tyr Gln Asn Arg
            195                 200                 205

Lys Ala Glu Tyr Phe Lys Ala Ile Trp Glu Val Ile Asn Trp Lys Ala
            210                 215                 220

Val Glu Lys Arg Phe Ser Ala
225                 230

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ggtctcatag ggggaggtgg                                                     20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggacgacatt tcccgcatag                                                     20

<210> SEQ ID NO 20
<211> LENGTH: 696
<212> TYPE: DNA
<213> ORGANISM: Aspergillus niger
<220> FEATURE:
<221> NAME/KEY: CDS
<222> LOCATION: (1)..(696)

<400> SEQUENCE: 20 atg gct gct tcc ctc gtc cgc acc tct gcc cgt acg gcc ctg cgc gcc      48
Met Ala Ala Ser Leu Val Arg Thr Ser Ala Arg Thr Ala Leu Arg Ala
 1               5                  10                  15 gga gct tcg gct act ccc aga act gcc ggc atg gcg ggc ttg acc ttt      96
```

-continued

```
                Gly Ala Ser Ala Thr Pro Arg Thr Ala Gly Met Ala Gly Leu Thr Phe
                             20              25              30 gcc cgc ggc aag gct act ctc cct gac ctg tcc tac gac tat ggc gct        144
Ala Arg Gly Lys Ala Thr Leu Pro Asp Leu Ser Tyr Asp Tyr Gly Ala
             35              40              45 ctc gag ccc tcc atc tcc ggc aag atc atg gag ctt cac cac aag aac        192
Leu Glu Pro Ser Ile Ser Gly Lys Ile Met Glu Leu His His Lys Asn
         50              55              60 cac cac cag acc tac gtc aac agc tac aac act gcc att gag cag ctc        240
His His Gln Thr Tyr Val Asn Ser Tyr Asn Thr Ala Ile Glu Gln Leu
65              70              75              80 cag gag gcc cag cac aag aac gac att gcg gcc cag att gcc ctc aag        288
Gln Glu Ala Gln His Lys Asn Asp Ile Ala Ala Gln Ile Ala Leu Lys
             85              90              95 ccc ctg atc aac ttc cac ggt ggt ggt cac ctg aac cac acc ctc ttc        336
Pro Leu Ile Asn Phe His Gly Gly Gly His Leu Asn His Thr Leu Phe
            100             105             110 tgg gag aac ctt gct ccc aag agc gct ggc ggt ggt gag ccc ccg tcc        384
Trp Glu Asn Leu Ala Pro Lys Ser Ala Gly Gly Gly Glu Pro Pro Ser
            115             120             125 ggt gcc ctg tcg act gcc atc aac gac acc ttc ggc agc ctg gag gag        432
Gly Ala Leu Ser Thr Ala Ile Asn Asp Thr Phe Gly Ser Leu Glu Glu
        130             135             140 ttc cag aac aag atg aac gct gct ctt gct gct atc cag ggt agc ggc        480
Phe Gln Asn Lys Met Asn Ala Ala Leu Ala Ala Ile Gln Gly Ser Gly
145             150             155             160 tgg gcc tgg ctc gtc aag gac aag cag acc ggt cac att ggc atc aag        528
Trp Ala Trp Leu Val Lys Asp Lys Gln Thr Gly His Ile Gly Ile Lys
            165             170             175 gcc tac gcc aac cag gac ccc gtt gtc ggt cag ttc cag ccc ctg ctg        576
Ala Tyr Ala Asn Gln Asp Pro Val Val Gly Gln Phe Gln Pro Leu Leu
            180             185             190 ggt att gac gcc tgg gag cac gcc tac tac ctc caa tac cag aac cgc        624
Gly Ile Asp Ala Trp Glu His Ala Tyr Tyr Leu Gln Tyr Gln Asn Arg
        195             200             205 aag gcc gag tac ttc aag gcc atc tgg gag gtc atc aac tgg aag gcc        672
Lys Ala Glu Tyr Phe Lys Ala Ile Trp Glu Val Ile Asn Trp Lys Ala
210             215             220 gtg gag aag cgc ttc tcc gcc taa                                        696
Val Glu Lys Arg Phe Ser Ala
225             230
```